US 6,709,869 B2

(12) United States Patent
Mian et al.

(10) Patent No.: US 6,709,869 B2
(45) Date of Patent: Mar. 23, 2004

(54) DEVICES AND METHODS FOR USING CENTRIPETAL ACCELERATION TO DRIVE FLUID MOVEMENT IN A MICROFLUIDICS SYSTEM

(75) Inventors: Alec Mian, Cambridge, MA (US); Stephen G. Kieffer-Higgins, Dorchester, MA (US); George D. Corey, Newton, MA (US)

(73) Assignee: Tecan Trading AG (CH)

( * ) Notice: Subject to any disclaimer, the term of this patent is extended or adjusted under 35 U.S.C. 154(b) by 148 days.

(21) Appl. No.: 09/989,582

(22) Filed: Nov. 20, 2001

(65) Prior Publication Data

US 2002/0137218 A1 Sep. 26, 2002

Related U.S. Application Data

(62) Division of application No. 08/768,990, filed on Dec. 18, 1996, now Pat. No. 6,319,469.
(60) Provisional application No. 60/008,819, filed on Dec. 18, 1995, and provisional application No. 60/023,756, filed on Aug. 12, 1996.

(51) Int. Cl.[7] .................. G01N 35/00; G01N 33/48; G01N 33/86; G01N 9/30; B32B 27/04
(52) U.S. Cl. ................ 436/45; 436/43; 436/63; 436/66; 436/70; 422/50; 422/64; 422/63; 422/67; 422/72
(58) Field of Search .................. 422/64, 50, 63, 422/67, 72; 436/45, 43, 63, 66, 70

(56) References Cited

U.S. PATENT DOCUMENTS 3,679,367 A  7/1972 Negersmith
3,955,755 A  * 5/1976 Breillatt, Jr. et al. ......... 494/10

(List continued on next page.)

FOREIGN PATENT DOCUMENTS

| DE | 4410224 | 9/1995 |
| EP | 322657 | 7/1989 |
| EP | 417305 A1 | 3/1991 |
| EP | 305210 | 12/1993 |
| EP | 616218 A1 | 9/1994 |
| EP | 637367 B1 | 12/1997 |
| WO | 93/22053 | 11/1993 |
| WO | 93/22058 | 11/1993 |
| WO | 95/33986 | 12/1995 |

OTHER PUBLICATIONS

Anderson, "Analytical Techniques for Cell Fractions" (1968), Anal. Biochem., 28:545–562.
Aoki et al., "Electrochemical Response at Microarray Electrodes in Flowing Streams and Determination of Catecholamines", (1990), Anal. Chem., 62: 2206–2210.
Arquint et al., "Micromachined Analyzers on a Silicon Chip", (Sep. 1994), Clinical Chemistry, vol. 40, No. 9, pp. 1805–1809.

(List continued on next page.)

*Primary Examiner*—Jill Warden
*Assistant Examiner*—Brian Sines
(74) *Attorney, Agent, or Firm*—McDonnell Boehnen Hulbert & Berghoff

(57) ABSTRACT

This invention relates to methods and apparatus for performing microanalytic and microsynthetic analyses and procedures. The invention provides a microsystem platform and a micromanipulation device for manipulating the platform that utilizes the centripetal force resulting from rotation of the platform to motivate fluid movement through microchannels. The microsystem platforms of the invention are also optionally provided having system informatics and data acquisition, analysis and storage and retrieval informatics encoded on the surface of the disk opposite to the surface containing the fluidic components. Methods specific for the apparatus of the invention for performing any of a wide variety of microanalytical or microsynthetic processes are provided.

14 Claims, 64 Drawing Sheets

U.S. PATENT DOCUMENTS

| | | | |
|---|---|---|---|
| 4,729,862 | A | 7/1981 | Salatiello et al. |
| 4,381,291 | A | 4/1983 | Ekins et al. |
| 4,515,889 | A | 5/1985 | Klose et al. |
| 4,676,952 | A | 6/1987 | Edelmann et al. |
| 4,745,072 | A | 5/1988 | Ekins |
| 4,940,527 | A | 7/1990 | Kazlauskas et al. |
| 5,006,749 | A | 4/1991 | White |
| 5,061,381 | A | 10/1991 | Burd |
| 5,160,702 | A | 1/1992 | Kopf-Sill |
| 4,154,793 | A | 5/1992 | Guigan |
| 5,122,284 | A | 6/1992 | Braynin et al. |
| 5,171,695 | A | 12/1992 | Ekins |
| 5,173,193 | A | 12/1992 | Schembri |
| 5,173,262 | A | 12/1992 | Burtis et al. |
| 5,186,844 | A | 2/1993 | Burd |
| 5,242,606 | A * | 9/1993 | Braynin et al. ............. 210/787 |
| 5,242,803 | A | 9/1993 | Burtis et al. |
| 5,262,294 | A | 11/1993 | Kroy |
| 5,275,016 | A | 1/1994 | Chatterjee et al. |
| 5,279,150 | A * | 1/1994 | Katzer et al. ............. 73/61.66 |
| 5,304,348 | A | 4/1994 | Burd et al. |
| 5,304,487 | A | 4/1994 | Wilding |
| 5,368,704 | A | 11/1994 | Madou |
| 5,403,415 | A | 4/1995 | Schembri |
| 5,409,665 | A | 4/1995 | Burd |
| 5,413,732 | A | 5/1995 | Buhl |
| 5,426,032 | A | 6/1995 | Phillips et al. |
| 5,432,009 | A | 7/1995 | Tabata |
| 5,457,053 | A | 10/1995 | Burd et al. |
| 5,472,603 | A | 12/1995 | Schembri |
| 5,478,750 | A | 12/1995 | Berstein et al. |
| 5,496,520 | A | 3/1996 | Kelton et al. |
| 5,518,930 | A | 5/1996 | Burd et al. |
| 5,591,643 | A | 1/1997 | Schembri et al. |
| 5,599,411 | A | 2/1997 | Schembri |
| 5,624,597 | A | 4/1997 | Buhl et al. |
| 5,639,428 | A | 6/1997 | Cottingham |
| 5,693,233 | A | 12/1997 | Schembri |
| 6,319,469 | B1 | 11/2001 | Mian et al. |

OTHER PUBLICATIONS

Ballantine et al., "Surface Acoustic Wave", (Jun. 1989), Anal, Chem., 61/11: pp: 704–715.

Bertrand et al., "A One–Step Determiniation of Serum 5'–nucleotidase using a centrifulgal Analyzer", (1982), Clinica Chimica Acta, 119:275–284.

Blackburn et al., "Electrochemiluminescence Detection for Development of Immunoassays and DNA Probe Assays for Clinical Diagnostics", (1991), Clin. Chem., 37/9: 1534–1539.

Bor Fuh et al., "Isolation of Human Blood Cells, Platelets, and Plasma Proteins by Centrifugal SPLITT Fractionation", (1995), Biotechnol. Prog., 11: 14–20.

Burtis et al., "Optimization and Analytical Application of the Technique of Dynamic Introduction of Liquids into Centrifugal Analyzers", (1974), Clin. Chem., 20: 932–941.

Burtis et al., "Development of a Multipurpose Optical System for Use with a Centrifugal Fast Analyzer", (1975), Clin. Chem., 21/9: 1225–1233.

Cho et al., "Development of a Multichannel Electrochemical Centrifugal Analyzer" (1982), Clin. Chem., 28/9: 1961–1965.

Collison et al., "Chemical Sensors for Bedside Monitoring of Critically Ill Patients" (Apr. 1990), Anal. Chem., 62/7: pp. 425–437.

Columbus et al., "Architextured" Fluid Management of Biological Liquids, (1987), Clin. Chem., 33/9: 1531–1537.

Dessy, "Waveguides as Chemical Sensors", (Oct. 1989), Anal. Chem., 61/19: 1079–1094.

Ekins et al., "Multianalyte Microspot Immunoassay. The microanalytical 'compact disk' of the future", (1992), Ann. Biol. Clin., 50: 337–353.

Esashi et al., "Anodic Bonding for Integrated Capacitive Sensors" (Jul. 1992), Proc. Micro. Electro Mechanical Systems, 11: 43–48.

Foucault, "Countercurrent Chromatography" (1991), Anal. Chem., 63.

Fritsche et al., "Enzymatic Endpoint Analysis of Glucose with the Hexokinase Method and the Union Carbide Fast Centrifugal Analyzer", (1975), Clin Biochem., 8: 240–246.

Glass et al., "Effect of Numerical aperture on signal level in cylindrical waveguide evanescent fluorosensors" (Jun. 1987), Appl. Optics, 26/11: 2181–2187.

Haab et al., "Single Molecule Fluorescnece Burst Detection of DNA Fragments Separated by Capillary Electrophoresis" Anal. Chem., 1995, 67, 3253–3260.

Hadjiioannou et al., "Automated Enzymic Determination of Ethanol in Blood, Serum, and Urine with a Miniature Centrifugal Analyzer", (1976), Clin. Chem. 22/6:802–805.

Heineman, "Biosensors Based on Polymer Networks Formed by Gamma Irradiation Crosslinking", (1993), App. Biochem. Biotech., 41: 87–97.

Ikada, "Surface Modification of Polymers for Medical Applications", (1994), Biomaterials, 15/10: 725–736.

Lamture et al., "Direct Detectoin of Nucleic Acid Hybridization on the Surface of a Charge Coupled Device", (1994) Nucleic Acids Res., 22/11: 2121–2125.

Lee et al., "Automated System for Fractionation of Blood Samples" (1978), Clin. Chem., 24/8: 1361–1365.

Linliu et al., "Development of a Centrifuge Ball Viscometer for Polymer Melts", (1994), Rev. Sci. Instrum., 65/12: 3823–3828.

Nakagawa et al., "A Micro Chemical Analyzing System Integrated on a Silicon Wafer", Proc. IEEE Workshop of Micro Electro Mechanical Systems, p. 89.

Poole et al., "Instrumental Thin–Layer Chromatography", (Jan. 1994), Anal. Chem., 66/1: 27A–37A.

Reijenga et al., "Effect of Electroosmosis on Detection in Isotachophoresis", (1983), J. Chromatography, 260: 241–254.

Renoe et al., "A Versatile Minidisc Module for a Centrifugal Analyzer" (1974), Clain. Chem., 20/8:955–960.

Rosenzweig et al., "Laser–Based Particle–Counting Microimmunoassay for the Analysis of Single Human Erythorcytes" (1994), Anal. Chem., 66: 1771–1776.

Schembri et al., "Portable Simultaneous Multiple Analyte Whole–Blood Analyzer for Point–of–Care Testing" (1992), Clin. Chem., 38/9: 1665–1670.

Shoji & Esashi, "Micro flow cell for blood gas analysis realizing very small sample volume" (1992), Sensors and Actuators, B8: 205–208.

Wilding et al., "Manipulation and Flow of Biological Fluids in Straight Channels Micromachined in Silicon" (1994), Automat. Analyt. Tech., 40: 43–47.

Wilding et al., Manipulation and Flow of Bioligical Fluids in Straight Channels Micromachined in Silicon (1994), Clin. Chem., 40/1: 43–47.

* cited by examiner

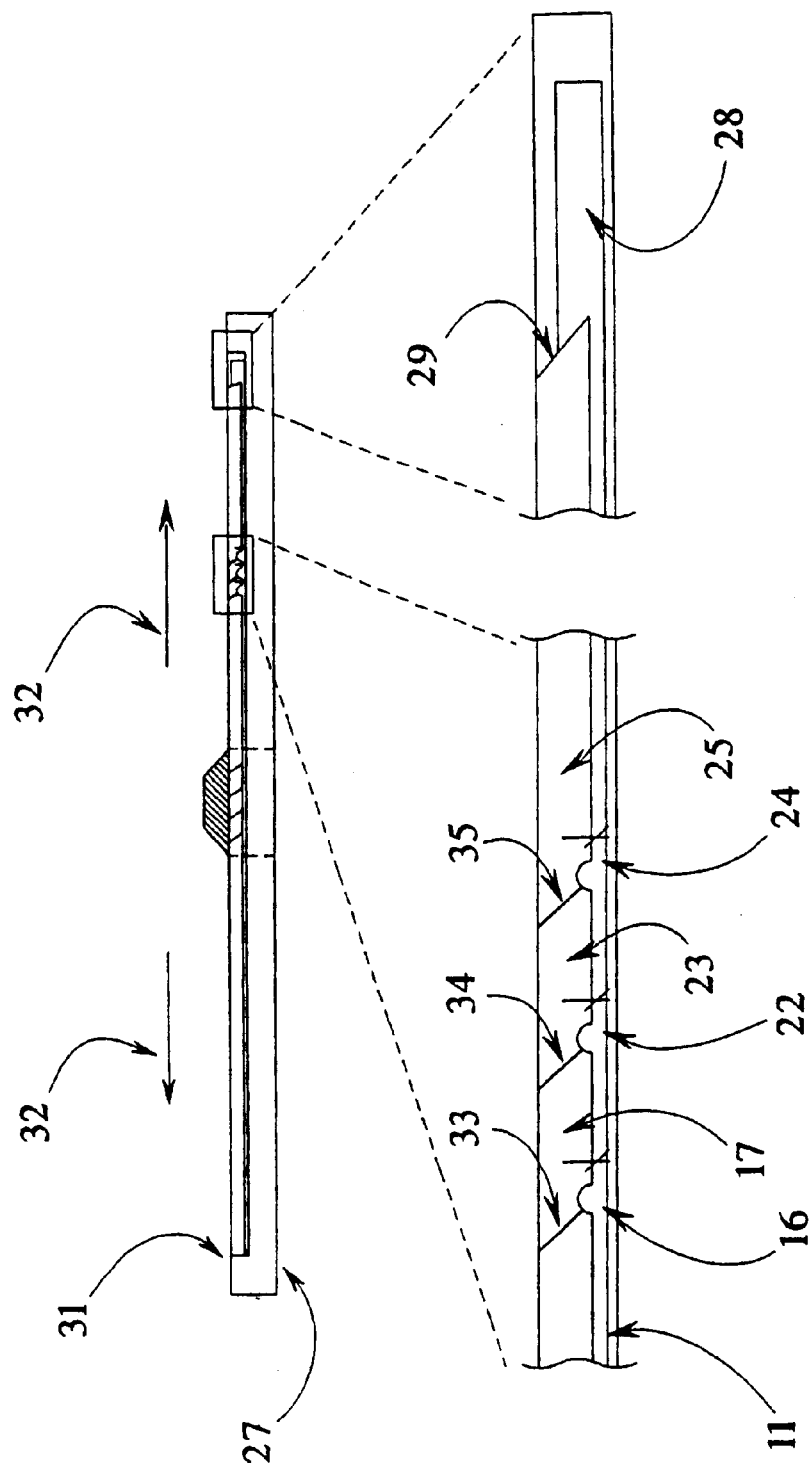

LINEAR CONFIGURATION

RADIAL CONFIGURATION

RADIAL CONFIGURATION

OUTLET

DEVICES AND METHODS FOR USING CENTRIPETAL ACCELERATION TO DRIVE FLUID MOVEMENT IN A MICROFLUIDICS SYSTEM

This application is a divisional of U.S. Ser. No. 08/768,990, filed Dec. 18, 1996, now U.S. Pat. No. 6,319,469, issued Nov. 20, 2001, which application claims priority to U.S. patent application Ser. No. 08/761,063, filed Dec. 5, 1996 and to U.S. Provisional Application Serial No. 60/008,819, filed Dec. 18, 1995, and No. 60/023,756, filed Aug. 12, 1996, the disclosures of each of which are explicitly incorporated by reference herein.

BACKGROUND OF THE INVENTION

1. Field of the Invention

This invention relates to methods and apparatus for performing microanalytic and microsynthetic analyses and procedures. In particular, the invention relates to microminiaturization of genetic, biochemical and chemical processes related to analysis, synthesis and purification. Specifically, the invention provides a microsystem platform and a micromanipulation device to manipulate the platform by rotation, thereby utilizing the centripetal forces resulting from rotation of the platform to motivate fluid movement through microchannels embedded in the microplatform. The microsystem platforms of the invention are also provided optionally having system informatics and data acquisition, analysis and storage and retrieval informatics encoded on the surface of the disk opposite to the surface containing the fluidic components. Methods for performing any of a wide variety of microanalytical or microsynthetic processes using the microsystems apparatus of the invention are also provided.

2. Background of the Related Art

In the field of medical, biological and chemical assays, a mechanical and automated fluid handling systems and instruments produced to operate on a macroscopic (i.e., milliliters and milligrams) scale are known in the prior art.

U.S. Pat. No. 4,279,862, issued Jul. 21, 1981 to Bertaudiere et al. disclose a centrifugal photometric analyzer.

U.S. Pat. No. 4,381,291, issued Apr. 26, 1983 to Ekins teach analytic measurement of free ligands.

U.S. Pat. No. 4,515,889, issued May 7, 1985 to Klose et al. teach automated mixing and incubating reagents to perform analytical determinations.

U.S. Pat. No. 4,676,952, issued Jun. 30, 1987 to Edelmann et al teach a photometric analysis apparatus.

U.S. Pat. No. 4,745,072, issued May 17, 1988 to Ekins discloses immunoassay in biological fluids.

U.S. Pat. No. 5,160,702 issued Nov. 3, 1992 to Kopf-Sill et al. discloses a centrifuge rotor for analyzing solids in a liquid.

U.S. Pat. No. 5,171,695, issued Dec. 15, 1992 to Ekins discloses determination of analyte concentration using two labeling markers.

U.S. Pat. No. 5,173,262 issued Dec. 22, 1996 to Burtis et al. discloses a centrifuge rotor for processing liquids.

U.S. Pat. No. 5,242,803, issued Sep. 7, 1993 to Burtis et al. disclose a rotor assembly for carrying out an assay.

U.S. Pat. No. 5,409,665, issued Apr. 25, 1995 to Burd disclose cuvette filling in a centrifuge rotor.

U.S. Pat. No. 5,413,732, issued May 9, 1995 to Buhl et al. teach preparation of lyophilized reagent spheres for use in automated centrifugal blood analyzers.

U.S. Pat. No. 5,432,009, issued Jul. 11, 1995 to Ekins discloses a method for analyzing analytes in a liquid.

U.S. Pat. No. 5,472,603 issued Dec. 5, 1995 to Schembri discloses an analytical rotor for performing fluid separations.

Anderson, 1968, *Anal Biochem.* 28: 545–562 teach a multiple cuvette rotor for cell fractionation.

Renoe et al., *Clin. Chem.* 20: 955–960 teach a "minidisc" module for a centrifugal analyzer.

Burtis et al., *Clin. Chem.* 20: 932–941 teach a method for dynamic introduction of liquids into a centrifugal analyzer.

Fritsche et al. 1975, *Clin. Biochem.* 8: 240–246 teach enzymatic analysis of blood sugar levels using a centrifugal analyzer.

Burtis et al., *Clin. Chem.* 21: 1225–1233 a multipurpose optical system for use with a centrifugal analyzer.

Hadjiioannou et al. 1976, *Clin. Chem.* 22: 802–805 teach automated enzymatic ethanol determination in biological fluids using a miniature centrifugal analyzer.

Lee et al., 1978, *Clin. Chem.* 24: 1361–1365 teach an automated blood fractionation system.

Cho et al., 1982, *Clin. Chem.* 28: 1961–1965 teach a multichannel electrochemical centrifugal analyzer.

Bertrand et al., 1982, *Clinica Chimica Acta* 119: 275–284 teach automated determination of serum 5'-nucleotidase using a centrifugal analyzer.

Schembri et al., 1992, *Clin. Chem.* 38: 1665–1670 teach a portable whole blood analyzer.

Walters et al., 1995, *Basic Medical Laboratory Technologies*, $3^{rd}$ ed., Delmar Publishers: Boston teach a variety of automated medical laboratory analytic techniques.

Recently, microanalytical devices for performing select reaction pathways have been developed.

U.S. Pat. No. 5,006,749, issued Apr. 9, 1991 to White disclose methods and apparatus for using ultrasonic energy to move microminiature elements.

U.S. Pat. No. 5,252,294, issued Oct. 12, 1993 to Kroy et al. teach a micromechanical structure for performing certain chemical microanalyses.

U.S. Pat. No. 5,304,487, issued Apr. 19, 1994 to Wilding et al. teach fluid handling on microscale analytical devices.

U.S. Pat. No. 5,368,704 issued Nov. 29, 1994 to Madou et al. teach microelectrochemical valves.

International Application, Publication No. WO93/22053, published Nov. 11, 1993 to University of Pennsylvania disclose microfabricated detection structures.

International Application, Publication No. WO93/22058, published Nov. 11, 1993 to University of Pennsylvania disclose microfabricated structures for performing polynucleotide amplification.

Columbus et al, 1987, *Clin. Chem.* 33: 1531–1537 teach fluid management of biological fluids.

Ekins et al., 1992, *Ann. Biol. Clin.* 50: 337–353 teach a multianalytical microspot immunoassay.

Wilding et al., 1994, *Clin. Chem.* 40: 43–47 disclose manipulation of fluids on straight channels micromachined into silicon.

The prior art discloses synthetic microchips for performing microanalytic and microsynthetic methods. One drawback in the prior art microanalytical methods and apparati has been the difficulty in designing systems for moving fluids on the microchips through channels and reservoirs having diameters in the 10–100 $\mu$m range. Also, the devices disclosed in the prior art have required separate data analysis and storage media to be integrated into an instrument for performing the microanalysis, thereby unnecessarily increasing the complexity of the instruments designed to use the microchips, without a concomitant increase in the flexibility or usefulness of these machines.

There remains a need for a simple, flexible, reliable, rapid and economical microanalytic and microsynthetic reaction platform for performing biological, biochemical and chemical analyses and syntheses that can move fluids within the structural components of a microsystems platform. Such a platform should be able to move nanoliter to microliter amounts of fluid, including reagents and reactants, at rapid rates to effect the proper mixing of reaction components, removal of reaction side products, and isolation of desired reaction products and intermediates. There is also a need for an instrument for manipulating the microsystem platform to effect fluid movement, thermal control, reagent mixing, reactant detection, data acquisition, data analysis and data and systems interface with a user. Such devices are needed, in alternative embodiments, that are sophisticated (for professional, e.g., hospital, use), easy to use (for consumer, e.g., at-home monitoring, uses) and portable (for field, e.g., environmental testing, use). Such devices also advantageously combine "wet" chemistry capabilities with information processing, storing and manipulating ability.

SUMMARY OF THE INVENTION

This invention provides an integrated, microanalytical/microsynthetic system for performing a wide variety of biological, biochemical and chemical analyses on a microminiature scale. The invention provides apparatus and methods for performing such microscale processes on a microplatform, whereby fluid is moved on the platform in defined channels motivated by centripetal force arising from rotation of the platform.

In one aspect of the invention is provided a microanalytic/microsynthetic system comprising a combination of two elements. The first element is a microplatform that is a rotatable structure, most preferably a disk, the disk comprising sample, inlet ports, fluid microchannels, reagent reservoirs, reaction chambers, detection chambers and sample outlet ports. The disk is rotated at speeds from about 1–30,000 rpm for generating centripetal acceleration that enables fluid movement. The disks of the invention also preferably comprise fluid inlet ports, air outlet ports and air displacement channels. The fluid inlet ports allow samples to enter the disk for processing and/or analysis. The air outlet ports and in particular the air displacement ports provide a means for fluids to displace air, thus ensuring uninhibited movement of fluids on the disk. Specific sites on the disk also preferably comprise elements that allow fluids to be analyzed, including thermal sources, light, particularly monochromatic light, sources, and acoustic sources, as well as detectors for each of these effectors. Alternatively, some or all of these elements can be contained on a second disk that is placed in optical or direct physical contact with the first.

The second element of the invention is a micromanipulation device that is a disk player/reader device that controls the function of the disk. This device comprises mechanisms and motors that enable the disk to be loaded and spun. In addition, the device provides means for a user to operate the Microsystems in the disk and access and analyze data, preferably using a keypad and computer display.

The invention provides methods and apparatus for the manipulation of samples consisting of fluids, cells and/or particles containing or comprising an analyte. The microplatform disks of the invention comprise Microsystems composed of, but no restricted to, sample input ports, microchannels, chambers, valves, heaters, chillers, electrophoretic and detection systems upon a disk. Movement of the sample is facilitated by the judicious incorporation of air holes and air displacement channels that allow air to be displaced but prevent fluid and/or particle loss upon acceleration.

A preferred embodiment of the disk of the invention incorporates micromachined mechanical, optical, and fluidic control structures (or "systems") on a substrate that is preferably made from plastic, silica, quartz, metal or ceramic. These structures are constructed on a submillimeter scale by photolithography, etching, stamping or other appropriate means.

Sample movement is controlled by centripetal or linear acceleration and the selective activation of valves on the disk.

In preferred embodiments of the invention, a section of the disk is dedicated to information processing by standard read/write digital technology. Data resulting from processing and analysis is recorded on the disk surface using digital recording means. In additional preferred embodiments, read-only memory (ROM) on the disk comprises disk information, instructions, experimental protocols, data analysis and statistical methods that can be accessed by a user operating the disk.

The process of fluid transport by centripetal acceleration and the micromanipulation device that enables such processing have a wide range of applications in the synthesis and analysis of fluids and detection of analytes comprising a fluid, particularly a biological fluid. Chemical and biochemical reactions are performed in a reaction chamber on the disk by the selective opening of contiguous reagent chambers by means of capillary, mechanical or thermal valve mechanisms. The contents of those chambers are delivered to the reaction chamber with the application of centripetal acceleration. The product of the reaction can then be used as a reagent for subsequent reactions, interrogated by detection systems or recovered.

Certain preferred embodiments of the apparatus of the invention are described in greater detail in the following sections of this application and in the drawings.

DETAILED DESCRIPTION OF PREFERRED EMBODIMENTS

Figure 1A:
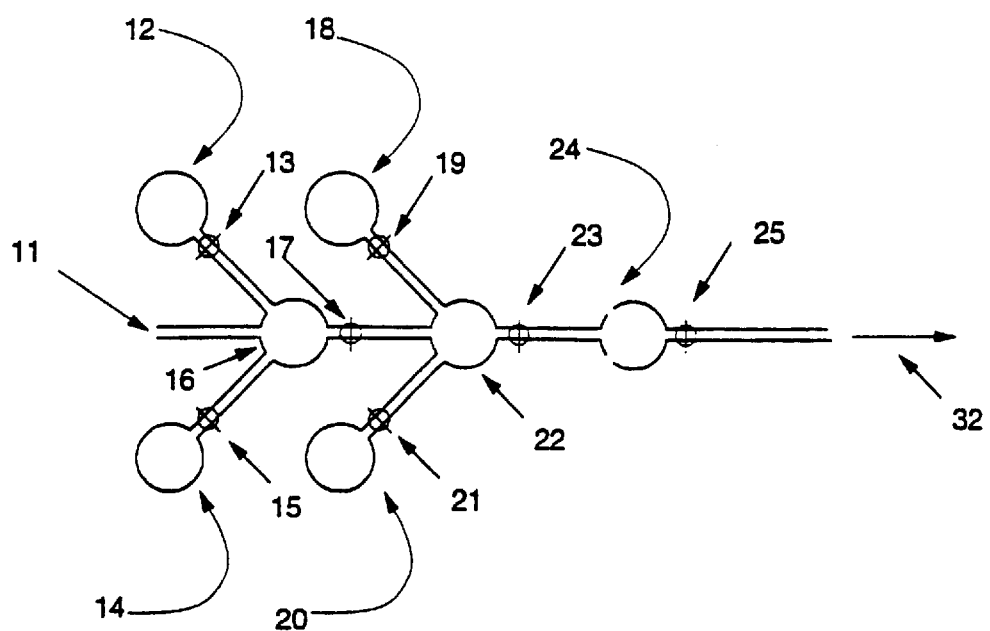
FIG. 1A (top view) and 1B (side view) illustrate the arrangement of reservoirs (12,14,18,20), valves (13,15,17,19,21,23,25) reaction chambers (16,22,24), ports (11,32) and air vents (29,33,34,35) in disks comprising the microplatforms of the invention.

This invention provides a microplatform and a micromanipulation device for performing microanalytical and microsynthetic assays of biological, chemical, environmental and industrial samples. For the purposes of this invention, the term "sample" will be understood to encompass any chemical or particulate species of interest, either isolated or detected as a constituent of a more complex mixture, or synthesized from precursor species. The invention provides a combination of a microplatform that is a rotatable, analytic/synthetic microvolume assay platform (collectively referred to herein as a "disk") and a micromanipulation device for manipulating the platform to achieve fluid movement on the platform arising from centripetal force on the platform as result of rotation. The platform of the invention is preferably and advantageously a circular disk; however, any platform capable of being rotated to impart centripetal for a fluid on the platform is intended to fall within the scope of the invention.

The microplatforms of the invention (preferably and hereinafter collectively referred to as "disks", for the purposes of this invention, the terms "microplatform", "microsystems platform" and "disk" are considered to be interchangeable), are provided to comprise one or a multiplicity of microsynthetic or microanalytic systems. Such microsynthetic or microanalytic systems in turn comprise combinations of related components as described in further detail herein that are operably interconnected to allow fluid flow between components upon rotation of the disk. These components can be fabricated as described below either integral to the disk or as modules attached to, placed upon, in contact with or embedded in the disk. The invention also comprises a micromanipulation device for manipulating the disks of the invention, wherein the disk is rotated within the device to provide centripetal force to effect fluid flow on the disk. Accordingly, the device provides means for rotating the disk at a controlled rotational velocity, for stopping and starting disk rotation, and advantageously for changing the direction of rotation of the disk. Both electromechanical means and control means, as further described herein, are provided as components of the devices of the invention. User interface means (such as a keypad and a display) are also provided.

The invention provides methods and apparatus for the manipulation of samples consisting of fluids, cells and/or particles (generically termed "sample" herein) containing an analyte of interest. The platforms of the invention consist of systems comprising sample input ports, microchannels for fluid flow, reagent reservoirs, mixing chambers, reaction chambers, optical reading chambers, valves for controlling fluid flow between components, temperature control elements, separation channels, electrophoresis channels and electrodes, air outlet ports, sample outlet ports, product outlet ports, mixing means including magnetic, acoustic and mechanical mixers, an on-board power supply such as a battery or electromagnetic generator, liquid and dry reagents, and other components as described herein or known to the skilled artisan. The movement of the sample is facilitated by the judicious incorporation of air holes or air displacement channels that allow air to be displaced but prevent fluid and/or particle loss upon acceleration. Preferably, the disk incorporates microfabricated mechanical, optical, and fluidic control components on platforms made from, for example, plastic, silica, quartz, metal or ceramic. For the purposes of this invention, the term "microfabricated" refers to processes that allow production of these structures on the sub-millimeter scale. These processes include but are not restricted to photolithography, etching, stamping and other means that are familiar to those skilled in the art.

Fluid (including reagents, samples and other liquid components) movement is controlled by centripetal acceleration due to rotation of the platform, and by the selective activation of valves controlling the connections between the components of the microsystems of the platform. The magnitude of centripetal acceleration required for fluid to flow at a rate and under a pressure appropriate for a particular microsystem is determined by factors including but not limited to the effective radius of the platform, the position angle of the structures on the platform with respect to the direction of rotation and the speed of rotation of the platform.

Chemical and biochemical reactions are performed in a reaction chamber by the selective opening of microvalves controlling access to contiguous reagent reservoirs. Microvalves as described in more detail below include mechanical, electrical and thermal valve mechanisms, as well as capillary microvalves wherein fluid flow is controlled by the relationship between capillary forces and centripetal forces acting on the fluid. The contents of the reagent reservoirs, that are connected a reaction chamber through microchannels controlled by such microvalves, are delivered to the reaction chamber by the coincident rotation of the microplatform and opening of the appropriate microvalves. The amount of reagent delivered to a reaction chamber is controlled by the speed of rotation and the time during which the valve to the reagent reservoirs is open. Products of the reaction performed in the reaction chamber are similarly removed from the reaction chamber to an analytical array, a second reaction chamber or a product outlet port by the controlled opening of microvalves in the reaction chamber.

Analytical arrays constituting components of the microplatforms of the invention include detection systems for detecting, monitoring, quantitating or analyzing reaction course, products or side-products. Detection systems useful in the fabrication and use of the microplatforms of the invention include, but are not limited to, fluorescent, chemiluminescent, calorimetric, electrochemical and radioactivity detecting means. Optionally, the detection system can be integral to the platform, comprise a component of the device manipulating the platform, or both.

Thus, the microplatform and micromanipulation device provided by the invention produce analytic or synthetic data to be processed. Data processing is accomplished either by a processor and memory module on the disk, by the device microprocessor and memory, or by an out board computer connected to the micromanipulation device. Removable media for data retrieval and storage is provided either by the disk itself or by the device, using computer diskette, tape, or optical media. Alternatively and advantageously, data is written on the microplatform using CD read/write technologies and conventional optical data storage systems In such embodiments, data is written to the microplatform on the underside of the platform, opposite to the "wet" chemistry side holding the various microsystem components disclosed herein.

The physical parameters of the microplatforms of the invention are widely variable. When provided as a disk, the disk radius ranges from 1–25 cm, and disk thickness ranges from 0.1 mm to 10 cm, more preferably 0.1 mm to 100 mm. Preferred embodiments that are most advantageous for manufacturing and operation of the disks of the invention have dimensions within one or more of four pre-existing formats: (1) 3-inch compact disk (CD), having a radius of about 3.8 cm and thickness of about 1 mm: (2) 5-inch CD, having a radius of about 6 cm and a thickness of 1 mm; (3) 8-inch CDV (commercially termed a "Laservision" disk), having a radius of 10 cm and a thickness of 2 mm; and (4) 12-inch CDV disk, having a radius of 15 cm and a thickness of 2 mm.

Microchannel and reservoir sizes are optimally determined by specific applications and by the amount of reagent and reagent delivery rates required for each particular embodiment of the microanalytic and micro synthetic methods of the invention. For microanalytical applications, for example, disk dimensions of a 5-in CD (6 cm×1 mm) are preferred, allowing reagent reservoirs to contain up to 0.5 mL (close to the actual displaced by the disk). Microchannel sizes can range from 0.1 $\mu$m to a value close to the 1 mm thickness of the disk. Microchannel and reservoir shapes can be trapezoid, circular or other geometric shapes as required. Microchannels preferably are embedded in a microsystem platform having a thickness of about 0.1 m to 100 $\mu$mm, wherein the cross-sectional dimension of the microchannels across the thickness dimension of the platform is less than 500 $\mu$m and from 1 to 90 percent of said cross-sectional dimension of the platform. Reagent reservoirs, reaction chambers, detections chambers and sample inlet and outlet ports preferably are embedded in a microsystem platform having a thickness of about 0.1 m to 100 $\mu$mm, wherein the cross-sectional dimension of the microchannels across the thickness direction of the platform is from 1 to 75 percent of said cross-sectional dimension of the platform.

Figure 1C:
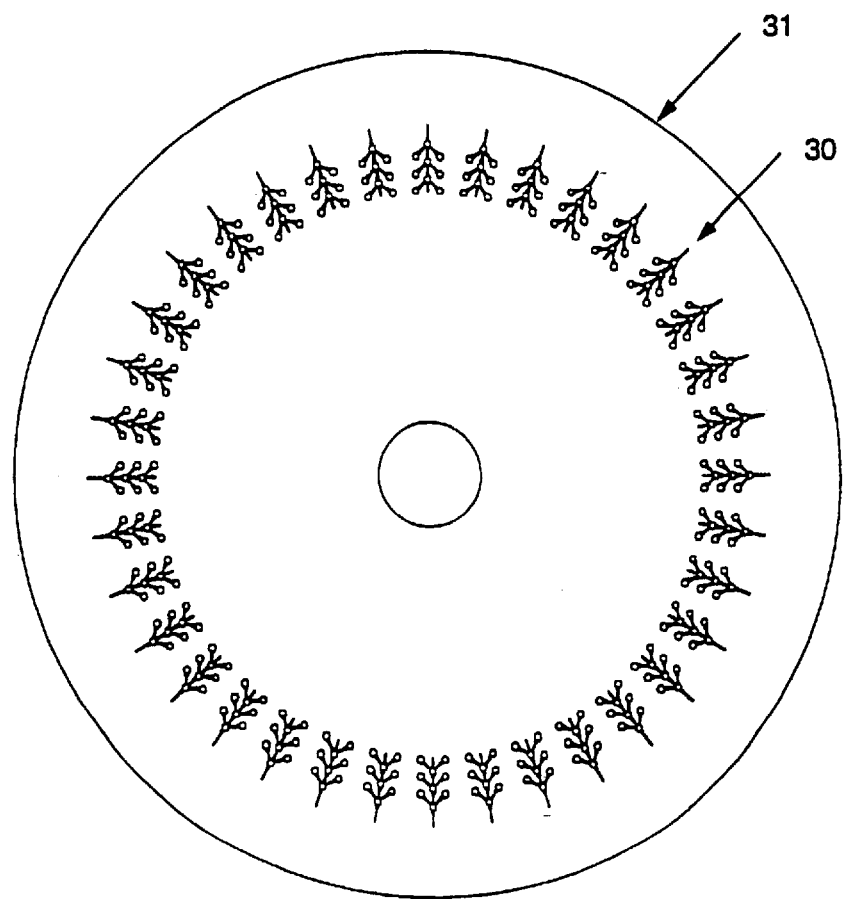
FIG. 1C shows the arrangement of a multiplicity of Microsystems on a disk.

Input and output (entry and exit) ports are components of the microplatforms of the invention that are used for the introduction of removal of a variety of fluid components. Entry ports are provided to allow samples and reagents to be placed on or injected onto the disk; these types of ports are generally located towards the center of the disk. Exit ports are provided to allow air to escape, advantageously into an on-disk "muffler" or "baffle" system, to enable uninhibited fluid movement on the disk. Also included in air handling systems on the disk are air displacement channels, whereby the movement of fluids displaces air through channels that connect to the fluid-containing microchannels retrograde to the direction of movement of the fluid, thereby providing a positive pressure to further motivate movement of the fluid. Exit ports are also provided to allow products to be removed from the disk. Port shape and design vary according specific applications. For example, sample input ports are designed, inter alia, to allow capillary action to efficiently draw the sample into the disk. In addition, ports can be configured to enable automated sample/reagent loading or product removal. Entry and exit ports are most advantageously provided in arrays, whereby multiple samples are applied to the disk using a specifically-designed administration tool. Similar tools are useful designed to effect product removal from the microplatform. Representative arrangements of sample ports, air vents, reagent reservoirs, reaction chambers and microvalves are shown in FIGS. 1A through 1C.

Operative and optimal placement of the various disk components and elements depend on the dynamics of fluid movement in relation to centripetal forces. Centripetal force is a function of platform radius, disk rotation speed and fluid density. Certain functional parameters relevant to the platform Microsystems of this invention are understood in terms of the following equations. These should represent limits of system performance, because they assume both viscous and non-viscous (turbulent) losses for fully-developed fluid flow.

The driving force for fluid motion or creating fluid pressures is the force on matter which results from centripetal acceleration. A device may rotate at an angular rate of $f$ in revolutions/sec and angular frequency $$\omega = 2\pi f \tag{1}$$

The centripetal acceleration (or acceleration oriented along the radius at a radial distance R from the center of the uniformly-rotating disk) is $$a_c \omega^2 R. \tag{2}$$

A mass m in such uniform circular motion is subject to a centripetal force $$F_c = ma_c = m\omega^2 R \tag{3}$$

which is directed inward along the radius to the center of rotation. If the mass is held fixed at this radius, the device causing rotation supplies this force; this is the origin of the static pressure in liquid columns discussed below. If the mass is placed on top of a trap-door above a radially-oriented tube, and the trap-door opened, the inertia of the mass will cause it to accelerate down the tube; this is the basis for driving fluids radially outward on a rotating disk.

Rotation may create a static pressure in a non-flowing fluid. Assume a column of liquid extending from an inner radius $R_0$. The tube may be along the radius or inclined at an angle to the radius. Let the pressure at position $R_0$ be defined as $P_0$, which is for example atmospheric pressure. The excess pressure due to rotation of the liquid at Position R such that $R_0 < R$ is found by integrating the centripetal force per unit area for liquid of density p from position $R_0$ to R:

$$P - P_0 = \int \rho a_c = \rho \omega^2 / 2 \times (R^2 - R_0^2) \tag{4}$$

If the tube is filled, extending from the center, then this pressure is $$P - P_0 = (2.834 \times 10^{-4}) \rho f^2 R^2 \tag{5}$$

in pounds per square inch (psi) where R=radial position in cm, $\rho$=density in gm/cm$^3$, and f=frequency in revolutions/sec. Thus, the pressure (or the amount of centripetal force on a fluid) varies directly with the density of the fluid, and as the square of the radial position from the center of rotation as well as the square of the frequency of rotation.

To determine the velocity of liquid in motion in channels on a rotating disk, the equation of motion for the fluid must be solved. An element of fluid of radius a and length dR filling the circular channel has a mass dm subject to acceleration:

$$dm = \pi \rho a^2 dr \tag{6}$$

The equation of motion for this fluid element is force= (mass) X (acceleration). The forces are centripetal forces, capillary forces due to differences in interfacial energies between the fluid and vapor and fluid and solid surfaces, and dissipative forces due to the viscosity of the liquid and nonuniformity of flow. Capillary forces are ignored; it is understood that centripetal force and/or external pressure may need to be applied to force liquid into channels which are not wetted. As an over-estimate of these dissipative forces, both the force for fully-developed laminar flow of a Newtonian fluid ($F_L$) and that due to non-uniform flow ($F_D$) are included:

$$F = ma$$

$$F_c + F_L + F_D = dma_R$$

$$F_c + F_L + F_D = (\rho \pi a^2 dR) a_R \tag{7}$$

where $a_R$ is the acceleration of the fluid mass element along the radius and $$F_c = (\rho \pi a^2 dR) \omega^2 R$$

$$F_L = -(8\mu \pi a^2 dR) u$$

$$F_D = -(2\rho \pi a^2 dR) u^2 \tag{8}$$

where $\mu$ is the viscosity and u is the radial velocity of the fluid. These last two expressions are standard-mechanics expressions for fully-developed and completely undeveloped laminar flow, such as at channel entrances/exits or at the ends of a flowing droplet. Also note that for tubes or channels inclined at an angle $\theta$ with respect to the radius $F_C$ would be replaced by $(F_C) \times \cos \theta$. The final equation becomes $$(\rho \pi a^2 dR)\omega^2 R - (8\mu \pi dR)u - (2\rho \pi a^2 u^2 dR) = (\rho \pi a^2 dR)(du/dt) \tag{9}$$

where the radial acceleration of the fluid is defined by $a_R - (du/dt)$. This is a differential equation for the fluid flow velocity.

This equation is solved for specific examples. Consider a droplet of fluid of length L moving in a radial channel of greater length than the droplet.

Because the fluid in the droplet all moves at the same velocity, dR may be replaced by L and R by the average position of the droplet, $<R> = (R+L/2)$.
Dividing out common factors:

$$(\omega^2(R+L/2)/2) - (8\mu/\rho a^2)u - 2(u^2/L) = (du/dt) \tag{10}$$

This equation must be solved numerically. An approximation may be made which has been justified through comparison with numerical solutions. It consists of this: the negative terms on the left-hand-side almost entirely cancel the positive term. Then the right-hand-side can be set to 0 and a solution can be made to the resultant equation for the "terminal velocity" at position R, $u_0$ $$(\omega^2(R+L/2)/2) - (8\mu/\rho a^2)u_0 - 2(u_0^2/L) = 0 \tag{11}$$

This is a quadratic equation which has the solution $$u_0 = -(B + \sqrt{B^2 + 4AC})/2A \tag{12}$$

with $$A = L/2$$

$$B = 8\mu/\rho a^2$$

$$C = (\omega^2(R+L/2)/2) \quad (13)$$

In conventional units these become $A=2/L$, $B=320\mu/\rho D^2$ and $C=(19.74)f^2(2R+L)$ with $u_0$=fluid velocity in cm/sec; L=droplet length in cm; $\mu$=viscosity in poise; $\rho$=fluid density in gm/cm$^3$; D=2a=tube diameter in cm; and R=radial position of the fluid droplet in cm. As described, this expression gives the approximate velocity of a droplet of fluid in a tubular channel, the volume of the droplet resulting in droplet length being shorter than the channel length. This estimate assumes both viscous and non-viscous losses. The velocity of a fluid droplet will increase with increasing density and droplet volume (length), and decrease with increased viscosity. The velocity will increase with increased channel diameter, rotational velocity, and radial position.

Fluid flow velocity in a filled channel connecting a full chamber at position R, and receiving reservoir at position $R_1$ is calculated by defining L in equation (11) and subsequent equations as the channel length, $L=R_1-R_0$ Then equation (13) with the definitions following equation (13) are used to calculate the flow velocity in the filled chamber as a function of radius.

The rate of fluid-flow is the product of velocity and channel area:

$$Q = u_0 \pi a^2 = u_0 \pi D^2/4 \quad (14)$$

where Q=flow in mL/sec; $u_0$=velocity in cm/sec (calculated from equations 12 and 13); and D=tube diameter in cm.

The time required to transfer a volume V from a reservoir to a receptacle through a tube or channel of length L depends on whether V is such that the tube is filled (length of a "droplet" of volume V in the tube would be longer than the tube itself) or unfilled by volume V. In the former case, this time is approximately the volume V of the fluid divided by the rate of flow Q; in the latter case it is approximately this calculated time multiplied by the ratio of the tube length to the resultant droplet length:

$$Dt = V/Q, \text{ if } L \leq (4V/\pi D^2)$$

$$Dt = (V/Q) \times (4\pi D^2 L/4V), \text{ if } L > (4V/\rho D^2) \quad (15)$$

wherein Dt is the same time in seconds for fluid of volume V in mL flowing at rate Q in mL/sec to flow from a filled reservoir to a receptacle through a tube of length L and diameter D in cm. The rate of flow Q is calculated from eq. (14) and by extension equations (12) and (13) and the definitions of the parameters following equation (13). The time Dt increases with increasing volume transferred and decreases with increasing flow-rate.

Fluid characteristics such as pressure and velocity are related to physical parameters of the disk, such as disk radius and speed of rotation, as described above. These relationships are illustrated in FIGS. 2–5, derived from the above equations for water at room temperature, with $p=1$ gm/cm$^3$ and $\mu=0.001$ poise. These figures delineate the most relevant parameters of fluid movement on a rotating disk.

Figure 2A:
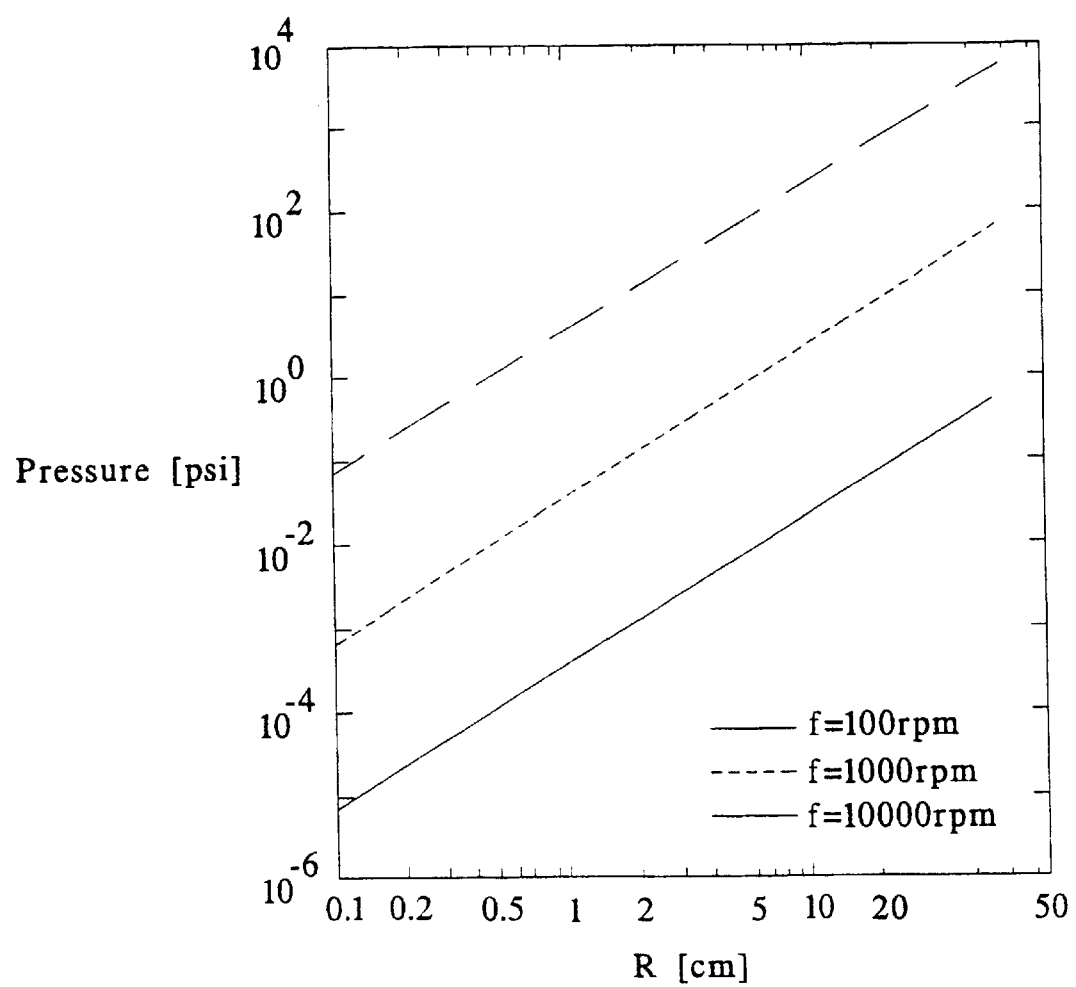
FIG. 2A is a graph and FIG. 2B is a schematic diagram of the arrangement of a channel on a disk of the invention as described with relation to Equation 5.
Figure 2B:
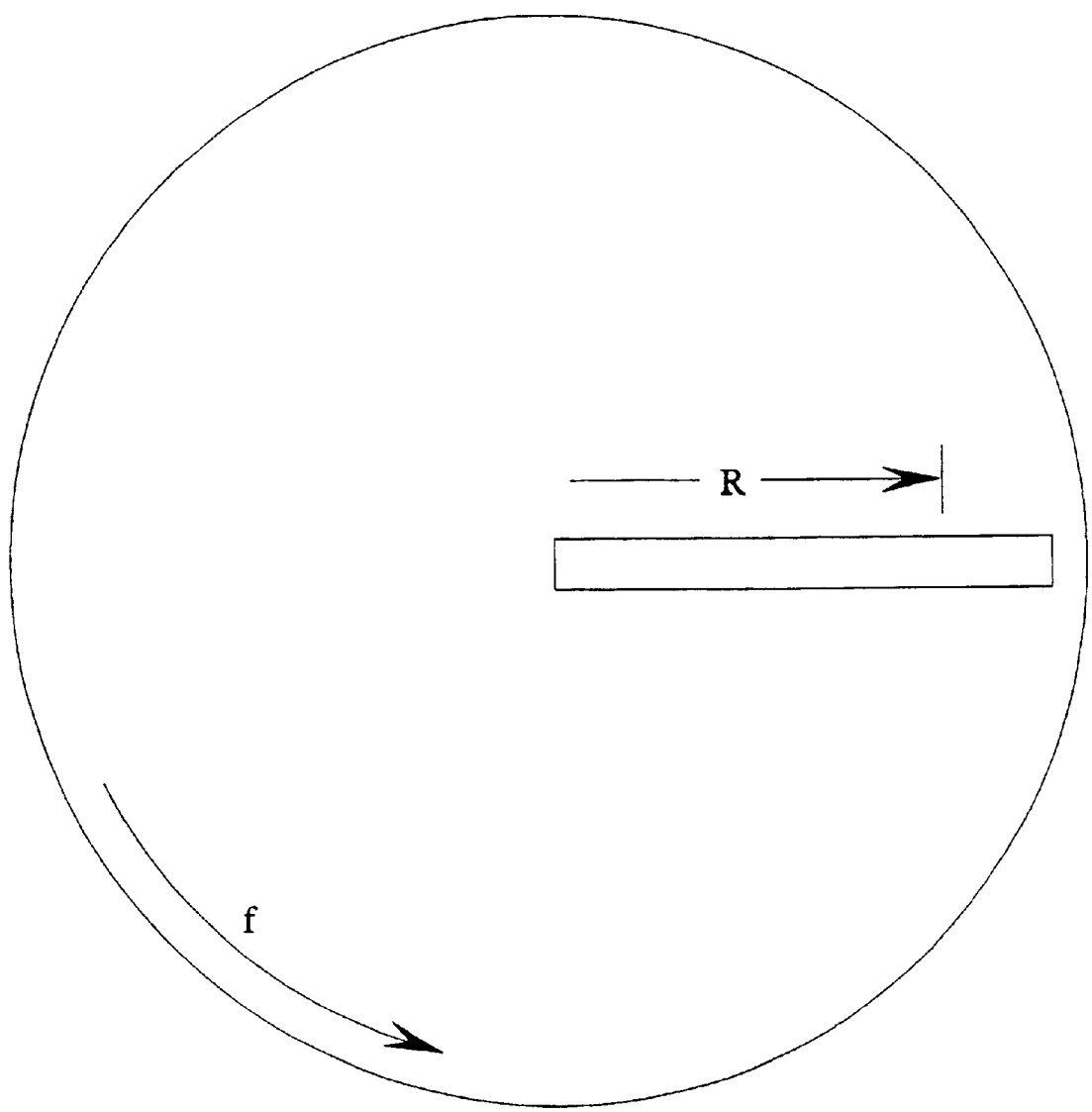

FIG. 2A illustrates the relationship between static pressure in a fluid-filled tube 30 cm in length as a function of radial distance®) and rotation rate (f), calculated from Equation 5. The arrangement of the tube on a rotating disk is shown in FIG. 2B. It can be seen that pressures of between 0 and 10,000 psi can be generated in the tube at rotational speeds of 0 to 10,000 rpm. Pressures of this magnitude are conventionally used, for example, to drive high pressure liquid chromatography (HPLC).

Figure 3A:
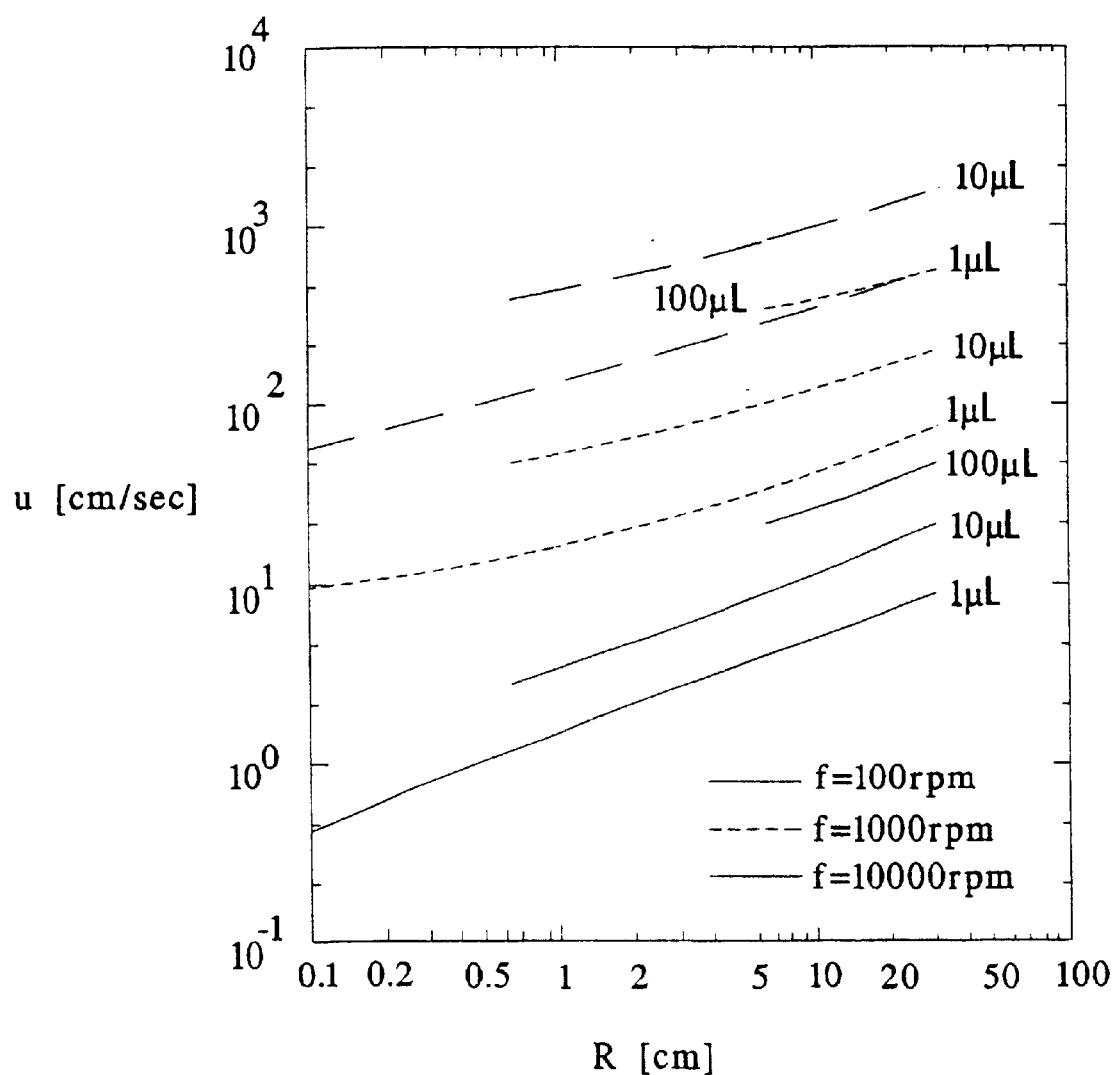
FIG. 3A is a graph and FIG. 3B is a schematic diagram of the arrangement of a channel on a disk of the invention as described with relation to Equations 12 and 13.
Figure 3B:
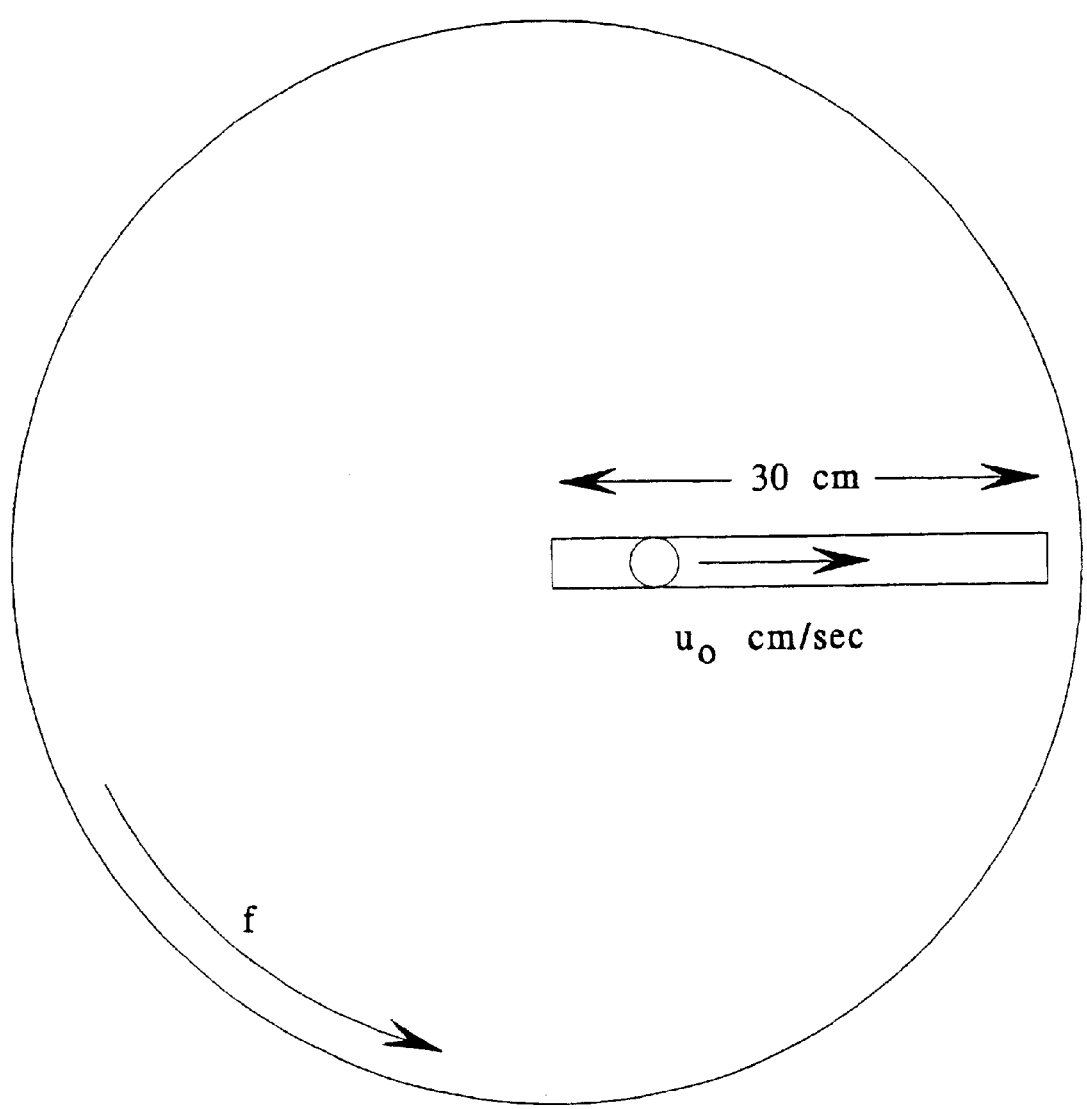
Figure 4A:
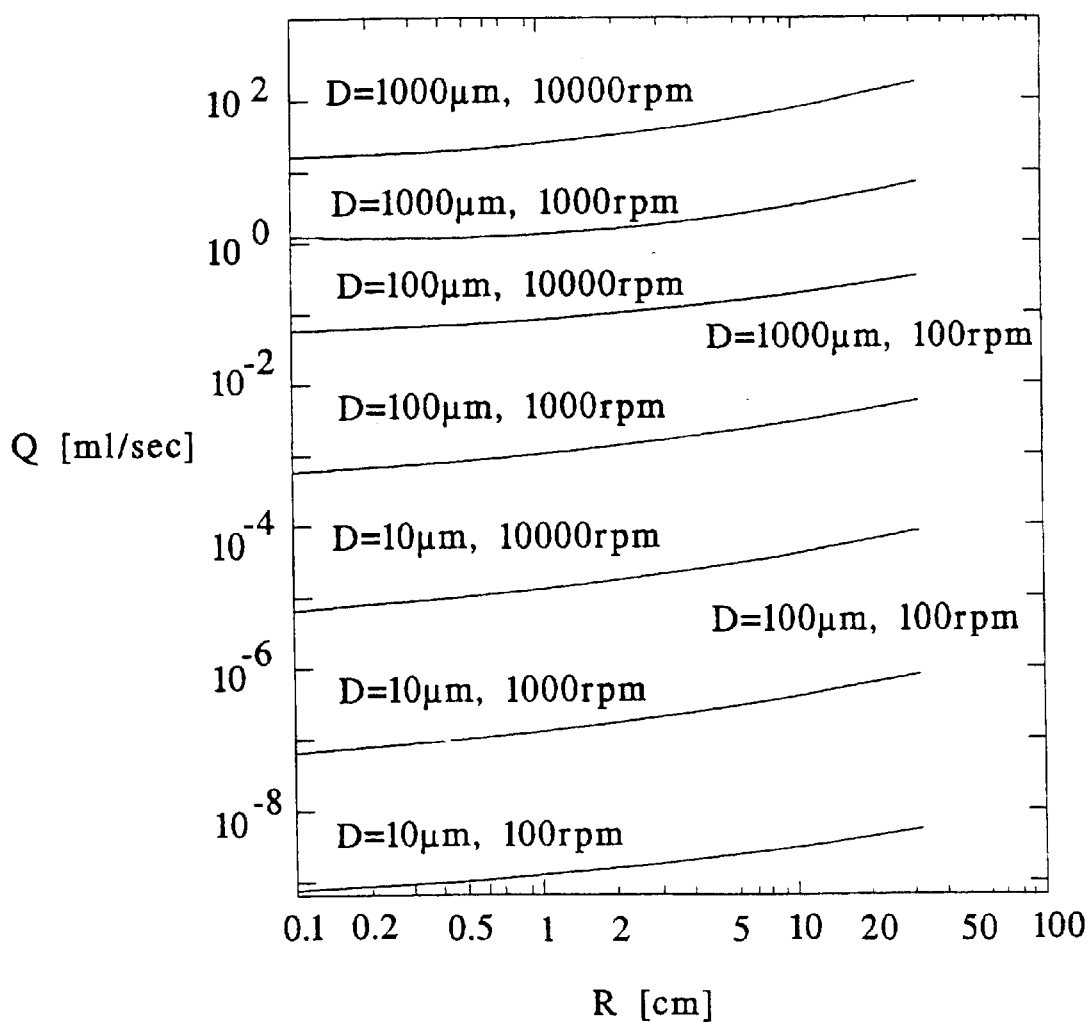
FIG. 4A is a graph and FIG. 4B is a schematic diagram of the arrangement of a channel on a disk of the invention as described with relation to Equation 14.
Figure 4B:
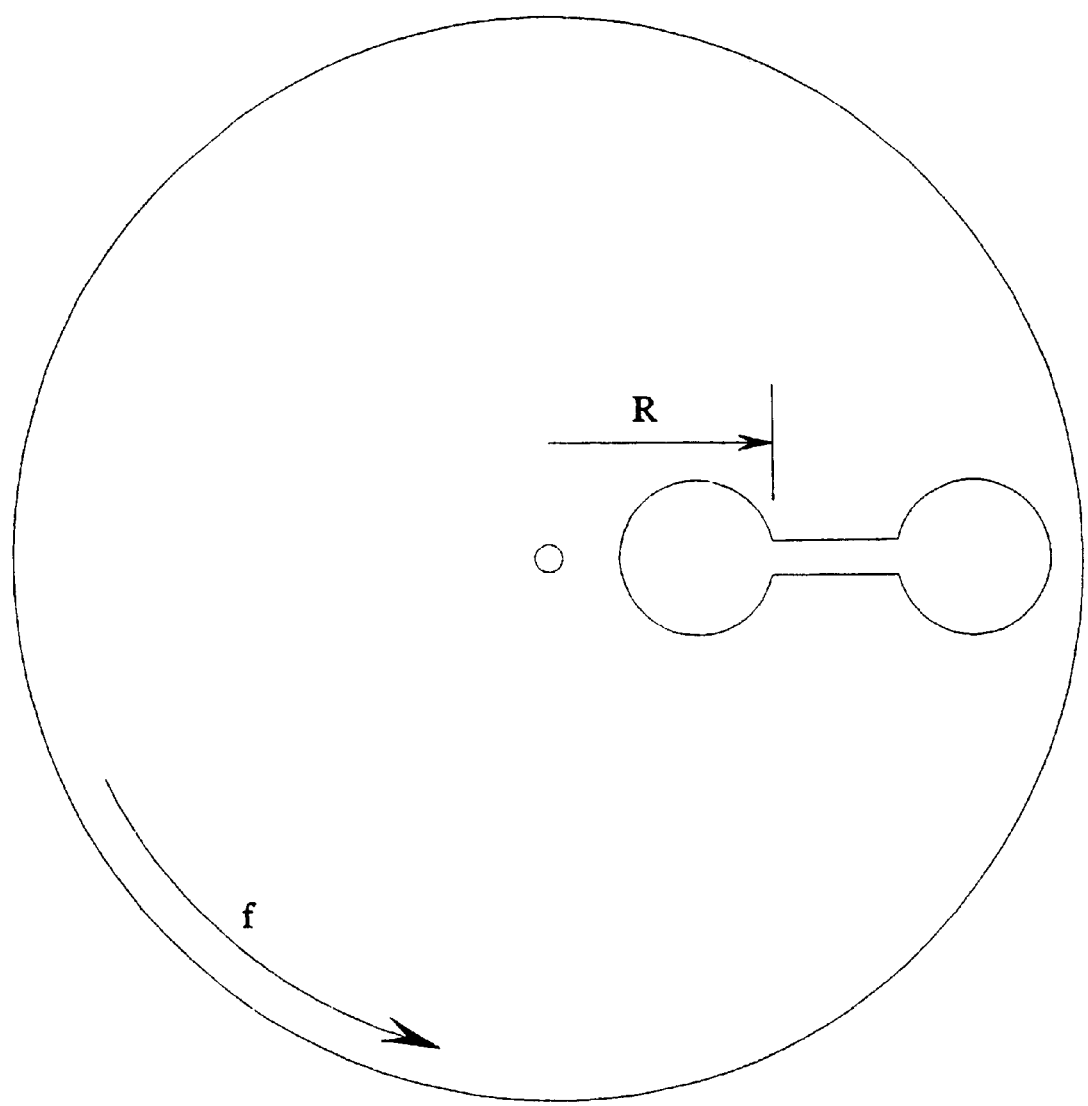

FIG. 3A shows the radial velocity of droplets having volume of 1, 10 and 100 $\mu$L droplets moving in an empty, 30 cm long tube with a diameter of 1 mm, calculated from Equations 12 and 13. The rube is aligned to extend along the radius of the disk from the center, and the disk is rotated at speeds of 100, 1,000 or 10,000 rpm. The arrangement of the tube on a rotating disk is shown in FIG. 3B. These velocities may be used to calculate the transfer time for fluid droplets. For example, a 1 $\mu$L droplet flows at approximately 20 cm/sec when at a position 2 cm from the center of a disk rotating at 1,000 rpm. Hence, the time to flow through a 1 cm tube can be calculated to be about 0.05 seconds. (For tubes oriented non-radially at an angle of 450 to the direction of rotation, the velocity drops by a factor of 30%.) FIG. 4A illustrates flow rates in a 5 cm fluid-filled tube of different diameters. The tubes are each placed on a rotating disk and connects two radially oriented reservoirs, shown in FIG. 4B. According to Equation 14, flow rates are a function of radial position of the tube (which vary in this example from 2–30 cm), the tube diameter (10 $\mu$m, 100 $\mu$m, or 1,00 $\mu$m), and rotation frequency (100, 1,000 or 10,000 rpm). (As above, for tubes with a non-radial orientation of 45°, the velocity drops by a factor of 30%). Droplet velocities shown in FIG. 3A were calculated by Equation 3 and flow rates determined using Equation 4.

Figure 5A:
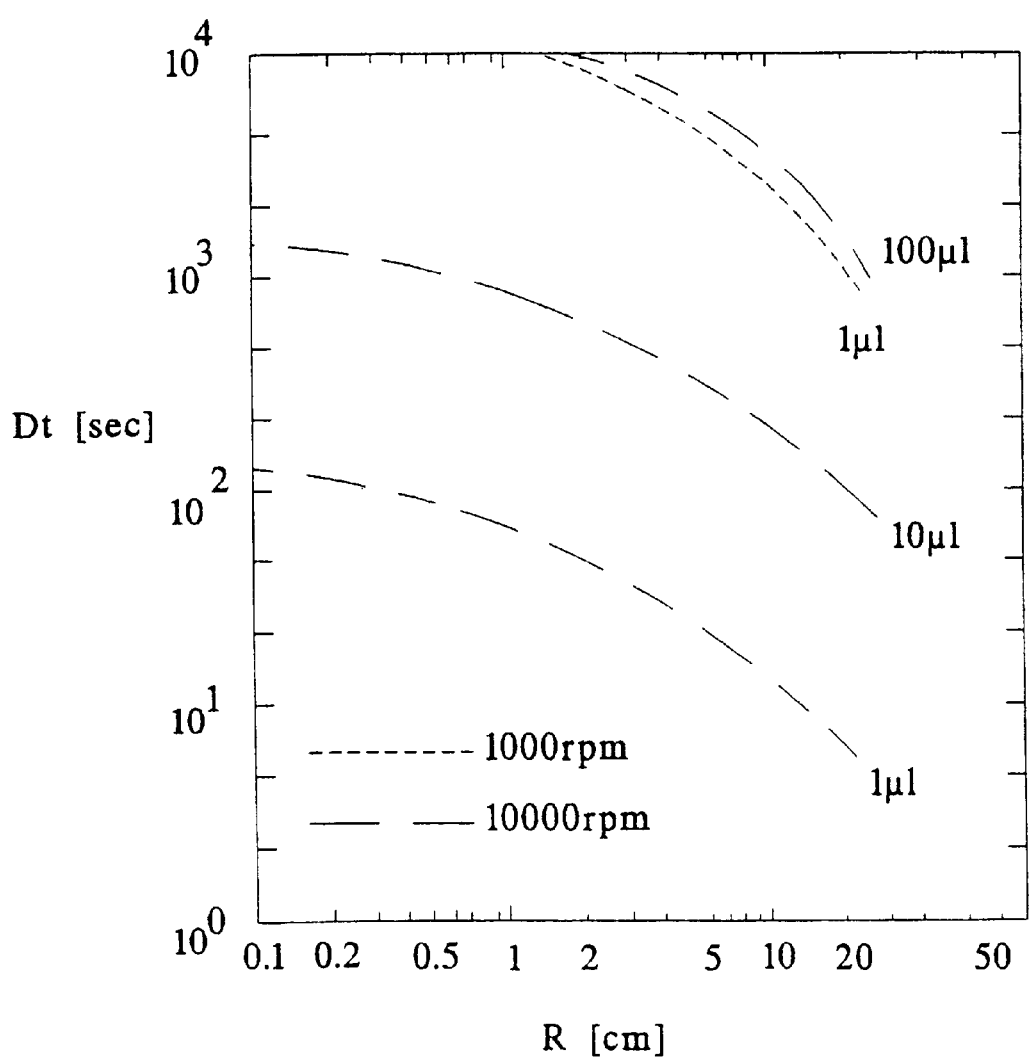
FIGS. 5A, 5B and 5C are graphs
Figure 5B:
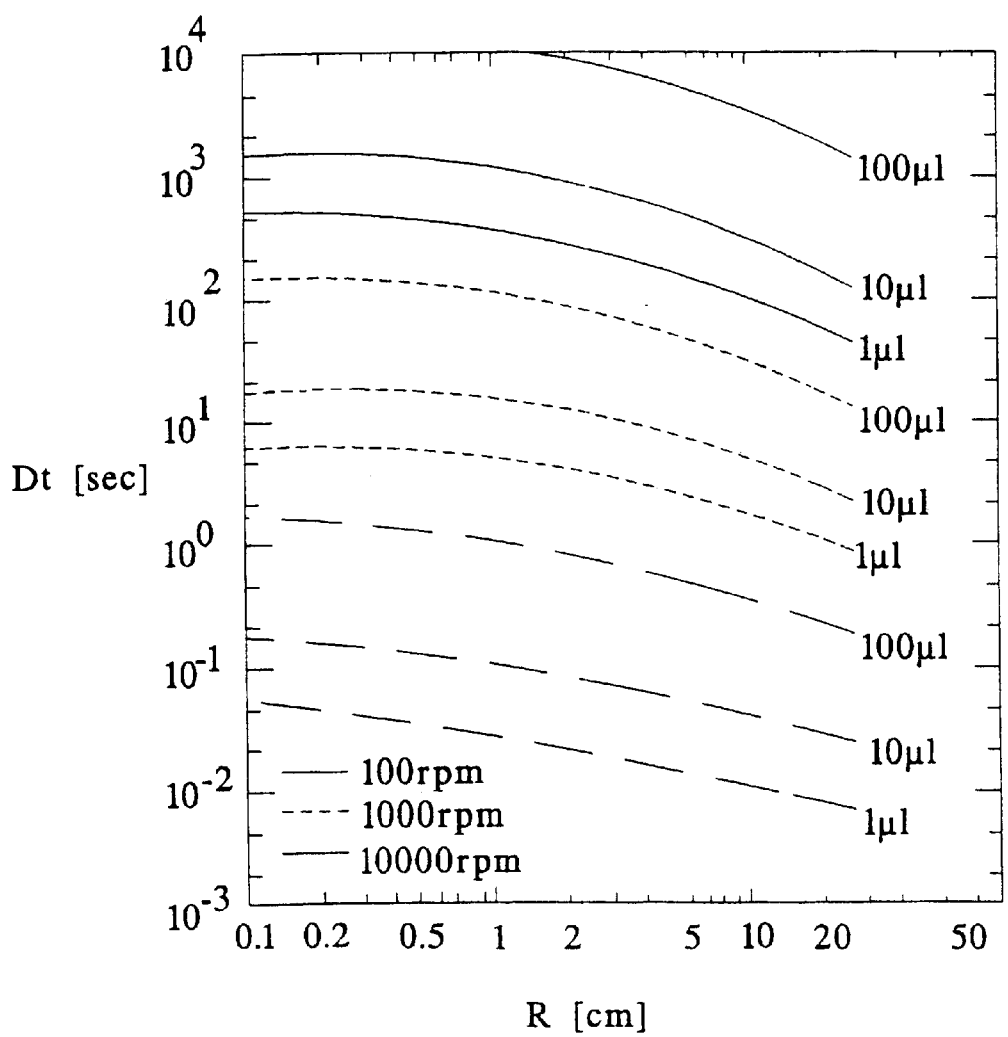
Figure 5C:
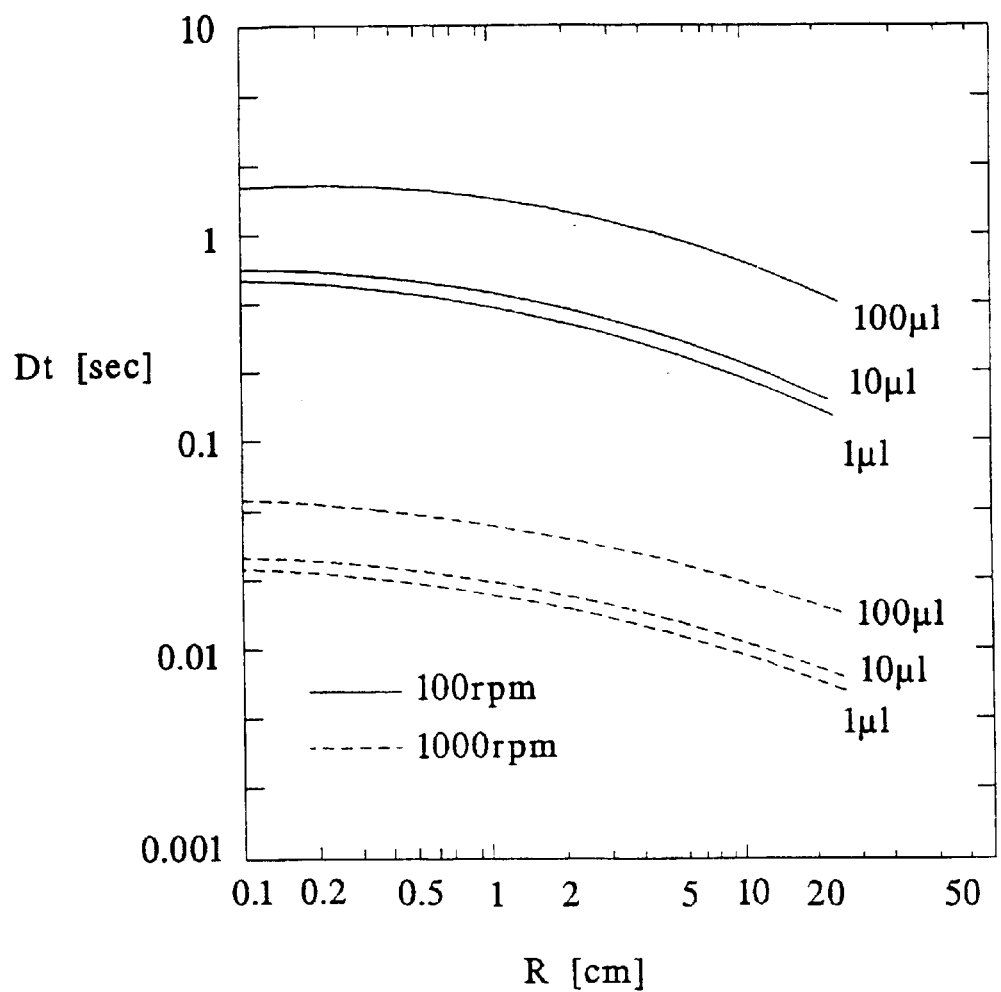
Figure 5D:
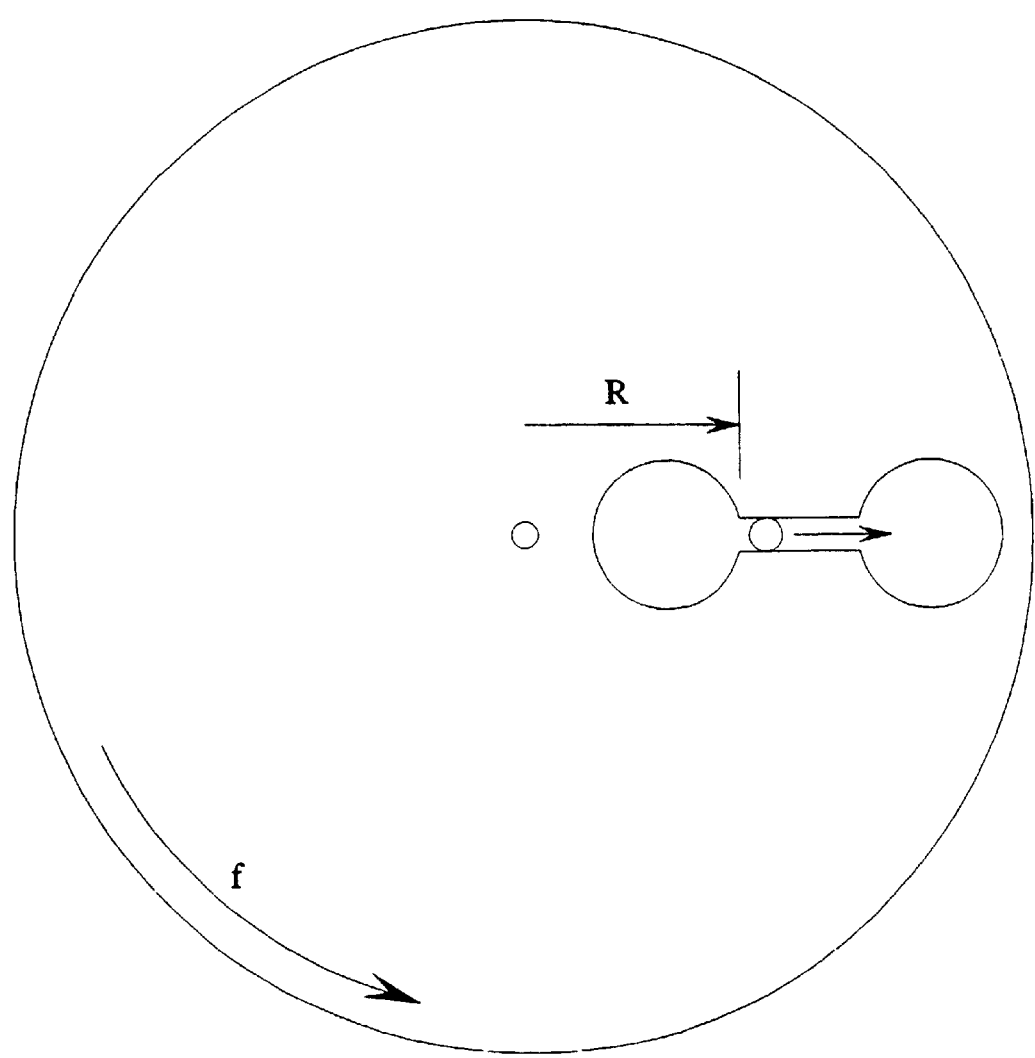
FIG. 5D is a schematic diagram of the arrangement of a channel on a disk of the invention as described with relation to Equation 15.

In FIGS. 5A, 5B and 5C, the time required to transfer 1, 10, and 100 $\mu$L droplets, respectively, through a 5 cm tube is shown. The tube connects two radially oriented reservoirs as illustrated in FIG. 5D. Transfer times are a function of radial position of the tube (o–30 cm), tube diameter (10 $\mu$m, 100 $\mu$m, or 1,000 $\mu$m), and rotation frequency (100, 1,000 or 10,000 rpm). The curves shown in FIGS. 5A, 5B and 5C were calculated using Equation 15.

Taken together, these formulae and graphs describe the interrelationship of disk radii and rotation speeds, channel lengths and diameters, and fluid properties such as viscosity and density in determining fluid velocities and flow rates on the disk. The assumptions behind these derivations include viscous losses due to Poiseuille (non-turbulent) flow, with the addition of losses due to non-uniform flow of droplets and at tube inlet and outlet ports. These formulae and graphs provide lower limits for velocities and flow rates. Fluid velocities can range from less than 1 cm/sec to more than 1,000 cm/sec, and fluid flow rates from less than 1 pL/sec to tens of mL/sec for rotation rates ranging from 1 to 30,000 rpm. By combining channel diameters and positions on the disk, it is possible to carry out fluid transfer over a wide range of time scales, from milliseconds to hours and tens of hours for various processes.

Disk Coatings and Composition

Microplatforms such as disks and the components comprising such platforms are advantageously provided having a variety of composition and surface coatings appropriate for a particular application among the wide range of applications disclosed herein. Disk composition will be a function of structural requirements, manufacturing processes, and reagent compatibility/chemical resistance properties. Specifically, disks are provided that are made from inorganic crystalline or amorphous materials, e.g. silicon, silica, quartz, metals, or from organic materials such as plastics, for example, poly(methyl methacrylate) (PMMA), acetonitrile-butadiene-styrene (ABS), polycarbonate, polyethylene, polystyrene, polyolefins, polypropylene and metallocene.

These may be used with unmodified or modified surfaces as described below.

One important structural consideration in the fabrication of the microsystems disks of the invention is mechanical failure due to stress during use. Failure mechanisms for disks rotated at high velocities include fracture, which can arise as the result of tensile loading, or due to cracking and crazing, as described on Hertzberg (1989, *Deformation and Fracture Mechanics of Engineering Materials*, 3$^{rd}$ edition, Wiley & Sons: New York). These failures occur when the stress (defined as the load per unit area) due to rotation of the disk exceeds a critical value characteristic of the material used to make the disk. The "load" at any point in the disk is the force of tension due to rotation; i.e., at a given radius on the disk, the overall load is the centripetal force necessary to keep the material at larger radii moving circularly; the load/area or stress is then this force divided by the total area of the disk ($2\rho r \times$ the thickness of the disk). The critical value of stress at which a material will fail is termed the yield stress, and it depends on the cohesive energy binding the material together and the presence of defects in the material (such as crystalline defects in silicon or plastic substrate material). A defect-free material can be torn apart, whereas small defects will propagate through cracking or "crazing" (i.e., plastic deformation and failure of a formerly glassy plastic). For example, the yield strength of commercial silicon permits a 30 cm disk to be spun at 10,000 rpm without mechanical failure when the diameter of internal channels and chambers is less than approximately 80% of the total thickness of the disk. In disks made of plastics, stresses on the disk are reduced in general due to the lower density of the plastic (which reduces the load/unit area). However, the yield strengths are also smaller by about two orders of magnitude than in silicon (as described in greater detail in Luis & Yannis, 1992, *Computational Modeling of Polymers*, (Bureitz, ed.), Marcel Dekker: New York). One solution to this problem is provided either by spinning a plastic 30 cm disk at a slower speed (such as 1,000 rpm), or increasing the size of the disk radius (such as using a 4 cm plastic disk for applications requiring 10,000 rpm rotation speeds). Thus, material choice specific for a particular application is sufficient to accommodate disk composition-related constraints on disk functional properties and characteristics.

Disk material in contact with fluids must also be resistant to degradation by reagent solutions (such as acetonitrile, polyacrylamide, high- or low-pH buffers) under rotational stress, upon heating and cooling, and in response to illumination with high-intensity ultraviolet or visible light (occurring, inter alia, with the use of certain detection means as described below). In addition, the surfaces presented to reagents and reaction mixtures (such as microchannels, reservoirs and reaction chambers) must have desirable surface properties appropriate for each application. Silicon, silica, and quartz are especially robust materials as substrates for microplatform fabrication. Silicon and its oxides (essentially silica) are chemically attacked only by some peroxides (such as a mixture of hydrogen peroxide plus sulfuric acid), hydroxides (such as KOH), hydrofluoric acid (HF), either alone or in combination with alkali-based nitrates, and various perfluorinated solvents (like $SF_6$) see Iler, 1979, *The Chemistry of Silica*, Wiley & Sons: New York; *Properties of Silicon*, Xth ed., INSPEC:, London, 1988). Silicon-based substrates are chemically inert to aliphatic and aromatic hydrocarbons (such as tetrahydrofuran, toluene, and the like), and are substantially inert when exposed to water and neutral aqueous solutions.

A wide variety of polymer-based (plastics) substrates are suitable for fabricating Microsystems platforms of the invention. The most chemically-resistant polymer, poly (tetrafluoroethylene; PTFE), is not melt-processible but may be easily machined. PTFE is virtually chemically inert and can be used in most applications utilizing strong acids, bases, alkalis, halogenated solvents, or other strong chemical reagents. Other fluoropolymers (such as FEP, PFA) are more easily processed than PTFE and retain most of PTFE's chemical resistance. More easily-processed materials may be chosen for selective resistance: for example, although polyimides are highly resistant to alcohols, alkalis, aliphatic hydrocarbons, and bases (e.g., NaOH), their resistance to partially-halogenated solvents (e.g. dichlorobenzene) is poor. Poly (vinyl chloride) is strongly resistant to oxidizing acids and aliphatic hydrocarbons, while its resistance to aromatic compounds is poor. In addition, many materials that are not highly-resistant to concentrated applications of certain chemicals provide sufficient resistance to dilute solutions or provide sufficient resistance for single-use devices (e.g., polyamides and polyimides may be used with dilute solutions of certain acids such as acetic acid and hydrochloric acid). Most polymeric materials are resistant to water.

Specific chemical/polymer combinations include: formamide, lutidine, and acetonitrile with non-aromatic, non-polar polymers (polypropylene, polyethylene); dichloromethane with polycarbonates and aromatic polymers (polystyrene); ethanolamine and dimethyl sulfoxide with aliphatic and non-aromatic polymers (poly(methyl methacrylates), polyimides, polyamides). Fluoropolymers are resistant to all of the above chemical agents. Other solvents and reagents of interest, including pyridine, tetrazole, trichloracetic acid, iodine, acetic anhydride, -methylpyrrolidine, N,N-diethylpropylethylamine and piperidine, are suitable for use with fluoropolymers and some solvent resistant polymers such as PVC (*Encyclopedia of Polymer Science and Technology*, 2$^{nd}$ ed., v. 3, pp 421–430, X ed., John Wiley & Sons, New York, 1989). A small set of such materials provides sufficient flexibility for virtually any application.

The surface properties of these materials may be modified for specific applications. For example, appropriate surface-modification can either encourage or suppress cell and/or protein absorption. Surface modification can be achieved by silanization, ion implantation and chemical treatment with inert-gas plasmas (i.e., gases through which electrical currents are passed to create ionization). A strong correlation has been established between water contact angle and cell adsorption, with hydrophilic surfaces showing significantly less cell adsorption than hydrophobic surfaces (see Ikada, 1994, *Biomaterials* 15: 725). Silicon, silica, and quartz present and inherently high-energy, hydrophilic surface. Alteration of surface properties is attained through hydroxylation (achieved by NaOH treatment at high temperatures) or silanization. Silanes and siloxanes are particularly appropriate for increasing the hydrophilicity of an otherwise hydrophobic surface. These compounds consist of one or several reactive head-groups which bond (chemically or through hydrogen-bonding) to a substrate, for example, a core region of alkane (—$CH_2O$—). These compounds also provide a route for more sophisticated alteration of surface properties (such as derivation with functional groups to obtain the surface properties of interest). A wide variety of such functionalities can be introduced at a surface, including vinyl, phenyl, methylene and methoxy groups, as well as surfaces providing mixed functionalities. These functional groups not only change gross properties like liquid contact angle, but provide sites for preferential adsorption of molecules, either per se or as a result of further conjugation of specific binding moieties such as peptides, antibodies or the like. Silation is most often accomplished through immersion in aqueous solution at slightly-elevated temperatures. The chemical resistance of silane and siloxane coatings is determined by the nature of bonding within the chemisorbed molecule (Arkles, 1977, *Chemtech* 7: 125). It should be noted that such properties as hydrophobicity are maintained for significant periods when organosilanes are in contact with quite corrosive acids, implying that single-use or limited-use applications in these environments are possible.

Plastic-based disk can also be readily treated to achieve the required surface properties. Inert-gas or reactive-gas plasmas are commonly used to alter surface energies through the formation of surface complexes, for example, hydroxyl-rich surfaces for increased hydrophilicity, or perfluorinated surfaces for increased hydrophobicity. Surface graft polymerization is a technique used to graft polymers or oligomers with the desired surface properties to a substrate polymer chosen for its bulk processability and manufacturing properties, such as a plastic. Commercial methods for initiating graft polymerization include gamma radiation, laser radiation, thermal or mechanical processing, photochemical processes, plasma, and wet chemical processes (further discussed in *Encyclopedia of Polymer Science and Technology*, $2^{nd}$ ed., (Supplement), Wiley & Sons: New York, 1989, pp 675–689). Chemical modification of polymer surfaces (and appropriate polymers) includes oxidations (polyethylenes), reductions (fluoropolymers), sulfonations, dehydrohalogenations (dehydrofluorination of poly (vinylidene fluoride), and hydrolyses. While the chemical nature of the surface is altered through chemical modification, mechanical properties, durability and chemical resistance are primarily a function of the substrate plastic. For example, surface grafting of poly(ethylene glycol) (PEG) onto polyethylene yields a surface that is both hydrophilic (unlike polyethylene) and resistant to water (PEG is itself soluble in water, while polyethylene is not). Finally, silation of organic polymer surfaces can also be performed, providing a wide variety of surface energy/chemistry combinations.

Figure 17A:
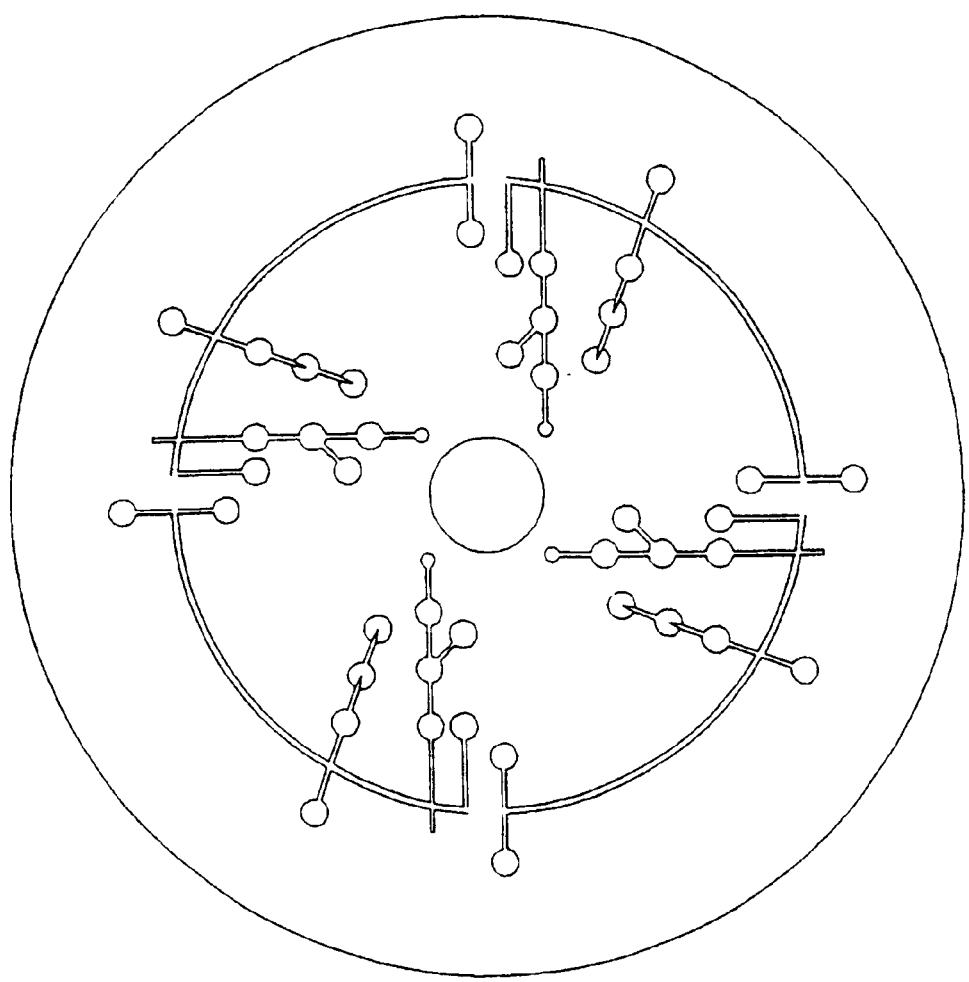
FIGS. 17A through 17E are schematic diagrams of the different structural and functional layers of a disk of the invention configured for DNA sequencing.
Figure 17B:
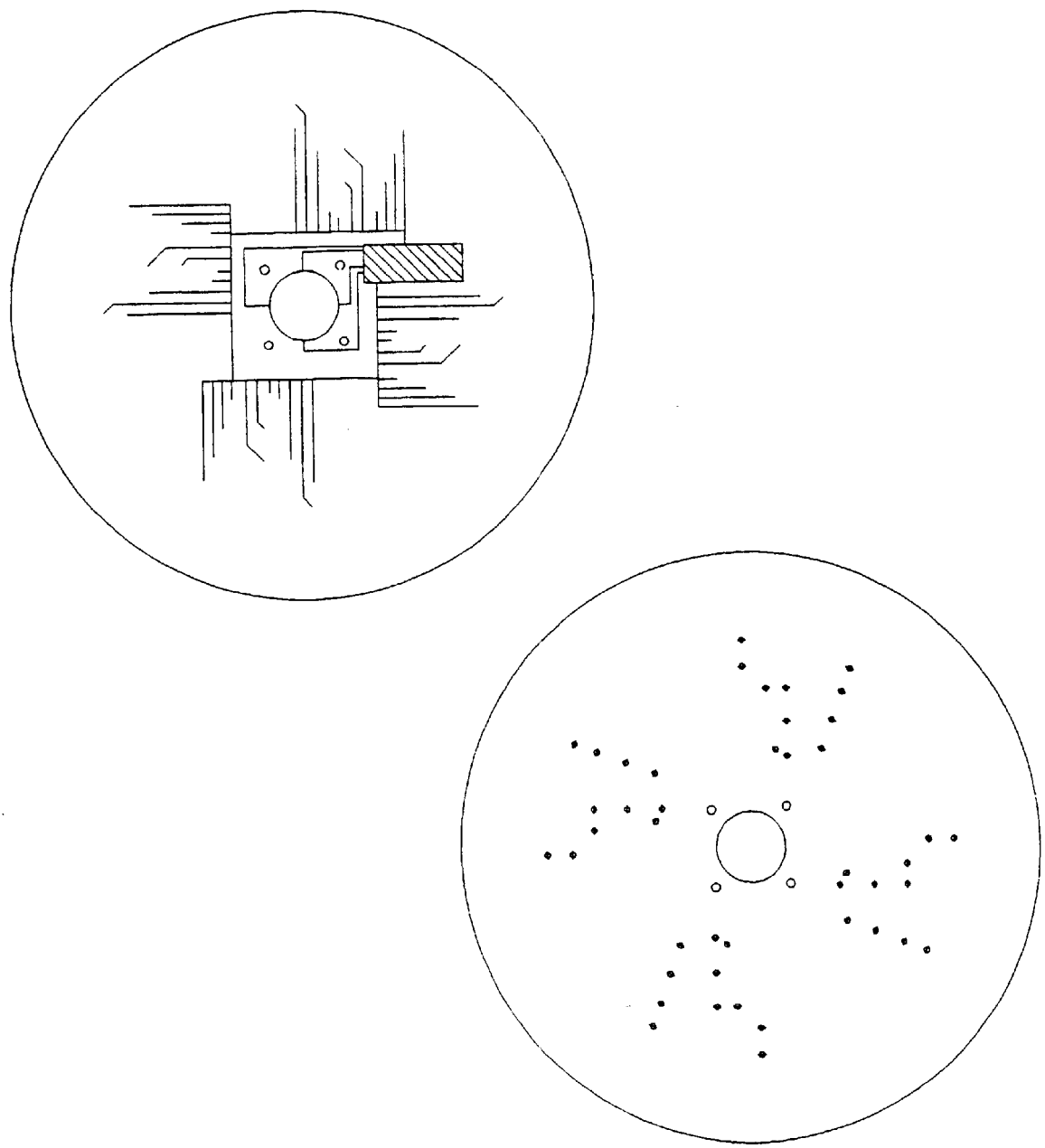
Figure 17C:
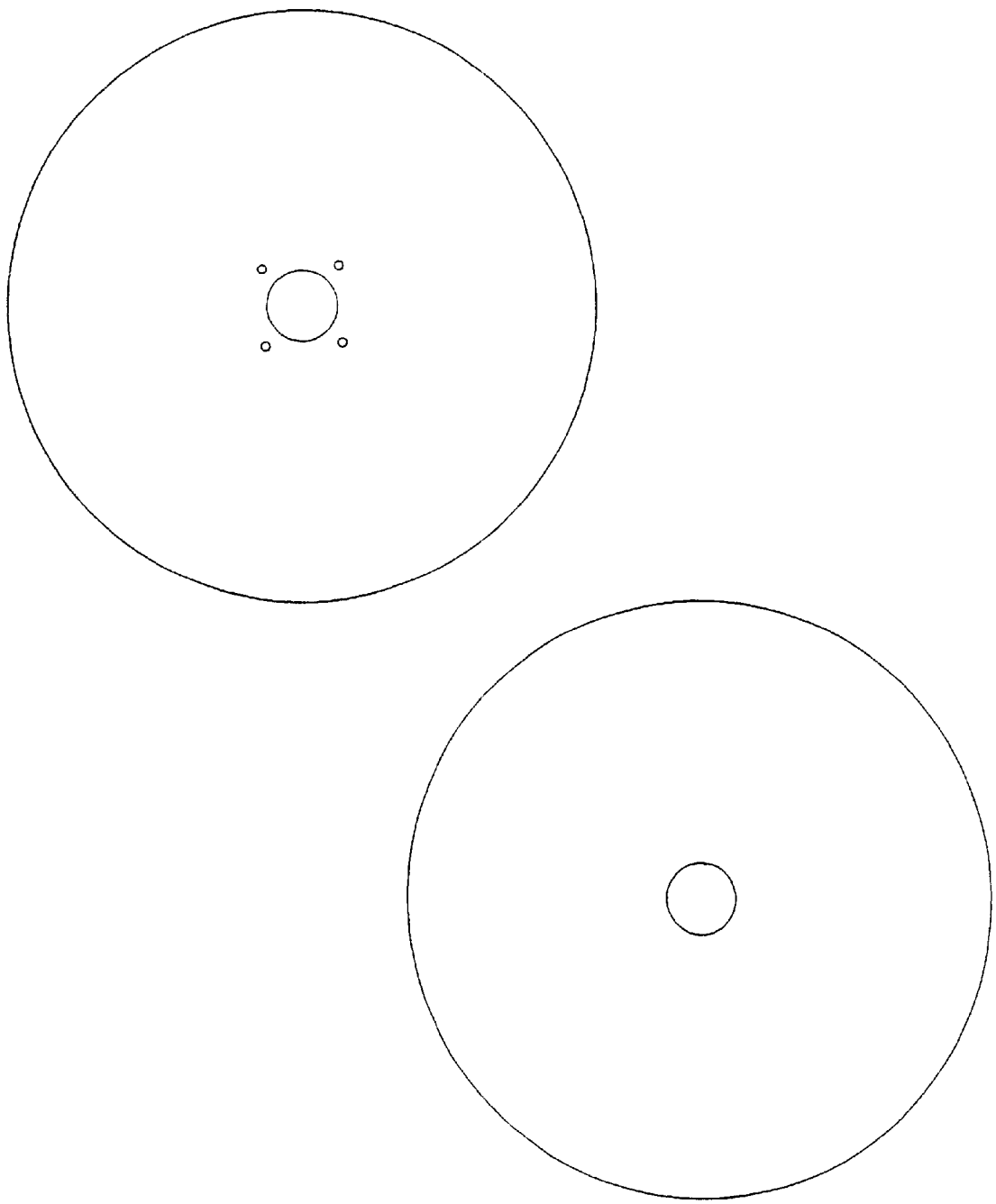
Figure 17D:
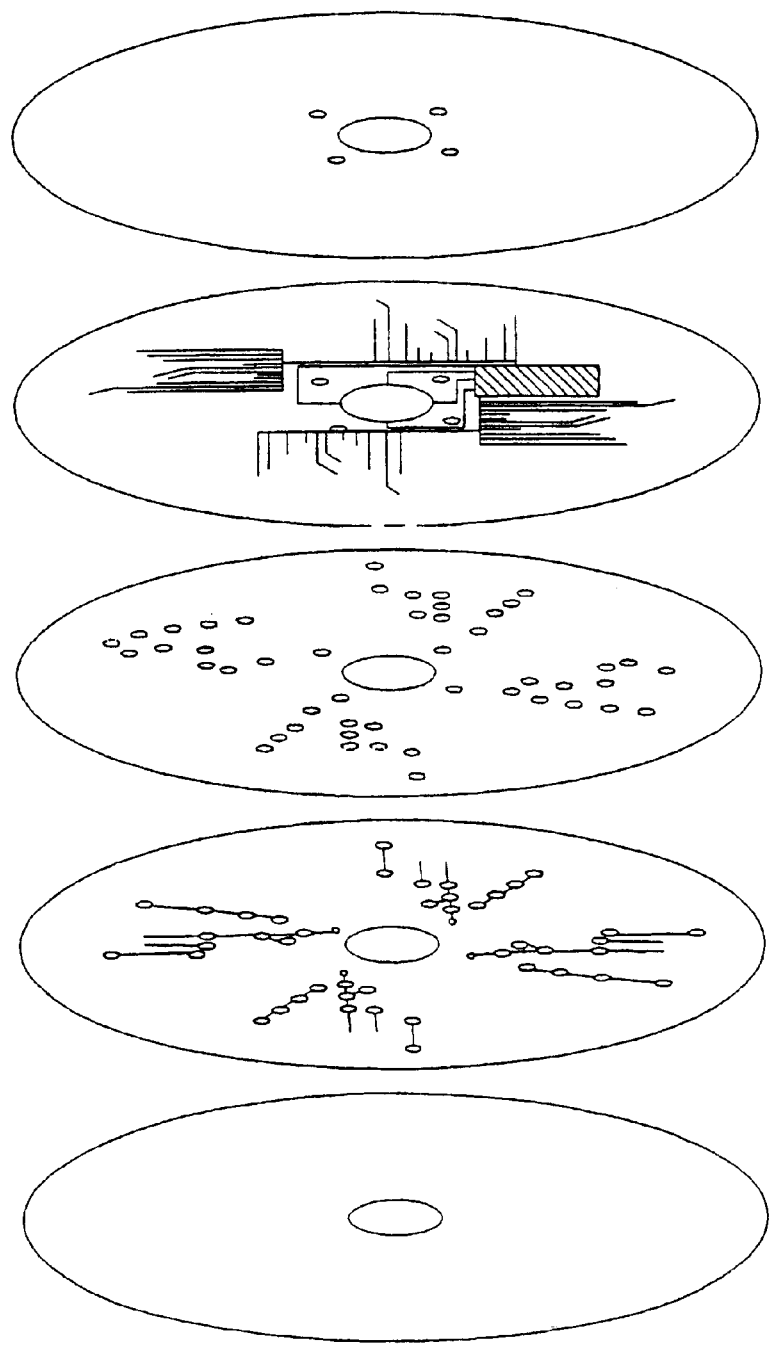
Figure 17E:
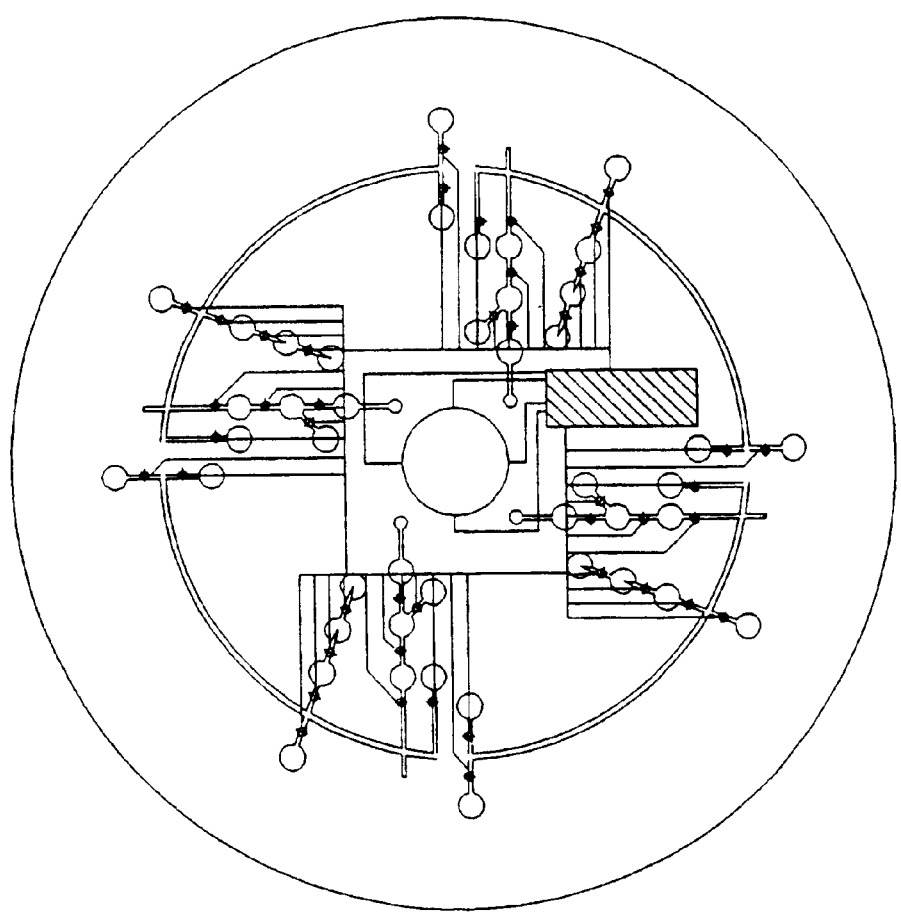
Figure 17F:
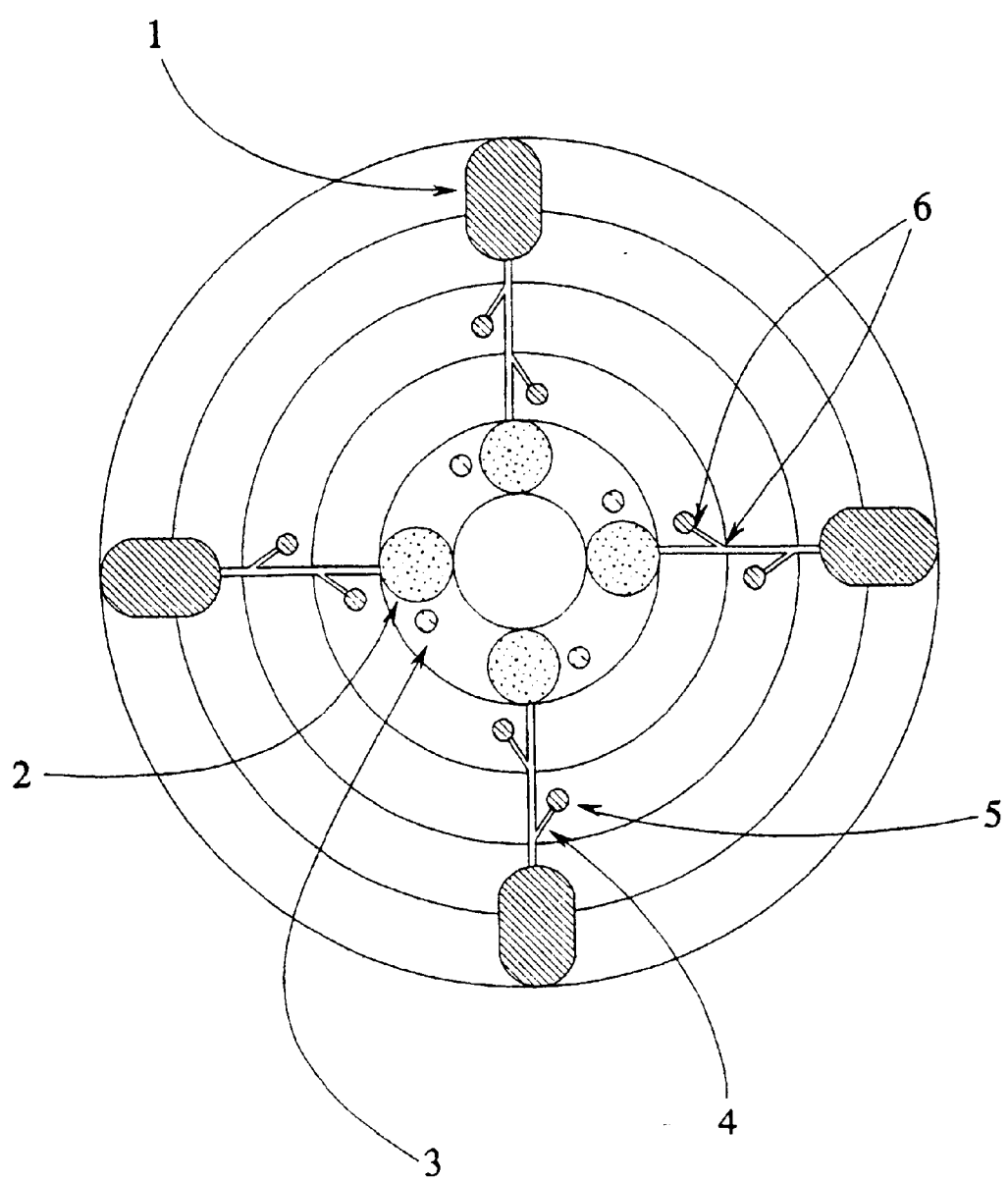
FIG. 17F is a schematic diagram of basic zones and design formats for analytic disks.
Figure 17G:
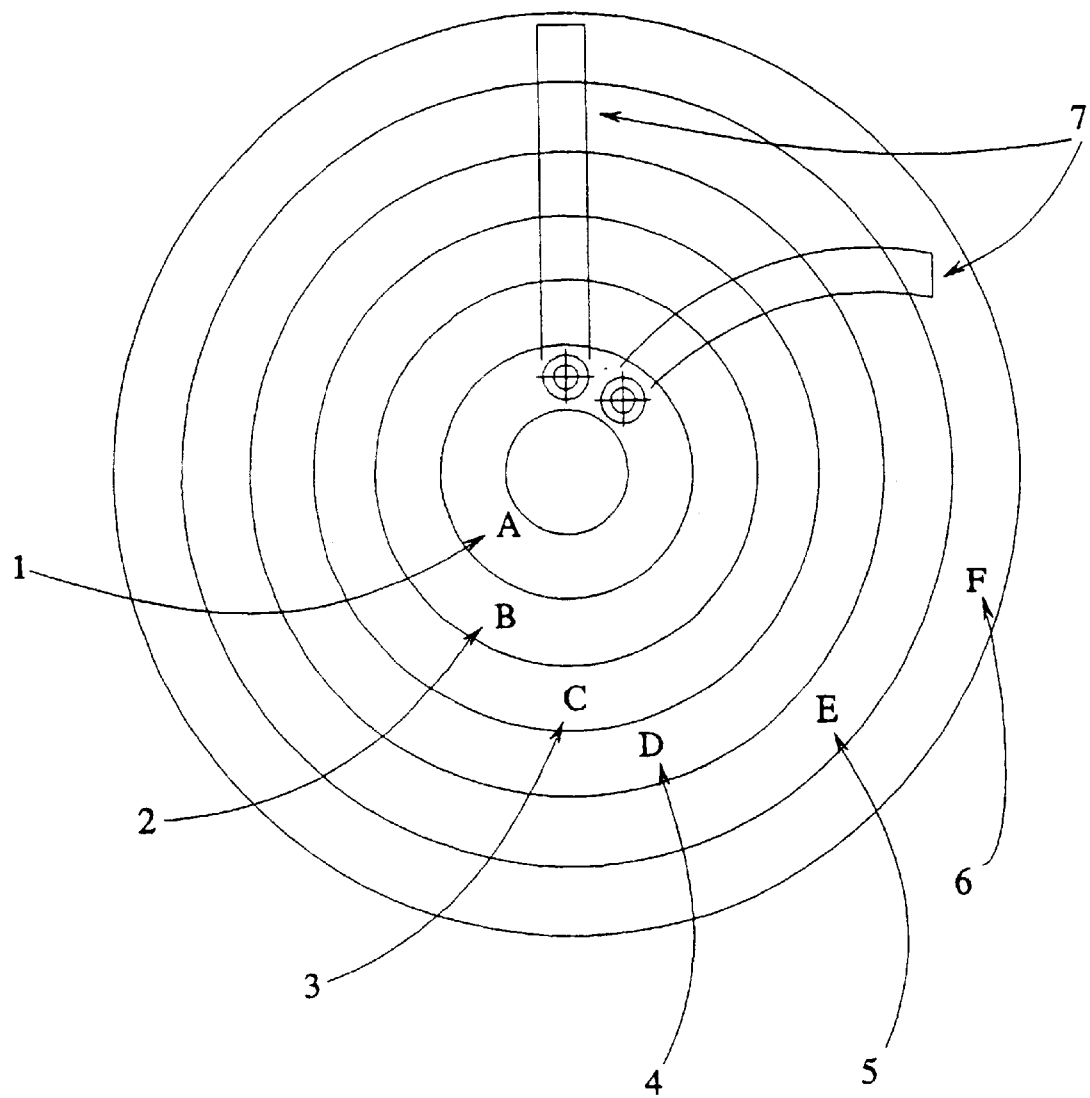
FIG. 17G is a schematic diagram of a disk configured as a home test diagnostic disk.
Figure 17H:
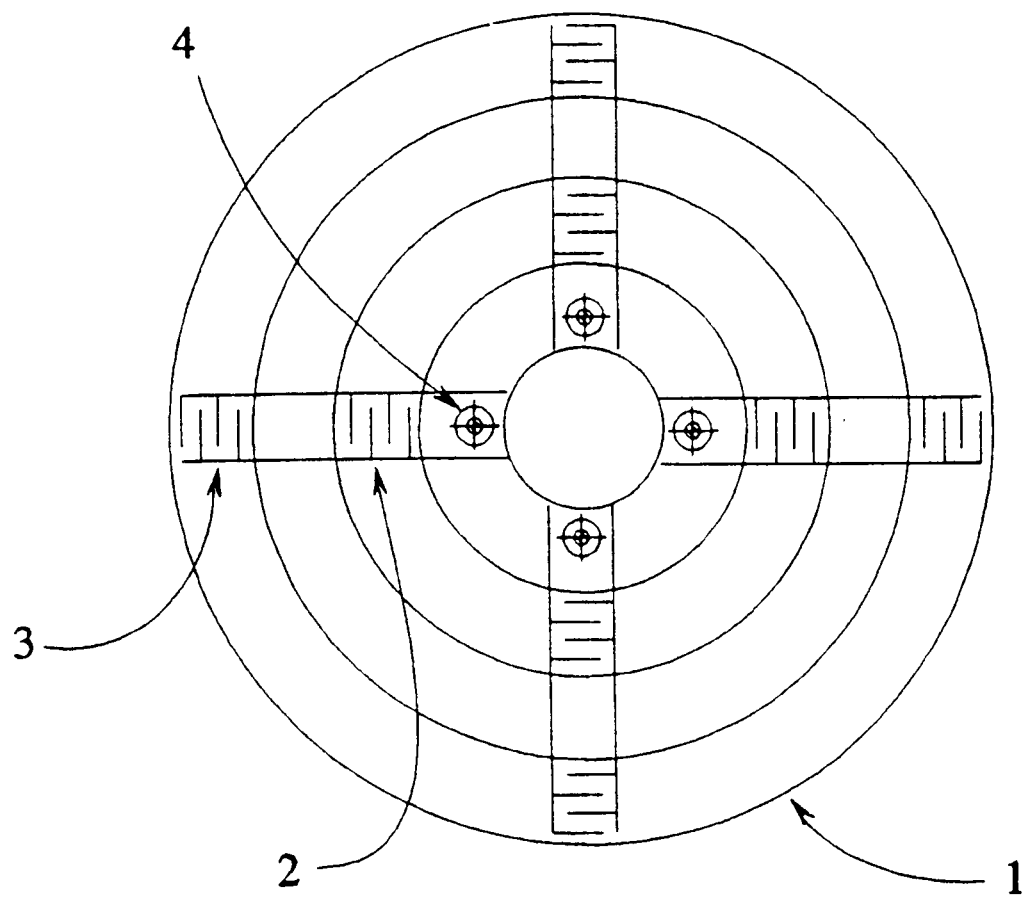
FIG. 17H is a schematic diagram of a disk configured as a simplified immunocapacitance assay.
Figure 17I:
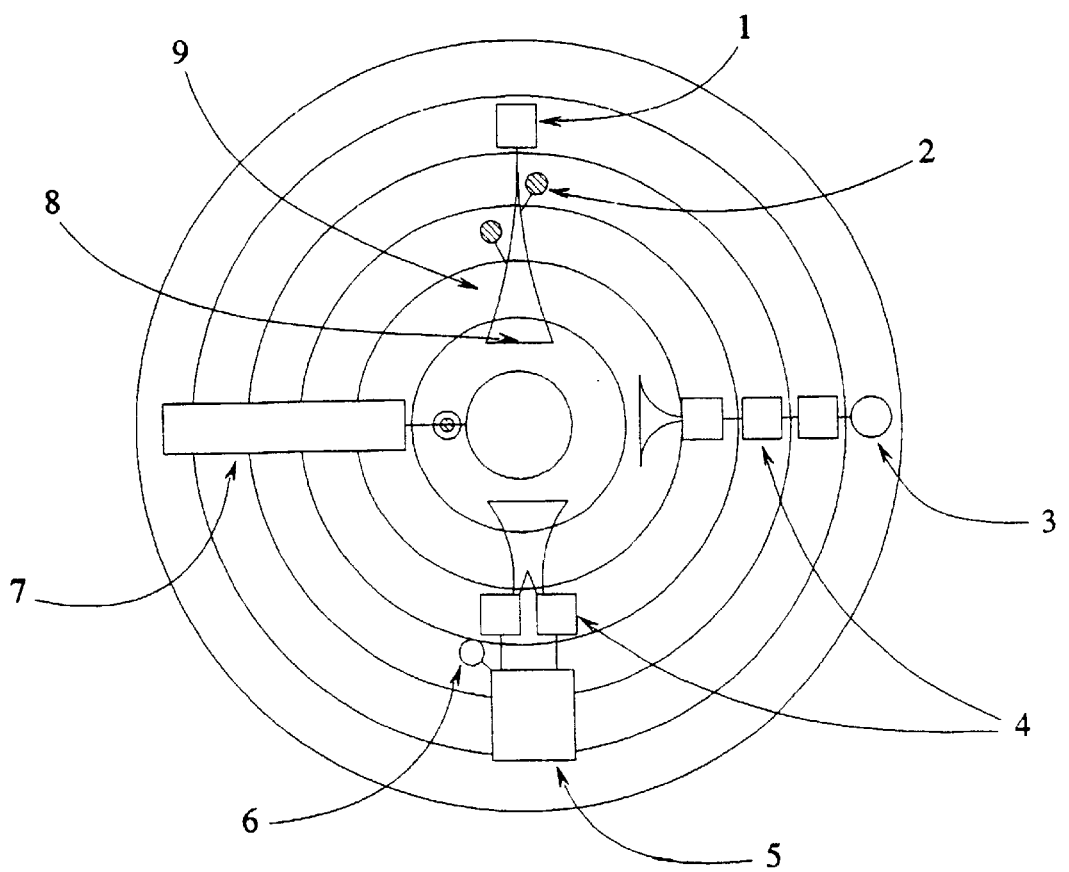
FIG. 17I is a schematic diagram of a disk configured as a gas and particle disk.
Figure 17I:
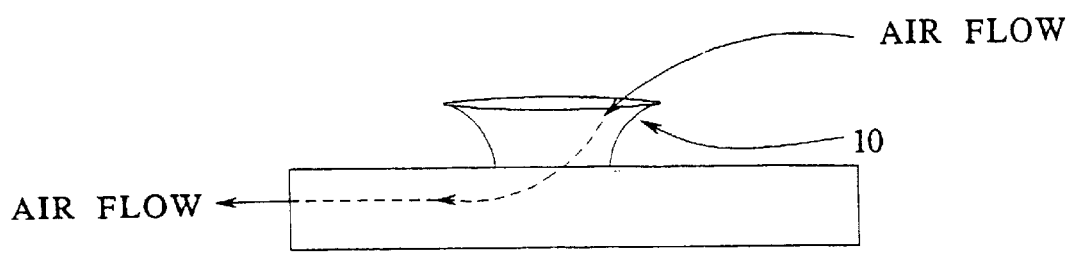
Figure 17J:
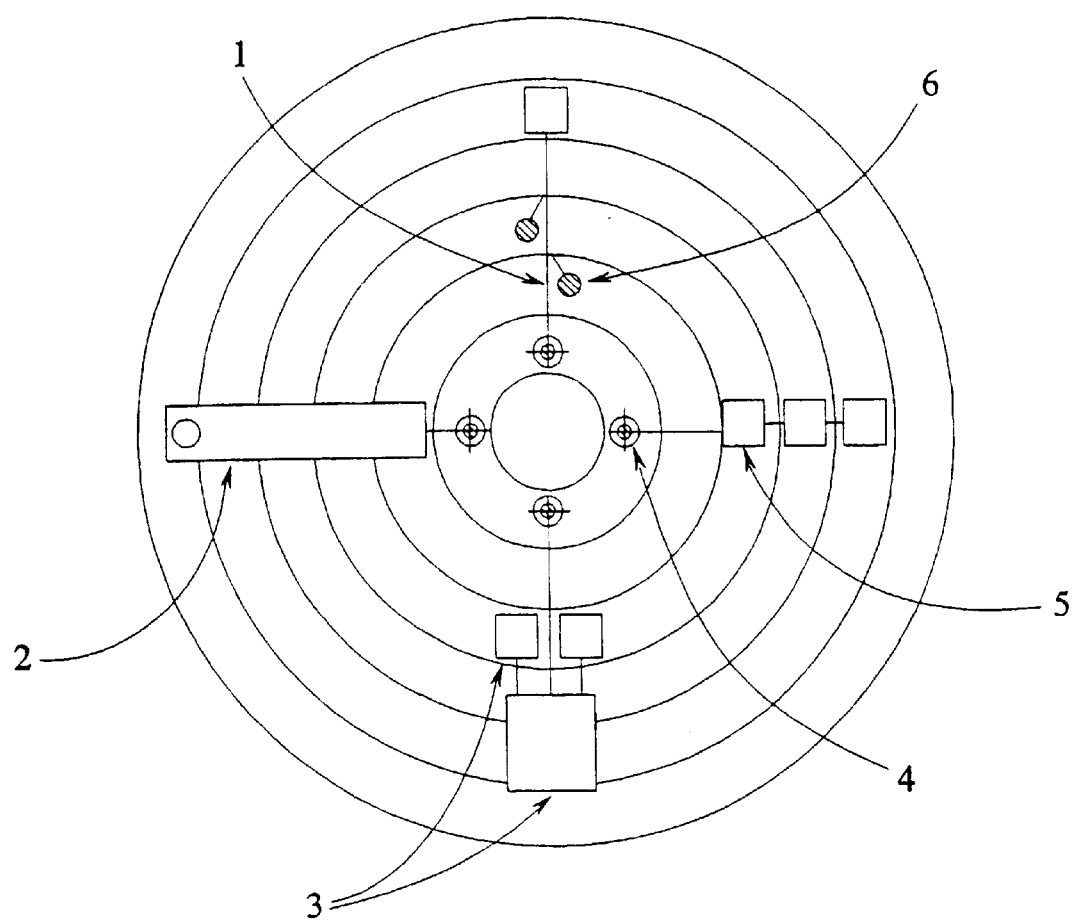
FIG. 17J is a schematic diagram of a hybrid disk comprising separately-assembled chips.
Figure 17K:
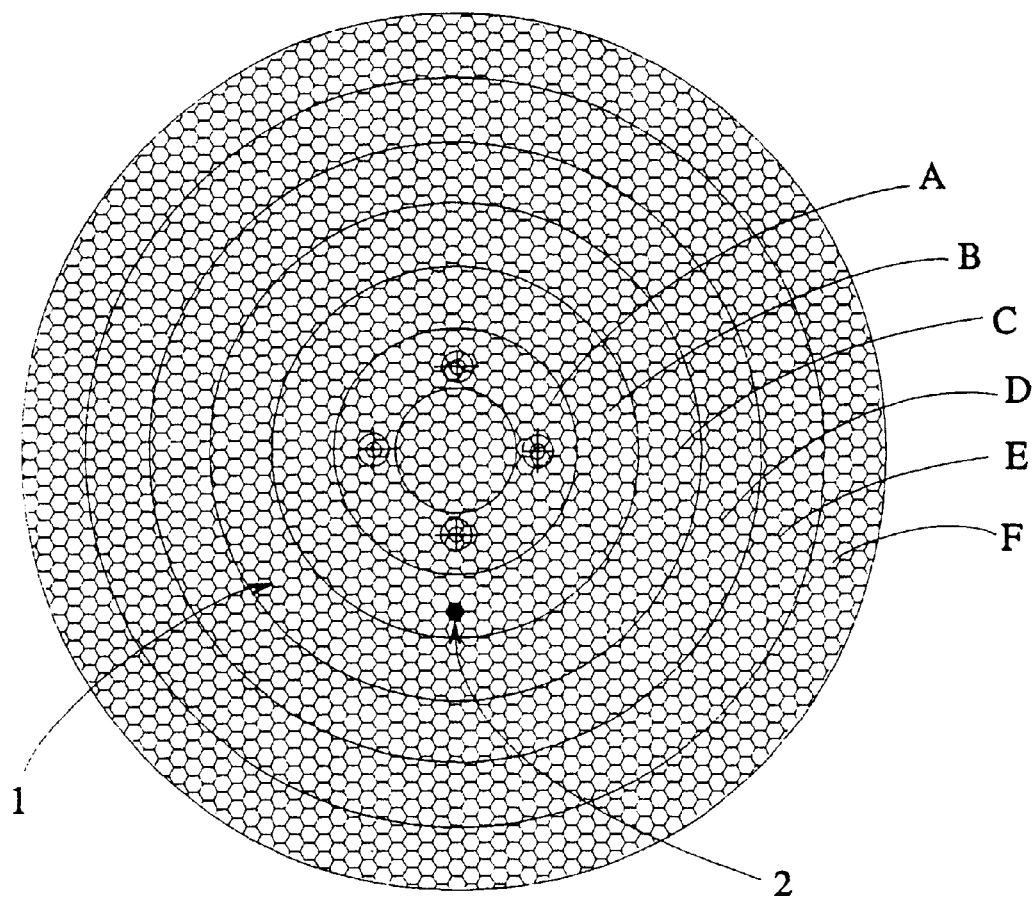
FIG. 17K is a schematic diagram of a sample authorizing disk.
Figure 17L:
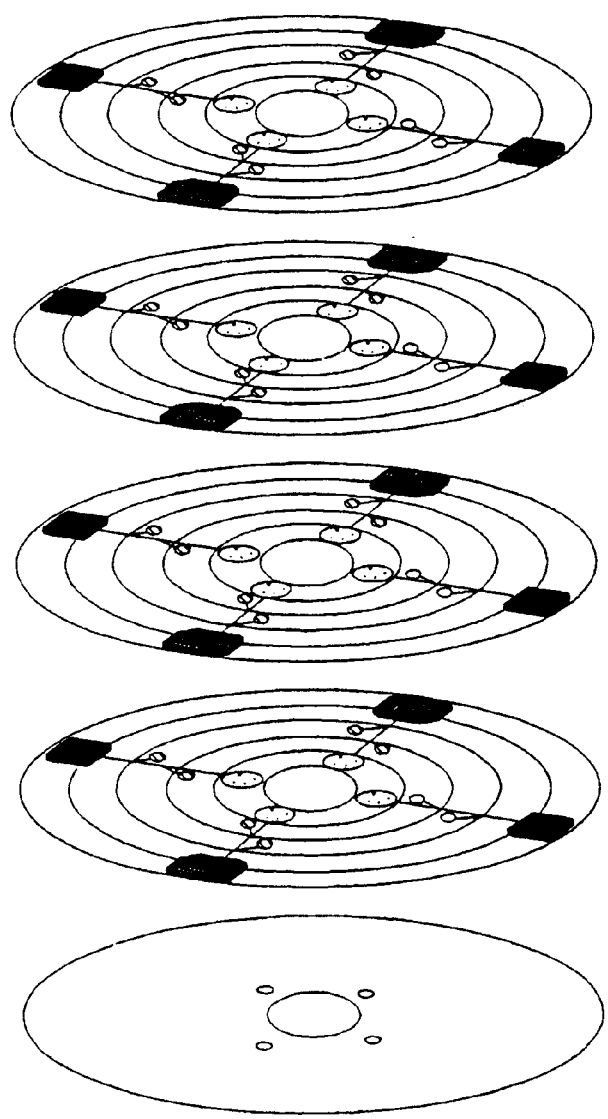
FIG. 17L is a schematic diagram of a disk configured for pathological applications.
Figure 17M:
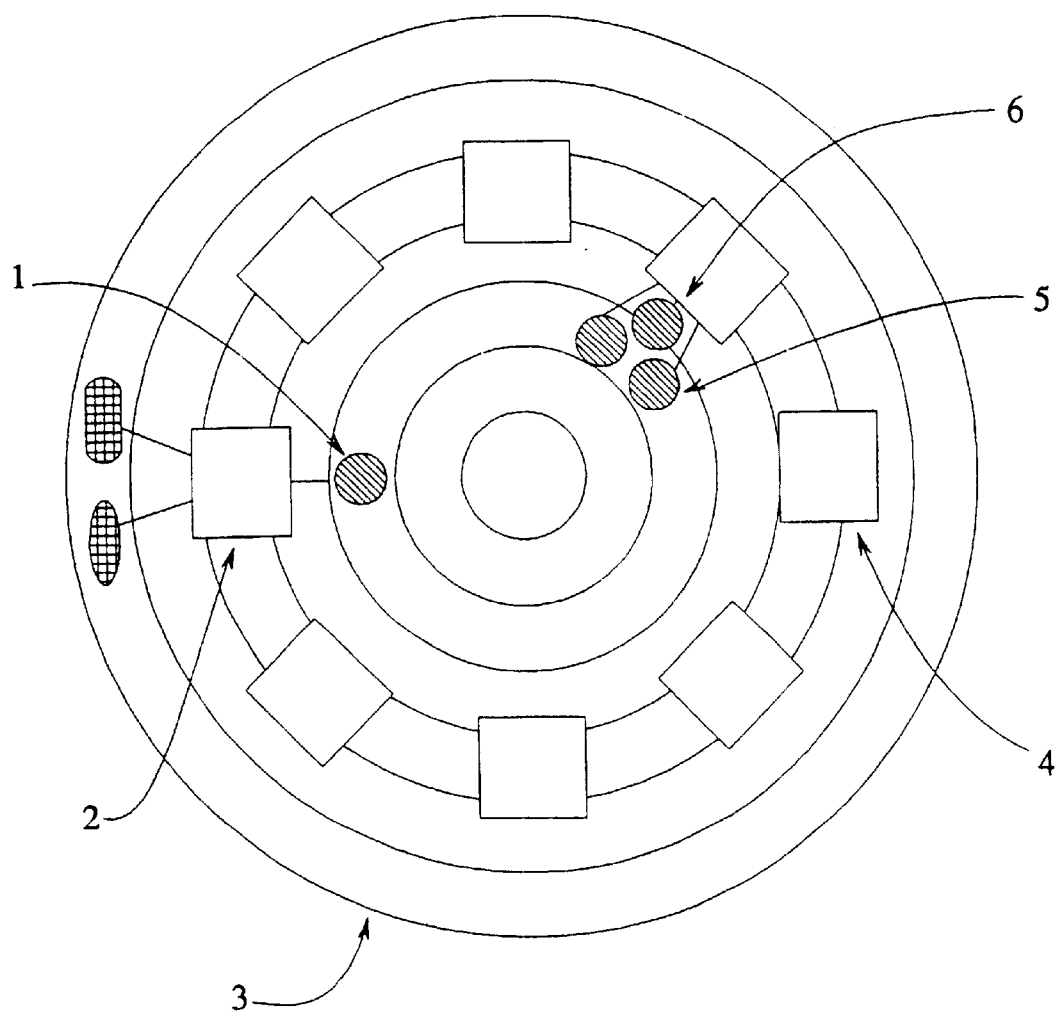
FIG. 17M is a schematic diagram of a disk with removable assay layers.
Figure 17N:
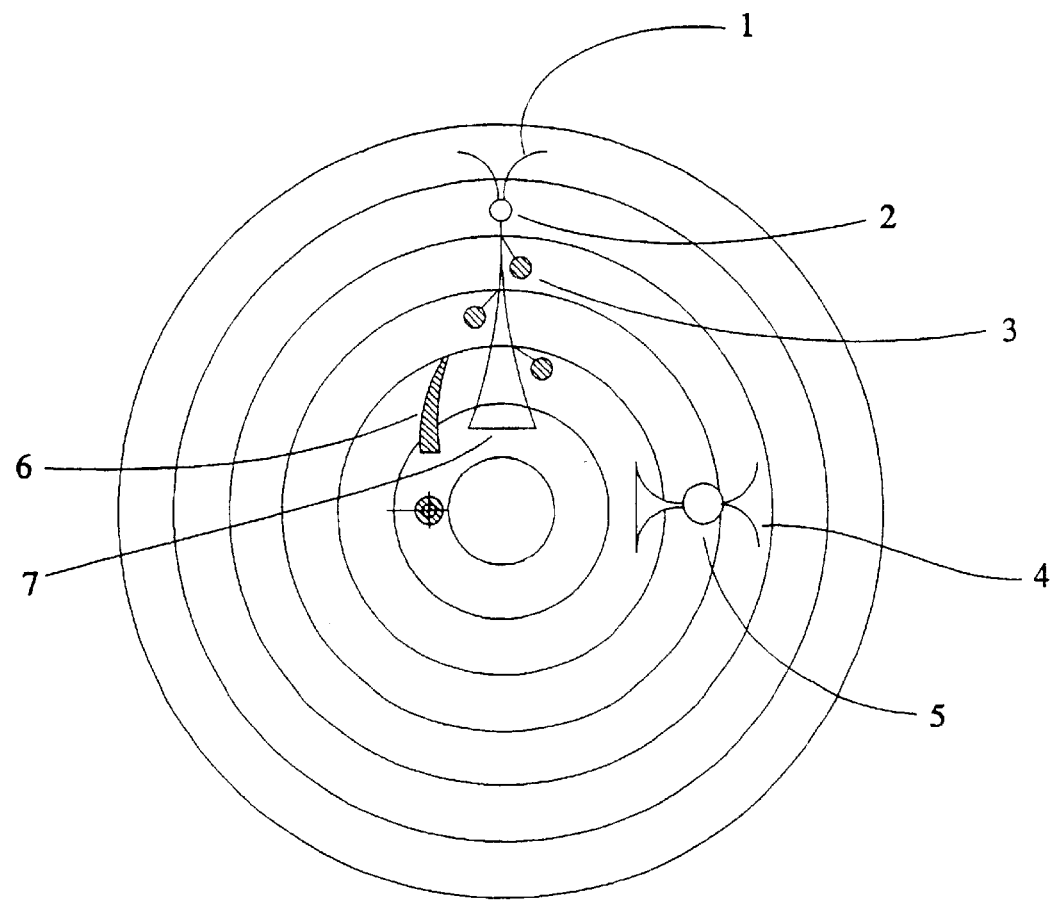
FIG. 17N is a schematic diagram of a disk for assaying aerosols.
Figure 17N:
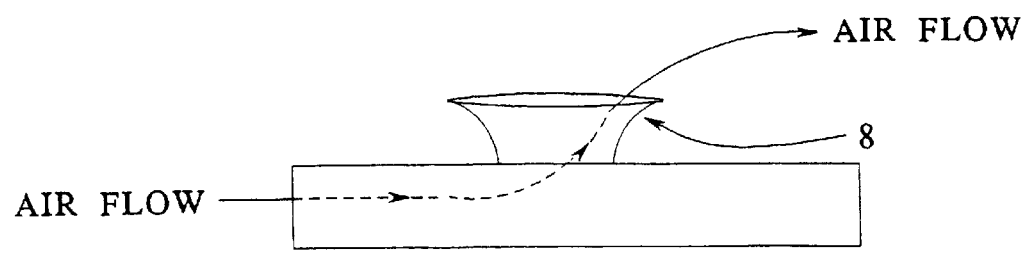
Figure 17O:
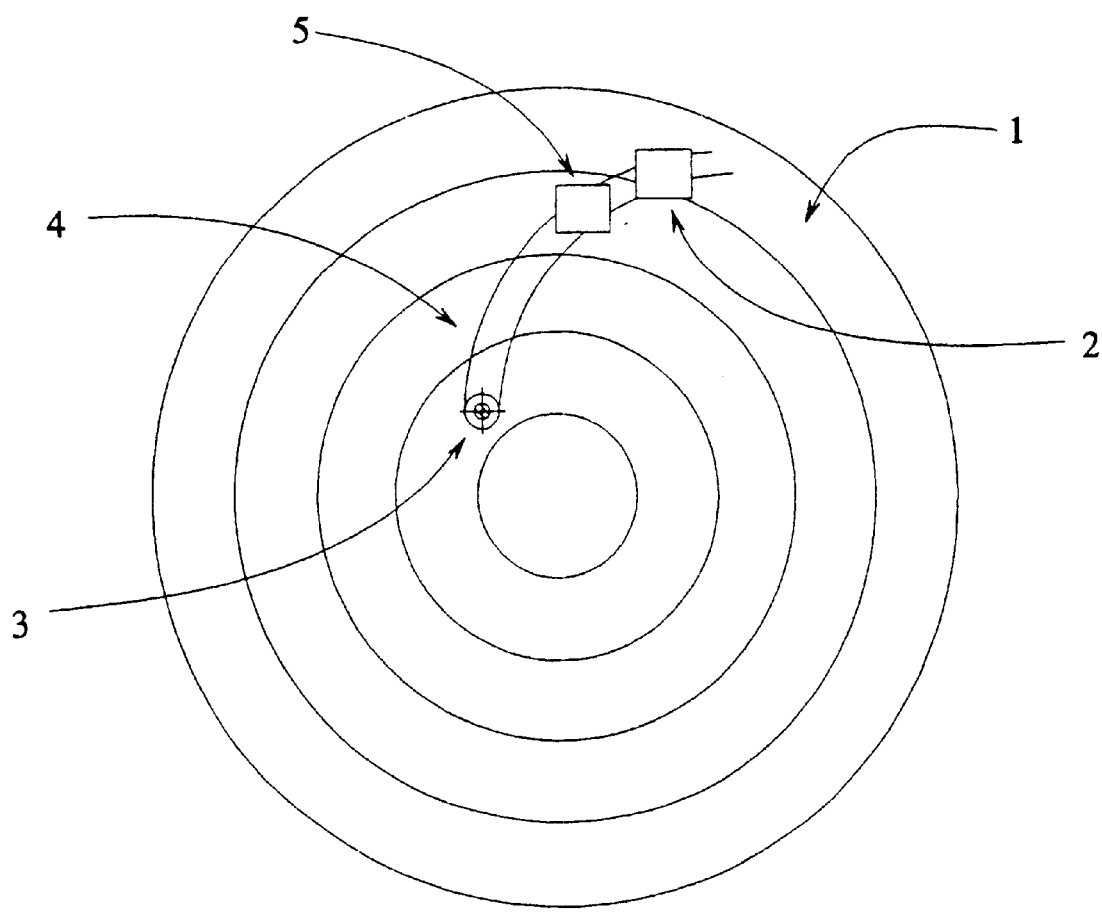
FIG. 17O is a schematic diagram of a disk for flow cytometry.
Figure 17P:
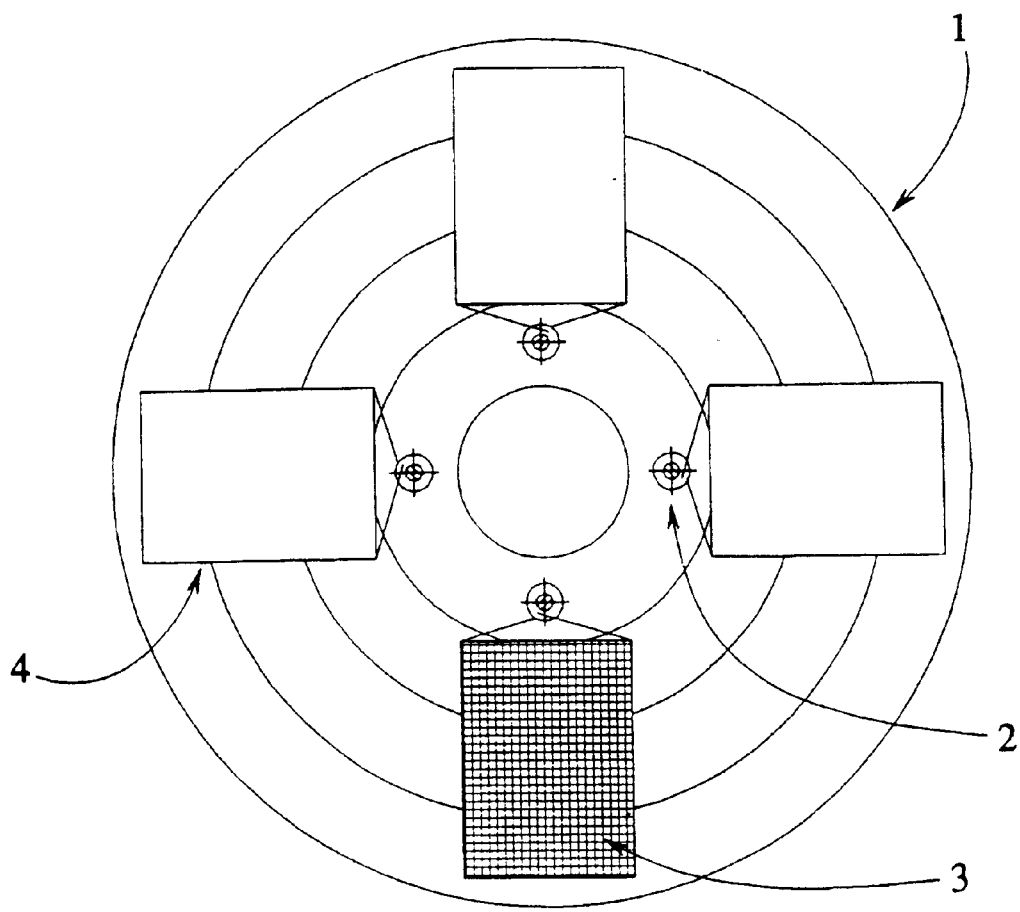
FIG. 17P is a schematic diagram of a disk for microscopy applications.

Embodiments comprising thin film disks are provided, comprising "layers" of microsystems disks stacked on a solid support, are useful for sequential assay with conservation of the disk and efficient and inexpensive use of the microsystem-comprising disks as consumables. An illustration of such disks are shown in FIG. 17L. Such disks are capable of being uniquely identified, for example, by imprinting a barcode directly on the disk.

Particular examples of disks fabricated for a variety of applications is provided below in the Examples.

Disk-Related Devices and Elements

Microsystems platforms (microplatforms) of the invention are provided with a multiplicity of on-board components, either fabricated directly onto the disk, or placed on the disk as prefabricated modules. In addition to be integral components of the disk, certain devices and elements can be located external to the disk, optimally positioned on a device of the invention, or placed in contact with the disk.

1. Temperature Control Elements

Temperature control elements, particularly heating elements, include heat lamps, direct laser heaters, Peltier heat pumps, resistive heaters, ultrasonication heaters and microwave excitation heaters. Cooling elements include Peltier devices and heat sinks, radiative heat fins and other components to facilitate radiative heat loss. Thermal devices can be applied to the disk as a whole or in specific areas on the disk. The thermal elements can be fabricated directly onto the disk, or can be fabricated independently and integrated onto the disk. Thermal elements can also be positioned external to the disk. The temperature of any particular area on the disk is monitored by resistive temperature devices (RTD), thermistors, liquid crystal birefringence sensors or by infrared interrogation using IR-specific detectors. Temperature at any particular region of the disk can be regulated by feedback control systems. A micro-scale thermo-control system can be fabricated directly on the disk, fabricated on a microchip and integrated into the disk or controlled through a system positioned external to the disk.

2. Filters

Filters, sieving structures and other means for selectively retaining or facilitating passage of particulate matter, including cells, cell aggregates, protein aggregates, or other particulate matter comprising fluids applied to a microanalytical or microsynthetic disk of the invention. Such filtering means include microsieving structures that are fabricated directly into a fluid handling structure on the disk (e.g., U.S. Pat. No. 5,304,487; International Application, Publication No. WO93/22053; Wilding et al., 1994, *Automat. Analyt. Tech.* 40: 43–47) or fabricated separately and assembled into the fluid handling structures. The sieving structures are provided with a range of size exclusion orifices and are optionally arranged sequentially so as to fractionate a sample based upon the sizes of the constituent parts of the sample.

Other types of filters include materials that selectively remove sample constituents based on electrostatic forces between the filter material and the sample constituents. The electrostatic composition of the sieving materials may be inherent to the material or bestowed upon it by virtue of a charge delivered to the material through an electronic circuit. The materials captured by the filter material can be irreversibly bound or can be selectively eluted for further processing by adjusting the composition and ionic strength of buffers or, in the case of an electronically regulated material, by modulating the electronic state of the material.

In yet other embodiments of the filters of the microsystem platforms of this invention, specific components of a sample can be retained in a section, microchannel or reservoir of a disk of the invention by interaction with specific proteins, peptides, antibodies or fragments thereof derivatized to be retained within the surface of a component of the disk. Materials captured by such specific binding can be eluted from the surface of the disk and transferred to a collection reservoir by treatment with appropriately-chosen ionic strength buffers, using conventional methods developed for immunological or chromatographic techniques.

The invention also provides compartments defined by sections of a microchannel or by a chamber or reservoir wherein the inlet and outlet ports of the chamber are delimited by a filtering apparatus. In certain embodiments, the chamber thus defined contains a reagent such as a bead and particularly a bead coated with a compound such as an antibody having an affinity for a contaminant, unused reagent, reaction side-product or other compound unwanted in a final product. In the use of disks comprising such a filter-limited chamber, a fluid containing a mixture of wanted and unwanted compounds is moved through the filter chamber by centripetal force of the rotating disk. The unwanted compounds are thus bound by the affinity material, and the desired compounds flushed free of the chamber by fluid flow motivated by centripetal force.

Alternatively, the desired compound may be retained in such a filter-limited chamber, and the unwanted compounds flushed away. In these embodiments, egress from the chamber, for example by the opening of a valve, is provided.

Mixers

A variety of mixing elements are advantageously included in embodiments of the Microsystems disks of the invention that require mixing of components in a reaction chamber upon addition from a reagent reservoir. Static mixers can be incorporated into fluid handling structures of the disk by applying a textured surface to the microchannels or chambers composing the mixer. Two or more channels can be joined at a position on the disk and their components mixed together by hydrodynamic activity imparted upon them by the textured surface of the mixing channel or chamber and the action of centripetal force imparted by the rotating disk. Mixing can also be accomplished by rapidly changing the direction of rotation and by physically agitating the disk by systems external to the disk.

In other embodiments, flex plate-wave (FPW) devices (see White, 1991, U.S. Pat. No. 5,006,749, ibid.) can be used to effect mixing of fluids on a disk of the invention. FPW devices utilize aluminum and piezoelectric zinc oxide transducers placed at either end of a very thin membrane. The transducers launch and detect acoustic plate waves that are propagated along the membrane. The stiffness and mass per unit area of the membrane determine the velocity of plate wave. When connected with an amplifier, the waves form a delay-line oscillation that is proportional to the acoustic wave velocity. Structures based on the FPW phenomena have been used to sense pressure, acceleration, organic chemical vapors, the adsorption of proteins, the density and viscosity of liquids as well as to mix liquids together. FPW devices can be integrated onto the disk or can be positioned in proximity to the disk to effect mixing of fluid components in particular reaction chambers on the disk.

4. Valving Mechanisms

Figure 6:
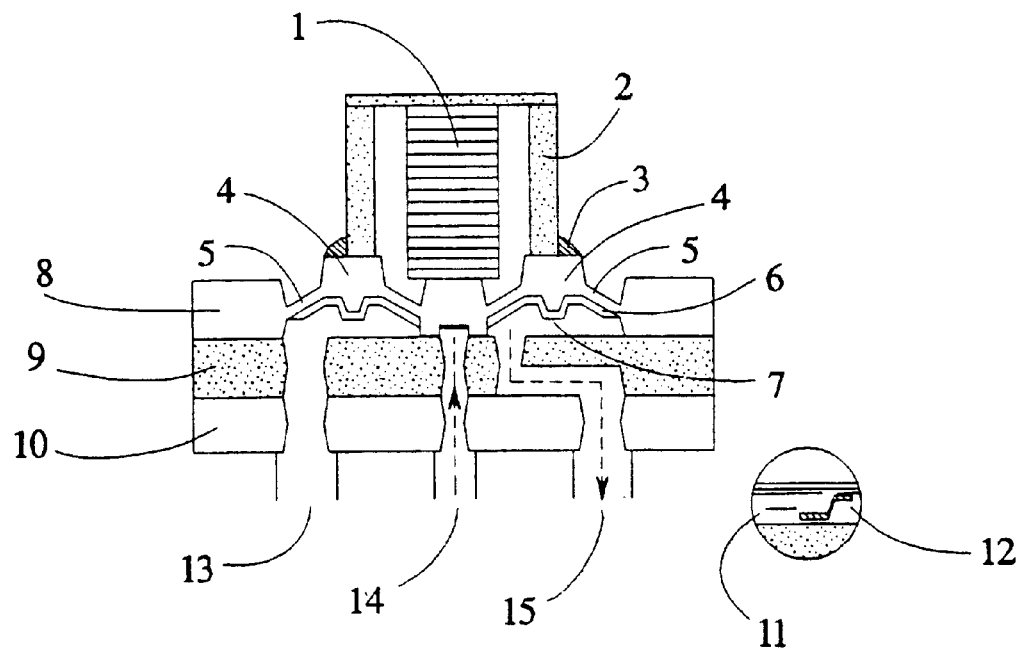
FIG. 6 is a schematic diagram of a piezoelectric stack microvalve.
Figure 6:
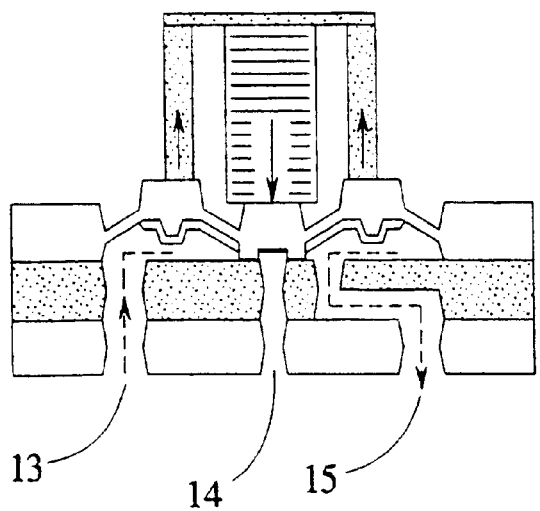

Control of fluid movement and transfer on the disk typically includes the use of valving mechanisms (microvalves) to permit or prevent fluid movement between components. Examples of such microvalves include a piezo activator comprising a glass plate sandwiched between two silicon wafers, as described by Nakagawa et al. (1990, Proc. IEEE Workshop of Micro Electro Mechanical Systems, Napa Valley, Calif. pp. 89); a schematic diagram of such a valve is shown in FIG. 6. In this embodiment, a lower wafer and glass plate can have one or two inlets and one outlet channel etched in them. An upper wafer can have a circular center platform and a concentric platform surrounding it. The base of piezoelectric stack can be placed onto the center platform and its top connected to the concentric platform by means of circular bridge. The center of a $SiO_2/SiN_4$ arch-like structure is connected to the piezo element. Valve seats are made of nickel or other sealing substance. In a three-way embodiment, fluid moves from the center inlet port to the outlet with no applied voltage. With a voltage applied the piezo element presses down on the arch center causing the ends to lift, blocking the center inlet and allowing fluid to flow from the peripheral inlet. In other, two-way embodiments, fluid flows with no applied voltage and is restrained upon the application of voltage. In another embodiment of a two-way valve, fluid is restrained in the absence of an applied voltage and is allowed to flow upon application of a voltage. In any of these embodiments the piezo stack can be perpendicular to the plane of rotation, oblique to the plane of rotation, or held within the plane of rotation.

Figure 7:
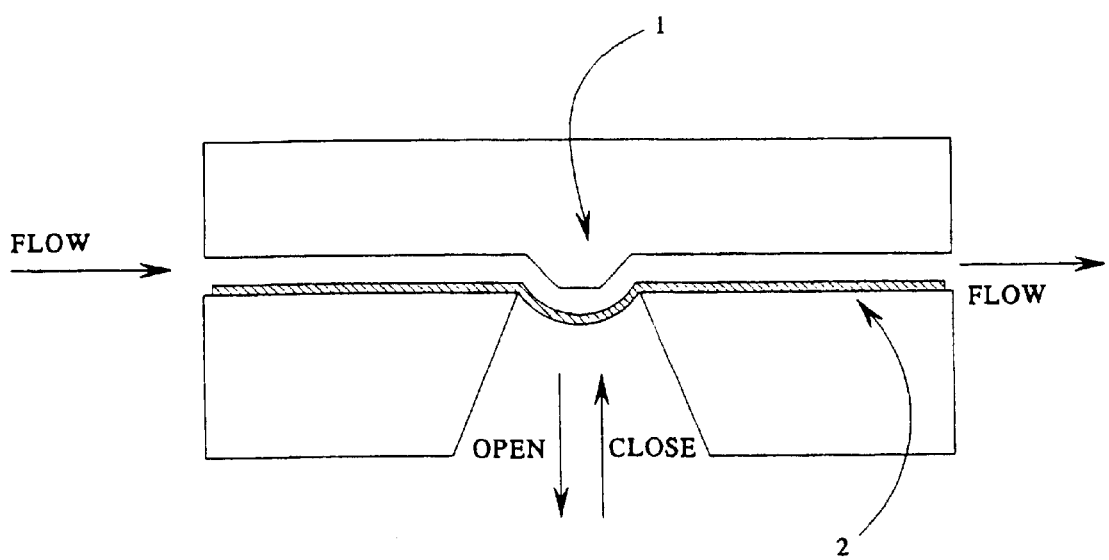
FIG. 7 is a schematic diagram of a pneumatically-activated microvalve.
Figure 8:
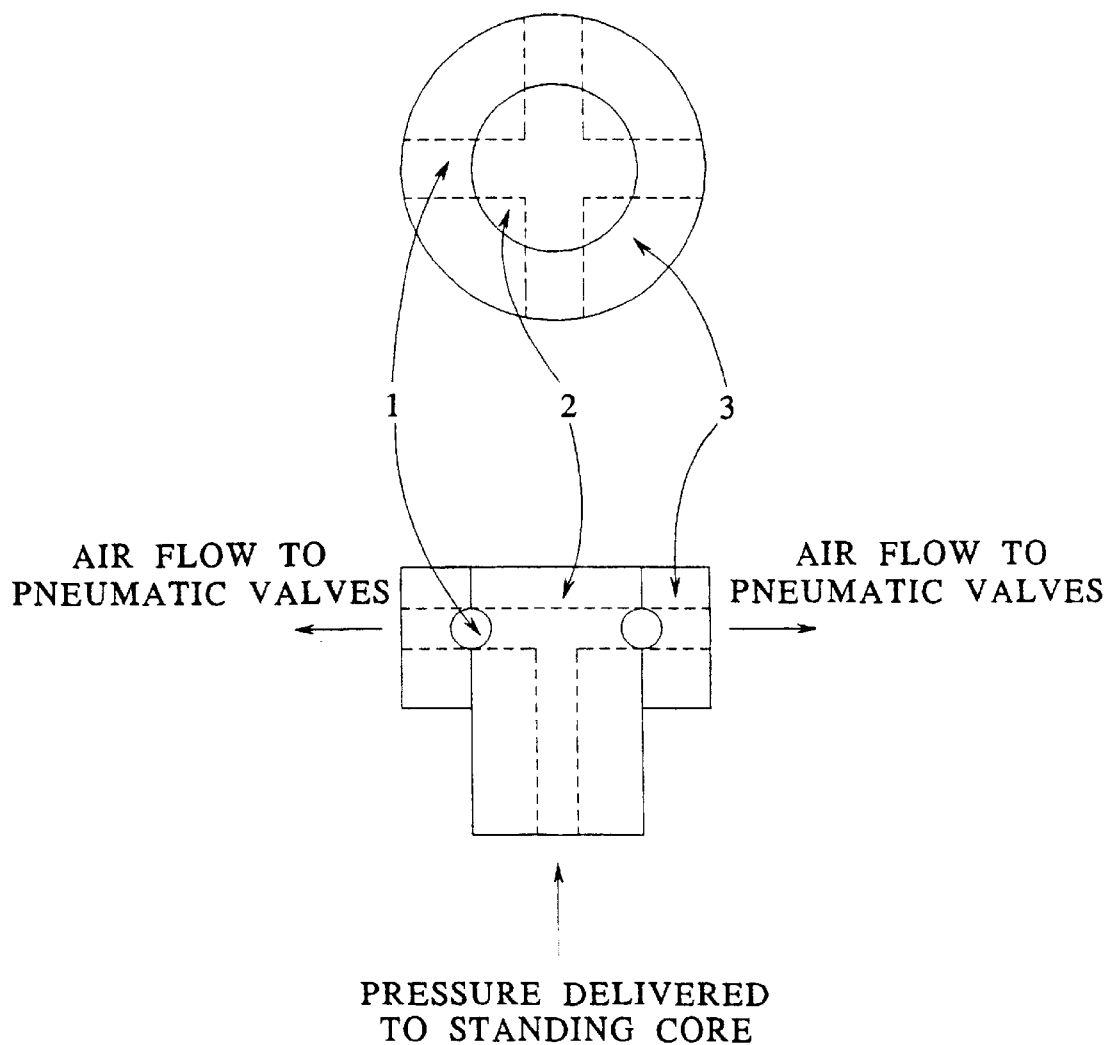
FIG. 8 is a schematic diagram of device to deliver pneumatic pressure to a revolving disk.

In another embodiment, fluid control is effected using a pneumatically-actuated microvalve wherein a fluid channel is etched in one layer of material that has a raised valve seat at the point of control (a schematic diagram of this type of valve is shown in FIG. 7). Into another layer, a corresponding hole is drilled, preferably by a laser to achieve a hole with a sufficiently small diameter, thereby providing pneumatic access. Onto that second structure a layer of silicone rubber or other flexible material is spun-deposited. These structures are then bonded together. Fluid movement is interrupted by the application of air pressure which presses the flexible membrane down onto the raised valve seat. This type of valve has been described by Veider et al. (1995, Eurosensors IX, pp. 284–286, Stockholm, Sweden, June 25–29). Measurements made by Veider et al. have shown that a similar valve closes completely with the application of 30 KPa of pressure over the fluid inlet pressure. This value corresponds to 207 psig, and can be adjusted by changing the diameter of the pneumatic orifice and the thickness of the membrane layer. Pneumatic pressure is applied to the disk to activate such valves as shown schematically in FIG. 8.

Figure 9:
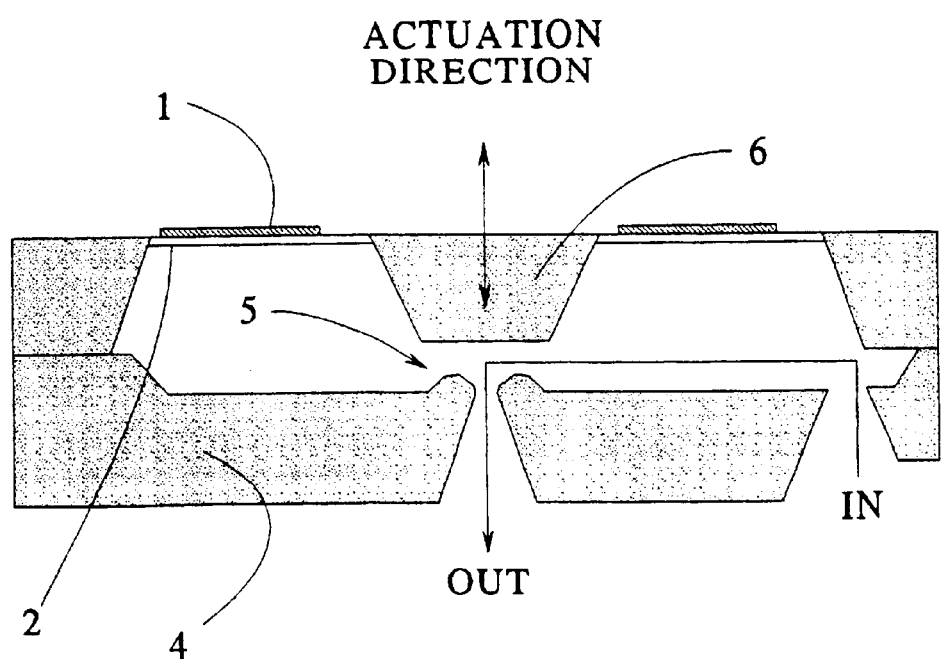
FIG. 9 is a schematic diagram of a bimetallic microvalve.

Pneumatic actuation can also be embodied by a micromachined gas valve that utilizes a bimetallic actuator mechanism, as shown in FIG. 9. The valve consists of a diaphragm actuator that mates to the valve body. The actuator can contain integral resistive elements that heat upon application of a voltage, causing a deflection in the diaphragm. This deflection causes a central structure in the actuator to impinge upon the valve opening, thus regulating the flow of fluid through the opening. These valves allow proportional control based on voltage input, typically 0–15 V DC. These types of valve are commercially available (Redwood Microsystems, Menlo Park, Calif.; ICSensors, Milpitas, Calif.).

Embodiments of pneumatically actuated membrane valves can include integration of both components on a single disk or can comprise two disks aligned so that the pneumatic outlets of one disk align with the second disk to impinge upon the pneumatic actuation orifice of the other disk. In either embodiment a source of pneumatic pressure can be delivered to the disk via concentric rings of material such a Teflon®. In this embodiment, a standing core and a revolving element are contiguous to the disk. Pneumatic pressure is delivered through the interior of the standing core and directed by channels to the outer edge of the standing core. Suitably placed channels are machined into the revolving element and impinge upon the channels in the standing core and direct the pneumatic pressure to the gas valves.

Figure 10:
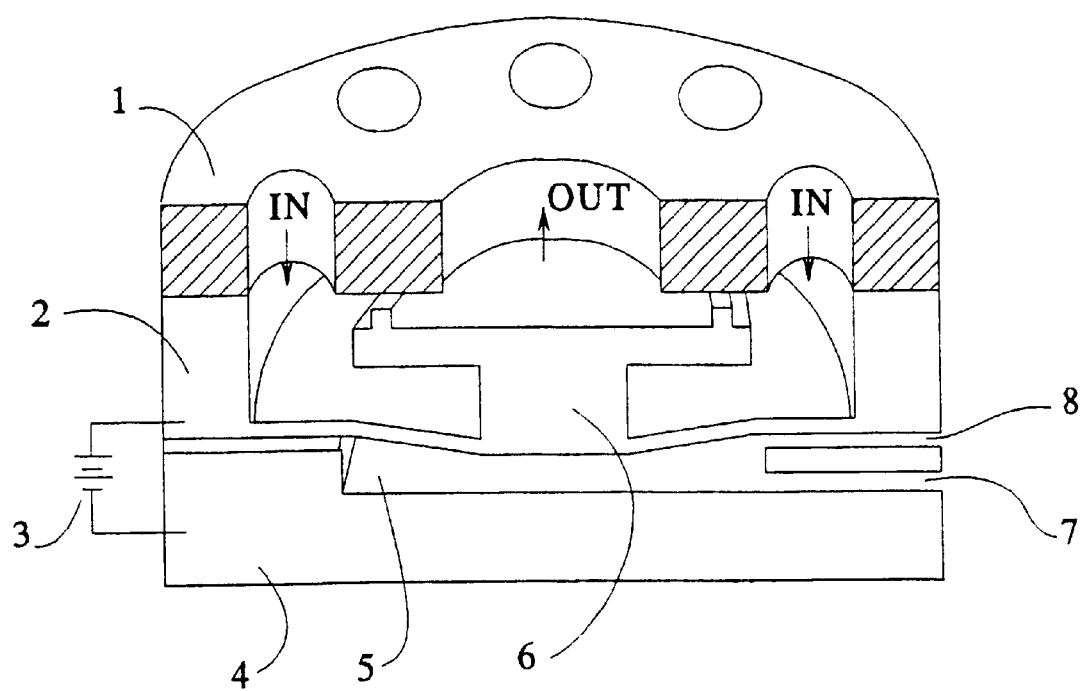
FIG. 10 is a schematic diagram of a pressure-balanced microvalve.

Another valve embodiment is a pressure-balanced microvalve, shown in FIG. 10. This type of valve is constructed of three layers of material, comprising two layers of silicon separated by a thin layer of electrically-insulating oxide (i.e., silicon dioxide). A glass layer is bonded onto the top of the valve and advantageously contains inlet and outlet ports. A center plunger fashioned in the middle silicon layer is deflected into a gap contained on the lower silicon layer by application of a voltage between the silicon layers. Alternatively, the plunger is deflected by providing a pneumatic pressure drop into a gap in the lower layer. Irreversible jamming of micromachined parts may be prevented by the application of a thin layer of Cr/Pt to the glass structure. As an electrostatically driven device, this type of valve has many advantages, including that it may be wired directly in the fabrication of the disk. In this embodiment the actuator is a finely tuned device that requires minimal input energy in order to open the valve even at relatively high pressures. These types of valves have been disclosed by Huff et al.

(1994, 7$^{th}$ International Conference on Solid-State Sensors and Actuators, pp. 98–101).

Figure 11:
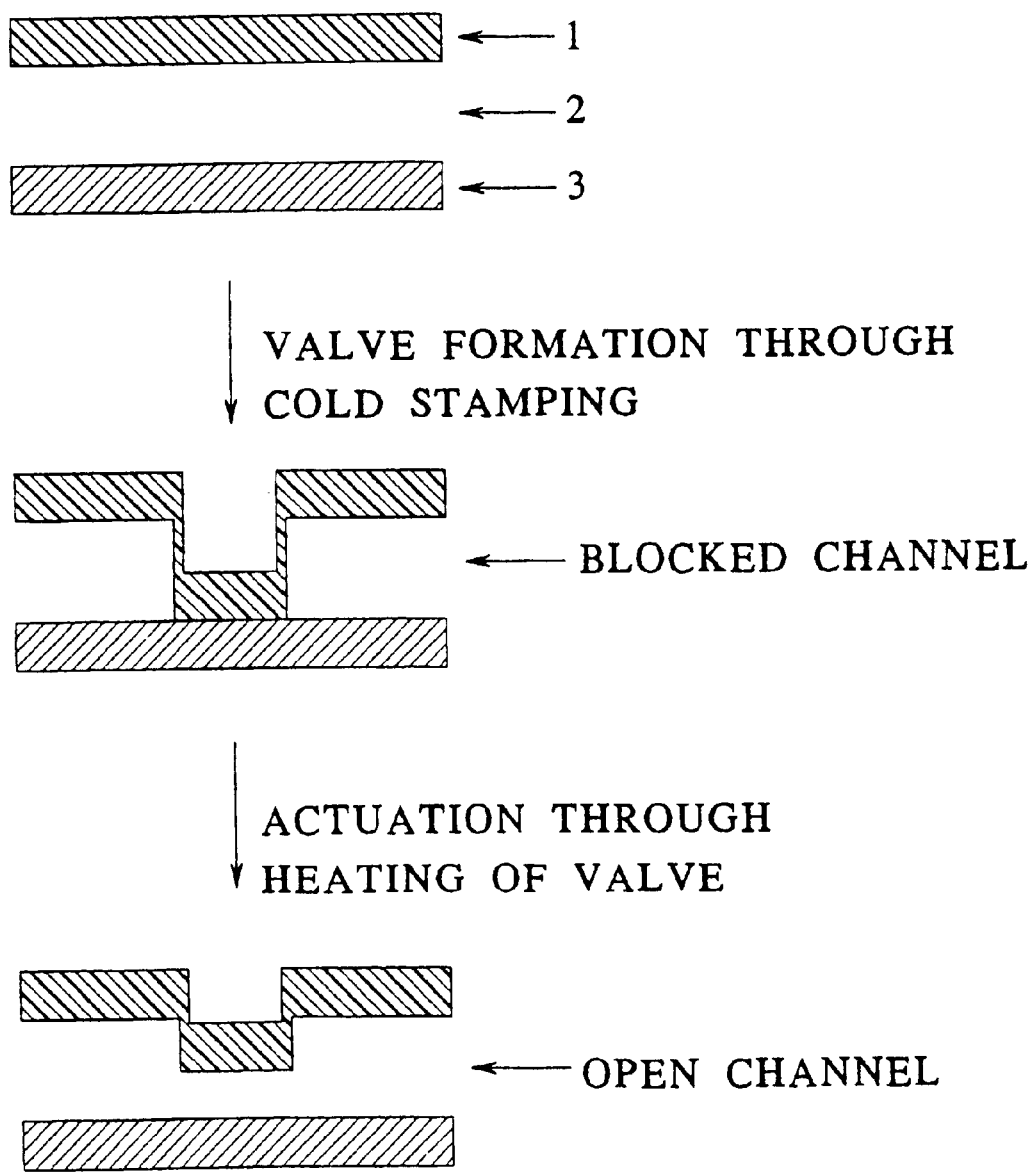
FIG. 11 is a schematic diagram of a polymeric relaxation microvalve.

Another type of single-use valve, termed a polymeric relaxation valve, compatible with the disk and fluidic devices in general, is disclosed herein and shown in FIG. 11. This valve is based on the relaxation of non-equilibrium polymeric structures. This phenomenon is observed when polymers are stretched at temperatures below their glass transition temperature ($T_g$), resulting in a non-equilibrium structure. Upon heating above the $T_g$, the polymer chains relax and contraction is observed as the structure equilibrates. A common example of this phenomenon is contraction of polyolefin (used in heat shrink tubing or wrap), the polyolefin structure of which is stable at room temperature. Upon heating to 135° C., however, the structure contracts. Examples of PR valve polymers include but are not limited to polyolefins, polystyrenes, polyurethanes, poly(vinyl chloride) and certain fluoropolymers.

One way to manufacture a PR valve is to place a polymer sheet or laminate over a channel requiring the valve (as shown in FIG. 11). A cylindrical valve is then cold-stamped in such a way as to block the microchannel. The valve is actuated by the application of localized heat, for example, by a laser or by contact with a resistive heating element. The valve then contracts and fluid flow is enabled.

A further type of microvalve useful in the disks of the invention is a single use valve, illustrated herein by a capillary microvalve (disclosed in U.S. Provisional Application Serial No. 60/023,756, filed Aug. 12, 1996 and incorporated by reference herein). This type of microvalve is based on the use of rotationally-induced fluid pressure to overcome capillary forces. Fluids which completely or partially wet the material of the microchannels (or reservoirs, reaction chambers, detection chambers, etc.) which contain them experience a resistance to flow when moving from a microchannel of narrow cross-section to one of larger cross-section, while those fluids which do not wet these materials resist flowing from microchannels (or reservoirs, reaction chambers, detection chambers, etc.) of large cross-section to those with smaller cross-section. This capillary pressure varies inversely with the sizes of the two microchannels (or reservoirs, reaction chambers, detection chambers, etc., or combinations thereof, the surface tension of the fluid, and the contact angle of the fluid on the material of the microchannels (or reservoirs, reaction chambers, detection chambers, etc.). Generally, the details of the cross-sectional shape are not important, but the dependence on cross-sectional dimension results in microchannels of dimension less than 500 μm exhibit significant capillary pressure. By varying the intersection shapes, materials and cross-sectional areas of the components of the Microsystems platform of the invention, "valve" are fashioned that require the application of a particular pressure on the fluid to induce fluid flow. This pressure is applied in the disks of the invention by rotation of the disk (which has been shown above to vary with the square of the rotational frequency, with the radial position and with the extent of the fluid in the radial direction). By varying capillary valve cross-sectional dimensions as well as the position and extent along the radial direction of the fluid handling components of the microsystem platforms of the invention, capillary valves are formed to release fluid flow in a rotation-dependent manner, using rotation rates of from 100 rpm to several thousand rpm. This arrangement allows complex, multistep fluid processes to be carried out using a pre-determined, monotonic increase in rotational rate.

Control of the microvalves of the disks provided by the invention is achieved either using on-disk controller elements, device-specific controllers, or a combination thereof.

6. Control Systems

Integrated electronic processing systems (generally termed "controllers" herein) that include microprocessors and I/O devices can be fabricated directly onto the disk, can be fabricated separately and assembled into or onto the disk, or can be placed completely off the disk, most advantageously as a component of the micromanipulation device. The controllers can be used to control the rotation drive motor (both speed, duration and direction), system temperature, optics, data acquisition, analysis and storage, and to monitor the state of systems integral to the disk. Examples of rotational controllers are those using rotation sensors adjacent to the motor itself for determining rotation rate, and motor controller chips (e.g., Motorola MC33035) for driving direction and speed of such motors. Such sensors and chips are generally used in a closed-loop configuration, using the sensor data to control rotation of the disk to a rotational set-point. Similarly, the rotational data from these sensors can be converted from a digital train of pulses into an analog voltage using frequency-to-voltage conversion chips (e.g., Texan Instruments Model LM2917). In this case, the analog signal then provides feedback to control an analog voltage set-point corresponding to the desired rotation rate. Controllers may also use the data encoded in the disk's data-carrying surface in a manner similar to that used in commercially-available compact disk (CD) players. In these embodiments, the digital data read by the laser is used to control rotation rate through a phase-locked loop. The rotation rate information inherent in the frequency of data bits read may be converted to an analog voltage, as described above.

The controllers can also include communication components that allow access to external databases and modems for remote data transfer. Specifically, controllers can be integrated into optical read systems in order to retrieve information contained on the disk, and to write information generated by the analytic systems on the disk to optical data storage sections integral to the disk. In these embodiments it will be understood that both read and write functions are performed on the surface of the disk opposite to the surface comprising the microsystems components disclosed herein.

Information (i.e., both instructions and data, collectively termed "informatics") pertaining to the control of any particular microanalytic system on the disk can be stored on the disk itself or externally, most advantageously by the microprocessor and/or memory of the disk device of the invention, or in a computer connected to the device. The information is used by the controller to control the timing and open/closed state of microvalves on the disk, to determine optimal disk rotational velocity, to control heating and cooling elements on the disk, to monitor detection systems, to integrate data generated by the disk and to implement logic structures based on the data collected.

7. Power Supply

The electrical requirements of systems contained on a disk can be delivered to the disk through brushes that impinge upon connections integral to the disk. Alternatively, an electrical connection can be made through the contact point between the microplatform and the rotational spindle or hub connecting the disk to the rotational motivating means. A battery can be integrated into the disk to provide an on-board electrical supply. Batteries can also be used to power the device used to manipulate the disk. Batteries used with the invention can be rechargeable such as a cadmium or lithium ion cell, or conventional lead-acid or alkaline cell.

Power delivered to the disk can be AC or DC. While electrical requirements are determined by the particular assay system embodied on the disk, voltage can range from microvolts through megavolts, more preferably millivolts through kilovolts. Current can range from microamps to amperes. Electrical supply can be for component operation or can be used to control and direct on-disk electronics.

Alternatively, inductive current can be generated on the disk by virtue of its rotation, wherein current is provided by an induction loop or by electrical brushes. Such current can be used to power devices on the disk.

8. Detectors and Sensors

Detection systems for use on the microsystem platforms of the invention include spectroscopic, electrochemical, physical, light scattering, radioactive, and mass spectroscopic detectors. Spectroscopic methods using these detectors encompass electronic spectroscopy (ultraviolet and visible light absorbance, luminescence, and refractive index), vibrational spectroscopy (IR and Raman), and x-ray spectroscopies (x-ray fluorescence and conventional x-ray analysis using micromachined field emitters, such as those developed by the NASA Jet Propulsion Lab, Pasadena, Calif.).

General classes of detection and representative examples of each for use with the microsystem platforms of the invention are described below. The classes are based on sensor type (light-based and electrochemical). In addition, the detection implementation systems utilizing the detectors of the invention can be external to the platform, adjacent to it or integral to the disk platform.

a. Spectroscopic Methods:

1. Fluorescence

Figure 12A:
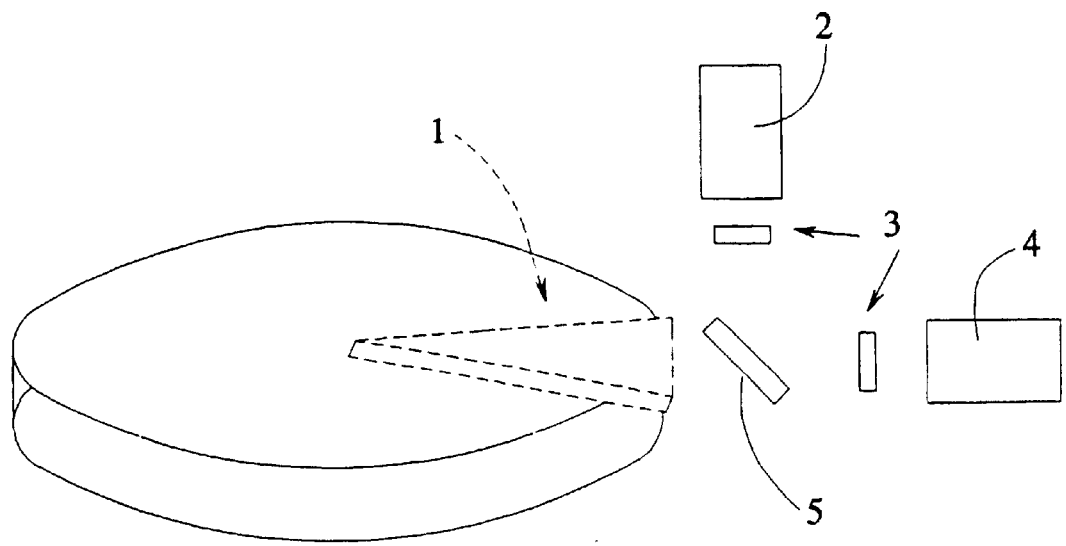
FIGS. 12A and 12B represent two different embodiments of fluorescence detectors of the invention.
Figure 12B:
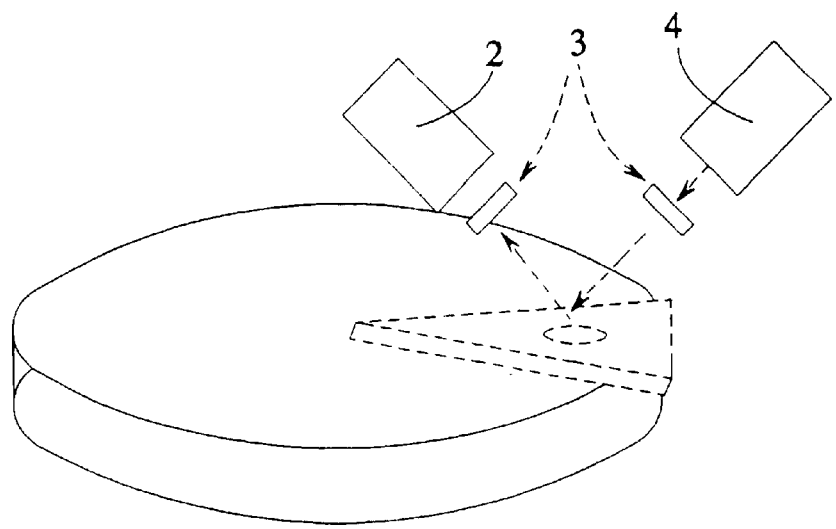

Fluorescence detector systems developed for macroscopic uses are known in the prior art and are adapted for use with the microsystem platforms of this invention. FIGS. 12A and 12B illustrate two representative fluorescence configurations. In FIG. 12A, an excitation source such as a laser is focused on an optically-transparent section of the disk. Light from any analytically-useful portion of the electromagnetic spectrum can be coupled with a disk material that is specifically transparent to light of a particular wavelength, permitting spectral properties of the light to be determined by the product or reagent occupying the reservoir interrogated by illumination with light. Alternatively, the selection of light at a particular wavelength can be paired with a material having geometries and refractive index properties resulting in total internal reflection of the illuminating light. This enables either detection of material on the surface of the disk through evanescent light propagation, or multiple reflections through the sample itself, which increases the path length considerably.

Configurations appropriate for evanescent wave systems are shown in FIG. 12A (see Glass et al.; 1987, *Appl. Optics* 26: 2181–2187). Fluorescence is coupled back into a waveguide on the disk, thereby increasing the efficiency of detection. In these embodiments, the optical component preceding the detector can include a dispersive element to permit spectral resolution. Fluorescence is excitation can also be increased through multiple reflections from surfaces in the device whenever noise does not scale with path length in the same way as with signal.

Another type of fluorescence detection configuration is shown in FIG. 12B. Light of both the fluorescence excitation wavelength and the emitted light wavelength are guided through one face of the device. An angle of 90 degrees is used to separate the excitation and collection optical trains. It is also possible to use other angles, including 0 degrees, whereby the excitation and emitted light travels colinearly. As long as the source light can be distinguished from the fluorescence signal, any optical geometry can be used.

Optical windows suitable for spectroscopic measurement and transparent to the wavelengths used are included at appropriate positions (i.e., in "read" reservoir embodiments of detecting chambers) on the disk. The use of this type of fluorescence in macroscopic systems has been disclosed by Haab et al. (1995, *Anal. Chem.* 67: 3253–3260).

2. Absorbance Detection

Absorbance measurements can be used to detect any analyte that changes the intensity of transmitted light by specifically absorbing energy (direct absorbance) or by changing the absorbance of another component in the system (indirect absorbance). Optical path geometry is designed to ensure that the absorbance detector is focused on a light path receiving the maximum amount of transmitted light from the illuminated sample. Both the light source and the detector can be positioned external to the disk, adjacent to the disk and moved in synchrony with it, or integral to the disk itself. The sample chamber on the disk can constitute a cuvette that is illuminated and transmitted light detected in a single pass or in multiple passes, particularly when used with a stroboscopic light signal that illuminates the detection chamber to a frequency equal to the frequency of rotation or multiples thereof. Alternatively, the sample chamber can be a planar waveguide, wherein the analyte interacts on the face of the waveguide and light absorbance is the result of attenuated total internal reflection (i.e., the analyte reduces the intensity source light if the analyte is sequestered at the surface of the sample chamber, using, for example, specific binding to a compound embedded or attached to the chamber surface; see Dessy, 1989, Anal. Chem. 61: 2191).

Indirect absorbance can be used with the same optical design. For indirect absorbance measurements, the analyte does not absorb the source light; instead, a drop in absorbance of a secondary material is measured as the analyte displaces it in the sample chamber. Increased transmittance therefore corresponds to analyte concentration.

3. Vibrational spectroscopy

Vibration spectroscopic detection means are also provided to generate data from a detecting chamber or "read" section of a microplatform of the invention. Infrared (IF) optical design is analogous to the design parameters disclosed above with regard to absorbance spectroscopy in the UV and visible range of the electromagnetic spectrum, with the components optimized instead for infrared frequencies. For such optimization, all materials in the optical path must transmit IR light. Configuration of the optical components to provide Raman light scattering information are similar to those disclosed in FIGS. 12A and 12B above for fluorescent measurements. However, due to the illumination time needed to generate sufficient signal, the rotation rate of the disk must be slowed, or in some instances, stopped. Depending on the use, static IR or Raman scattering analysis is most advantageously performed off-line in a separate IR or Raman instrument adapted for analysis of the disks of the invention.

4. Light Scattering

Turbidity can also be measured on the disk. Optics are configured as with absorbance measurements. In this analysis, the intensity of the transmitted light is related to the concentration of the light-scattered particles in a sample. An example of an application of this type of detection method is a particle agglutination assay. Larger particles sediment in a rotating disk more rapidly than smaller particles, and the turbidity of a solution in the sample chamber before and after spinning the disk can be related to the size of the particles in the chamber. If small particles are induced to aggregate only in the presence of an analyte, then turbidity measurements can be used to specifically detect the presence of an analyte in the sample chamber. For example, small particles can be coated with an antibody to an analyte, resulting in aggregation of the particles in the presence of the analyte as antibody from more than one particle bind to the analyte. When the disk is spun after this interaction occurs, sample chambers containing analyte will be less turbid that sample chambers not containing analyte. This system can be calibrated with standard amounts of analyte to provide a gauge of analyte concentration related to the turbidity of the sample under a set of standardized conditions.

Other types of light scattering detection methods are provided for use with the Microsystems platforms and devices of the invention. Monochromatic light from a light source, advantageously a laser light source, is directed across the cross-sectional area of a flow channel on the disk. Light scattered by particles in a sample, such as cells, is collected at several angles over the illuminated portion of the channel (see Rosenzweig et al., 1994, *Anal. Chem.* 66: 1771–1776). Data reduction is optimally programmed directly into the device based on standards such as appropriately-sized beads to relate the signal into interpretable results. Using a calibrated set of such beads, fine discrimination between particles of different sizes can be obtained. Another application for this system is flow cytometry, cell counting, cell sorting and cellular biological analysis and testing, including chemotherapeutic sensitivity and toxicology.

b. Electrochemical Detection Methods

Electrochemical detection requires contact between the sensor element and the sample, or between sensor elements and a material such as a gas in equilibrium with the sample. In the case of direct contact between sample and detector, the electrode system is built directly onto the disk, attached to the disk before rotation or moved into contact with the disk after it has stopped rotating. Detectors constructed using a gas vapor to encode information about the sample can be made with the detector external to the disk provided the gas vapor is configured to contact both the sample chamber and the detector. Electrochemical detectors interfaced with the disk include potentiometric, voltammetric and amperimetric devices, and can include any electrochemical transducer compatible with the materials used to construct the microsystem disk.

1. Electric Potential Measurement

One type of electrochemical detection means useful with the Microsystems platforms of the invention is an electrical potential measurement system. Such a system provides a means for characterizing interfacial properties of solutions passed over differently activated flow channels in the instrument. In view of the temperature-controlled nature of the microplatforms of the invention, streaming potentials can also be measured on this device (see Reijenga et a., 1983, *J. Chromatogr.* 260: 241). To produce streaming potentials, the voltage potential difference between two platinum leads in contact with a solution at the inner and outer portions of the disk is measured in comparison with a reference electrode. As fluid flows under controlled centripetal motion through the channel, a streaming potential develops in response to fluid interactions with the disk surfaces in a moving field.

Alternatively, a platinum electrode is used to generate electroluminescent ions (see Blackburn et al., 37: 1534–9). Chemiluminescence is then detected using one of the optical detectors described above, depending on the wavelength of the chemiluminescent signal. Voltametric components are also useful in microsynthetic platforms of the invention to produce reactive intermediates or products.

2. Electrochemical Sensors

Electrochemical sensors are also advantageously incorporated into the disk. In one embodiment, an electrochemical detector is provided that uses a redox cycling reaction (see Aoki et al., *Rev. Polarogr.* 36: 67). This embodiment utilizes an interdigitated microarray electrode within a micromachined chamber containing a species of interest. The potential of one electrode is set at the oxidized potential of the species of interest and the potential of the other electrode is set at the reduction potential of the species of interest. This is accomplished using a dual channel potentiostat, allowing the oxidized and reduced (i.e., redox) chemical state of the sample to be determined, or the chamber may be preset for a particular species. A volume of fluid containing a substance of interest is directed to the chamber. The electrochemically reversible species is then oxidized and reduced by cyclically energizing the electrodes. In this embodiment a molecule is detected by an apparent increase in the redox current. Since non-reversible species do not contribute signal after the first cycle, their overall contribution to the final signal is suppressed. Data analysis software is used to suppress signal due to non-reversible species.

In another embodiment, a multichannel electrochemical detector is provided comprising up to 16 lines of an electrode fabricated in a chamber by photolithography with dimensions resulting in each line being 100 $\mu$m wide with 50 $\mu$m between lines. (see Aoki et al., 1992, *Anal. Chem.* 62: 2206). In this embodiment, a volume of fluid containing a substance of interest is directed to the chamber. Within the chamber each electrode is set a different potential so that 16 separate channels of electrochemical measurement may be made. Additionally, each electrode potential can be swept stepwise by a function generator. This protocol yields information pertaining to redox potential as well as redox current of the substances. This type of analysis also allows identification of molecules via voltammogram.

c. Physical Methods

Physical detection methods are also provided for use with the disks of the invention. For example, the disk can be used as a viscometer. Microchannels containing fluid to be tested advantageously contain a bead inserted on the disk. The motion of the bead through the fluid is analyzed and converted into viscosity data based on standards developed and stored in microprocessor memory. (see Linliu et al., 1994, *Rev. Sci. Instrum.* 65: 3824–28).

Another embodiment is a capacitive pressure sensor (see Esashi et al., 1992, *Proc. Micro Electro Mechanical Systems* 11: 43). In this embodiment, silicon and glass substrates are anodically bonded with hermetically sealed reference cavities. Pressure may be detected by the capacitance change between the silicon diaphragm and an aluminum electrode formed on the glass. A capacitance-to-frequency converter output of a CMOS circuit can be integrated on the silicon substrate or contained in controlling electronics off the disk.

By judicious placement of pressure sensors, the pressure due to centrifigation can be determined at any position on the disk. In conjunction with the microchannel diameter information and the pattern of orientation of the channels on the disk, pressure data can be used to determine flow rates at a particular rotational speed. This information can then be used by the microprocessor to adjust disk rotational speed to control fluid movement on the disk.

Surface acoustic wave (SAW) devices are also provided as components of the Microsystems platforms of the invention. These devices can be placed above the disk to detect head-space gases, or incorporated in the fluid channel on the instrument. When placed in the fluid system, the SAW is used to detect density changes in the solution, indicative of changing buffer, reagent or reactant composition (see Ballantine et al., 1989, *Anal. Chem.* 61: 1989).

Volatile gases on the disk or trapped in the head-space surrounding the disk can be monitored in several ways. For example, a Clark electrode positioned in contact with either the solution of the gases above the disk may be used to detect oxygen content. (Collison et al., 1990, *Anal. Chem.* 62: 1990).

d. Radioactive Detection Components

Microsystems platforms of the invention also can incorporate radioactivity detectors. Radioactive decay of an analyte or synthetic product on a disk of the invention can be detected using a CCD chip or similar single channel photodiode detector capable of integrating signal over time. Alternatively, radioactivity can be determined directly by placing a solid state detector in contact with a radioactive analyte. (see Lamture et al., 1994, *Nucleic Acids Res.* 22: 2121–2125).

Modular Structures

Analytic systems provided as components of the platforms of the invention typically consist of combinations of controllers, detectors, buffer and reagent reservoirs, chambers, microchannels, microvalves, heaters, filters, mixers, sensors, and other components. Components that constitute an analytic system on the disk can be composed of one or more of the following: complete integral systems fabricated entirely on the disk; complete integral systems fabricated as a component and assembled into or onto the disk; a subset of components fabricated directly onto the disk and interfaced with a subset of components that are fabricated as a component and assembled into or onto the disk; components that interface with the disk externally through a synchronously spinning disk; and components that interface with the spinning disk from a position that remains stationary in relation to the disk (e.g., the rotational spindle).

Methods and Uses

Because of its flexibility, the invention offers a myriad of possible applications and embodiments. Certain features will be common to most embodiments, however. These features include sample collection; sample application to disk, incorporating tests of adequacy at the time of sample application; a variety of specific assays performed on the disk; data collection, processing and analysis; data transmission and storage, either to memory, to a section of the disk, or to a remote station using communications software; data output to the user (including printing and screen display); and sample disk disposal (including, if necessary, disk sterilization).

Sample or analyte is collected using means appropriate for the particular sample. Blood, for example, is collected in vacuum tubes in a hospital or laboratory setting, and using a lancet for home or consumer use. Urine can be collected into a sterile container and applied to the disk using conventional liquid-transfer technology. Saliva is preferably applied to the disk diluted with a small volume of a solution of distilled water, mild detergent and sugar flavoring. This solution can be provided as a mouthwash/gargle for detecting antigens, biological secretions and microorganisms. Alternatively, a small sack made of a fishnet polymer material containing the detergent formulation and a chewable resin can be chewed by a user to promote salivation, and then removed from the mouth and saliva recovered and applied conventionally. Amniotic fluid and cerebrospinal fluid are, of necessity, collected using accepted medical techniques by qualified personnel.

Environmental and industrial samples are collected from ground water or factory effluent into containers produced to avoid leaching contaminants in the sample. Soil samples are collected and mixed with a solvent designed to dissolve the analyte of interest. Industrial applications, such as pyrogen screening, are accomplished using specially-designed sample ports.

Figure 13A:
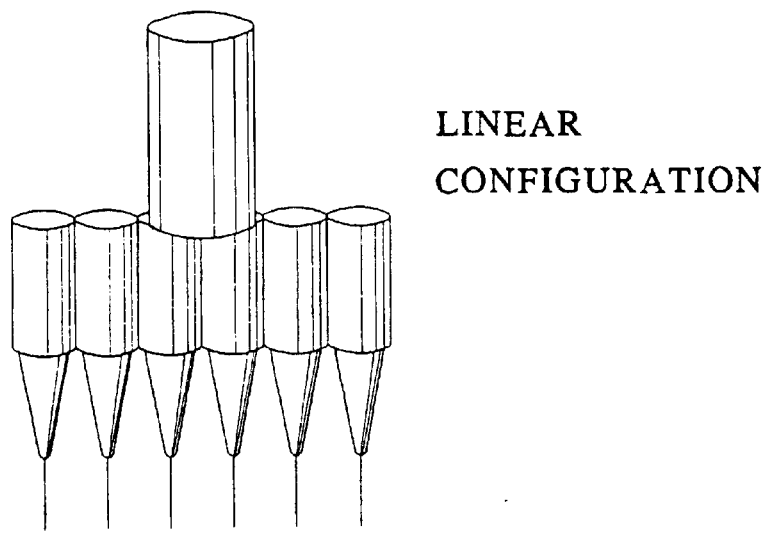
FIGS. 13A, 13B and 13C are a schematic diagrams of a multiple loading device for the disk.
Figure 13B:
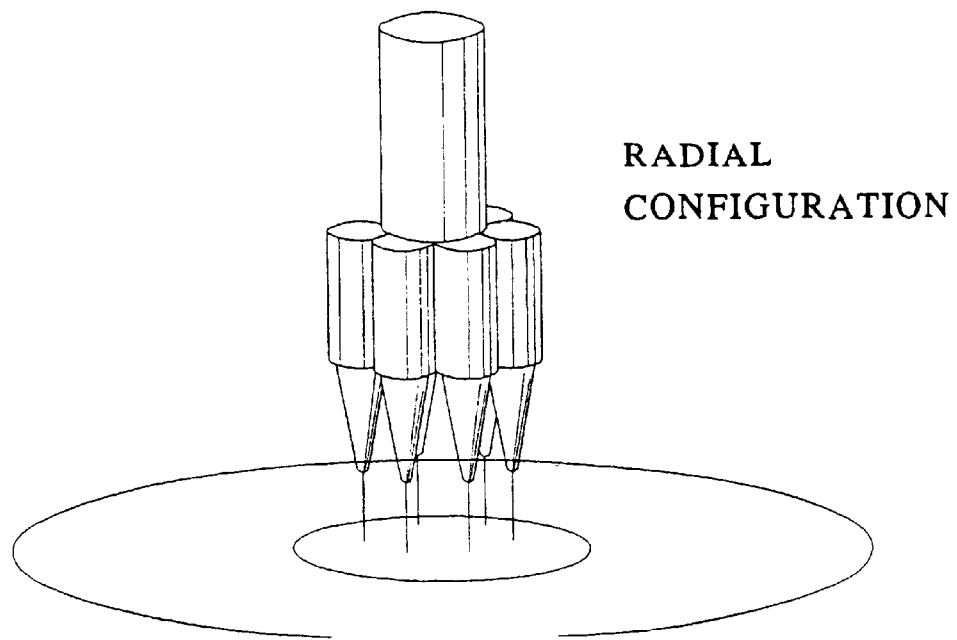
Figure 13C:
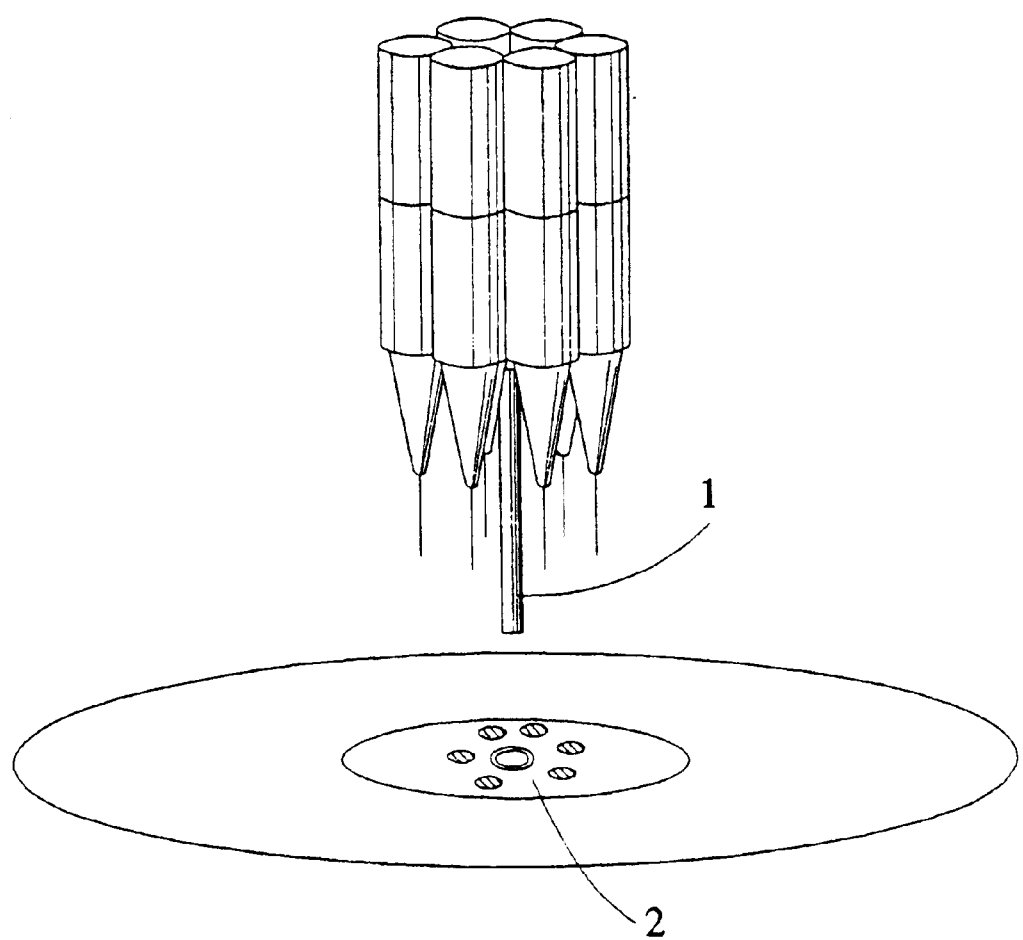
Figure 14A:
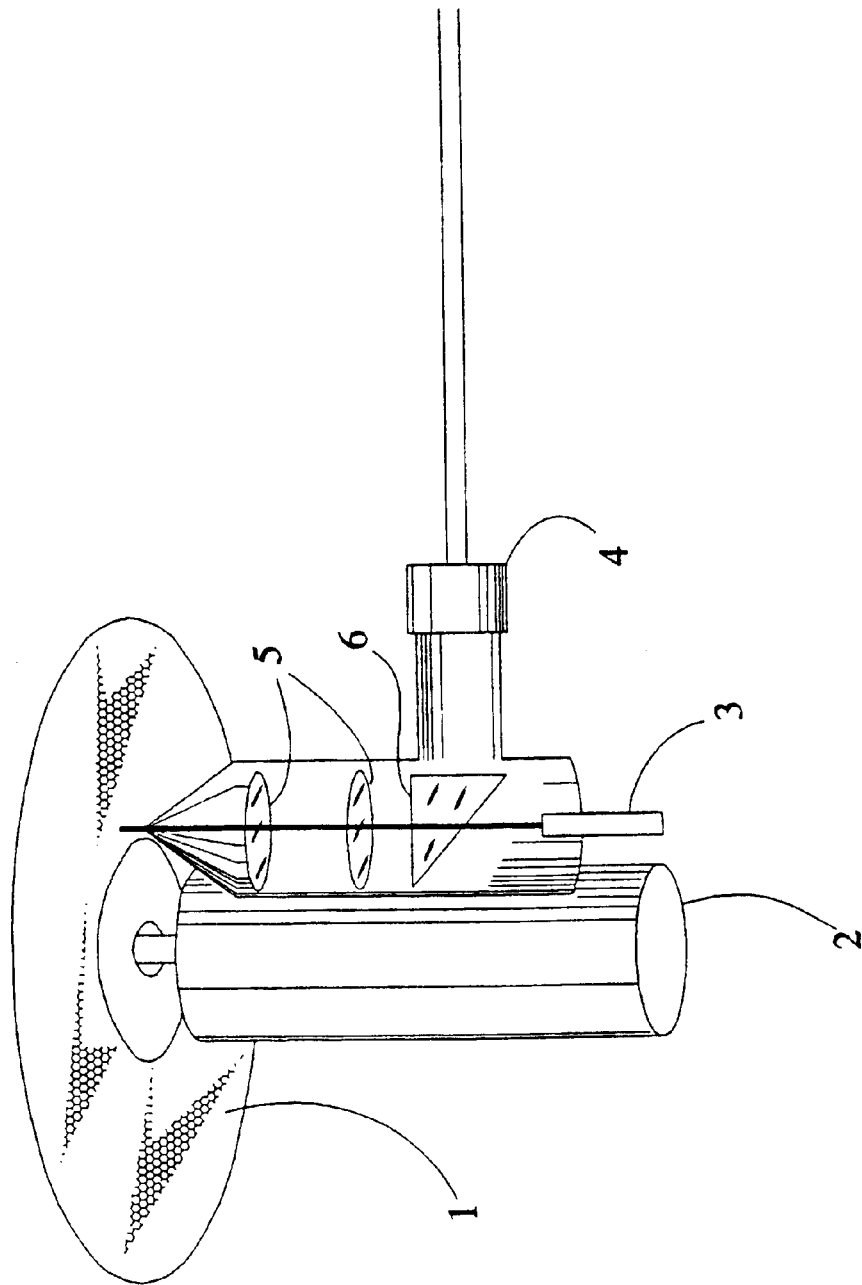
FIGS. 14A through 14F illustrate laser light-activated CD-ROM capability of the disk of the invention.
Figure 14B:
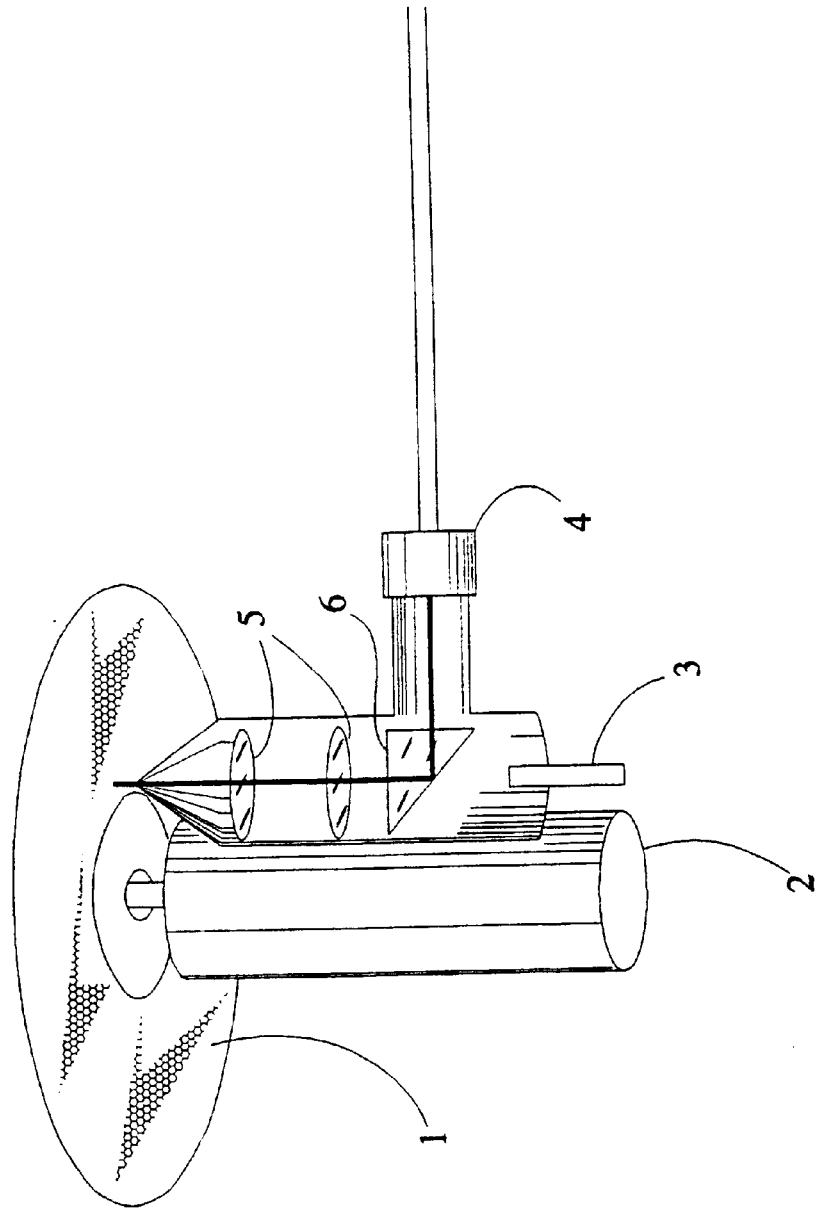
Figure 14C:
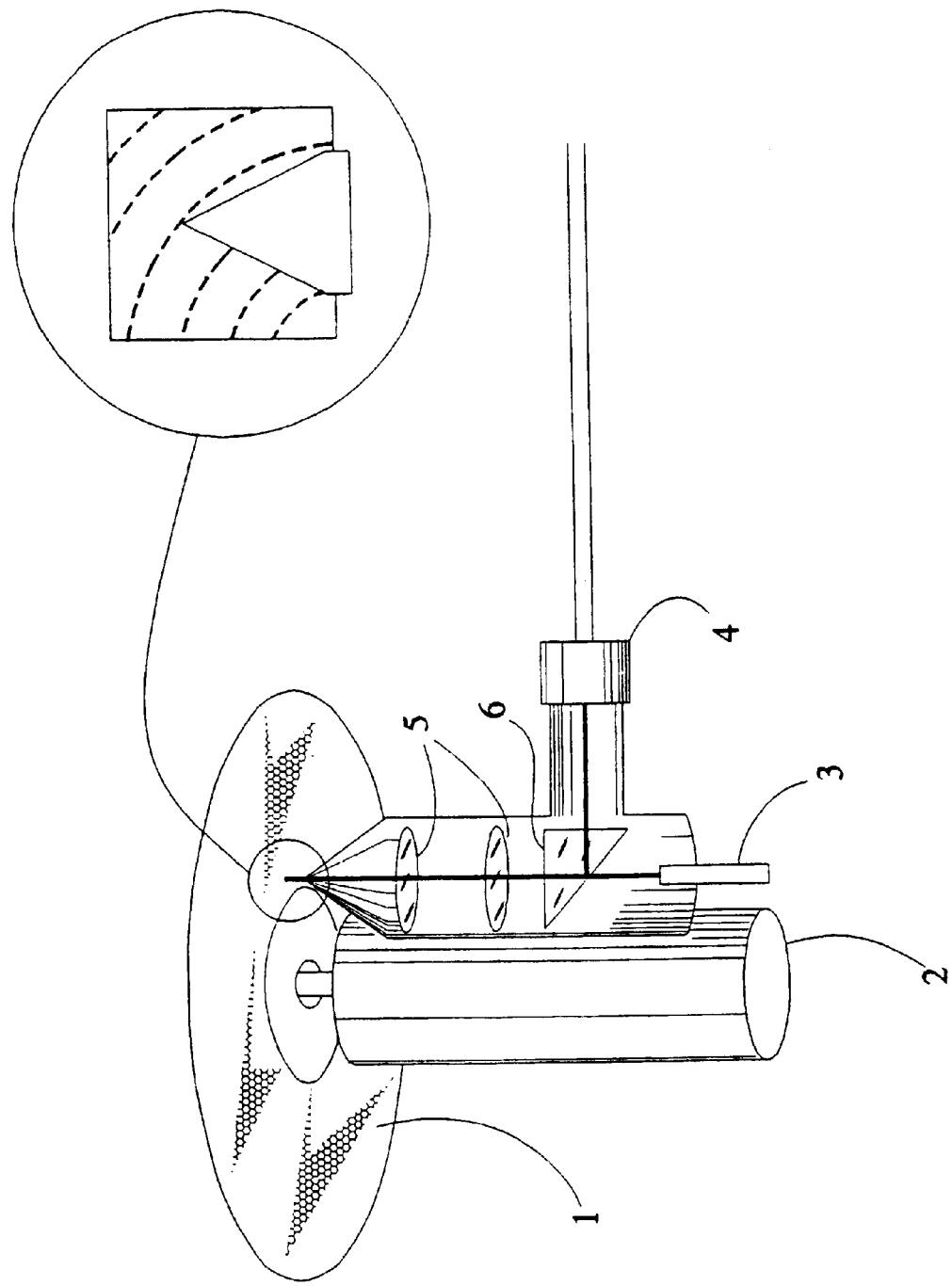
Figure 14D:
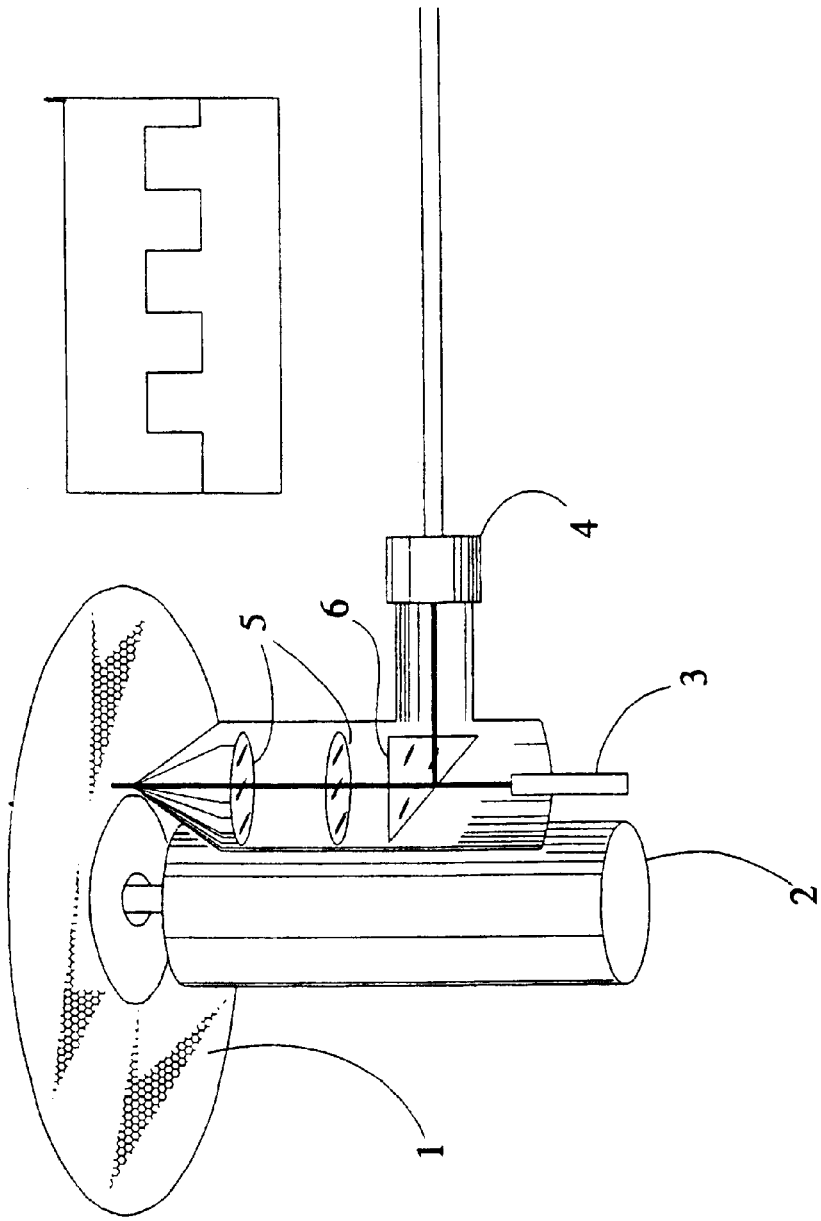
Figure 14E:
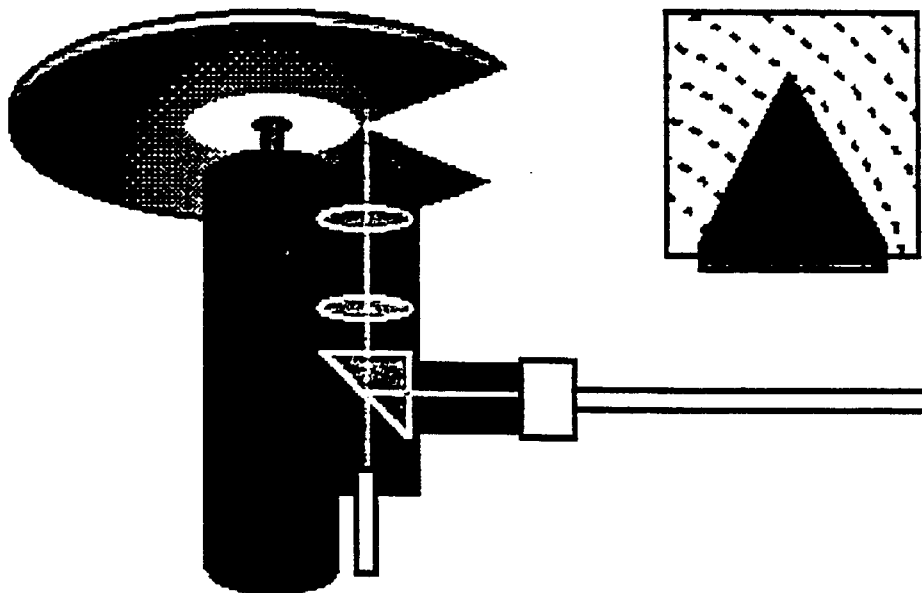
Figure 14F:
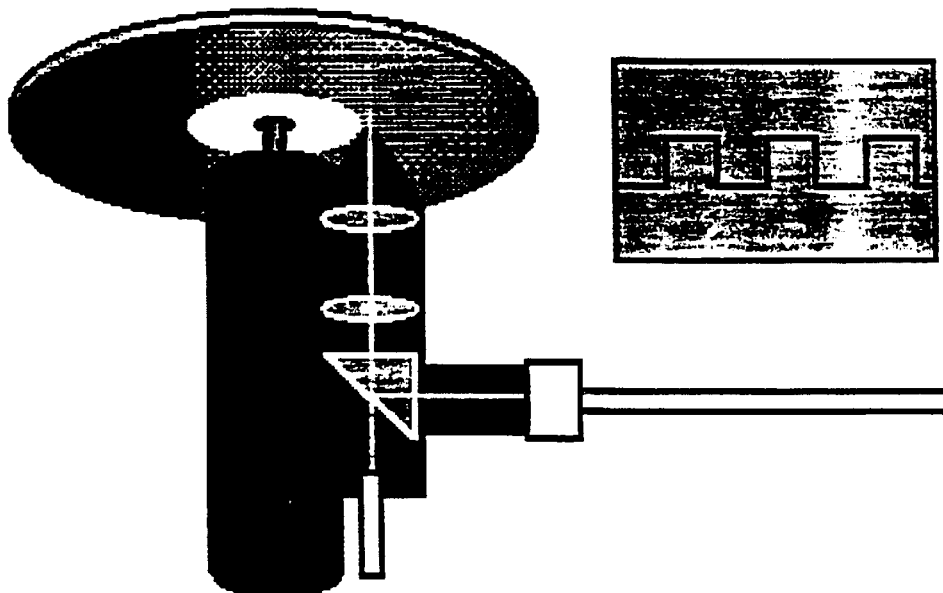

Sample or analyte is loaded onto the disk by the user. Sample is optimally loaded onto the disk at a position proximal to the center of rotation, thereby permitting the greatest amount of centripetal force to be applied to the sample, and providing the most extensive path across the surface of the disk, to maximize the number, length or arrangement of fluid-handling components available to interact with the sample. Multiple samples can be applied to the disk using a multiple loading device as shown in FIGS. 13A through 13C. In this embodiment of a multiple loading device, a multiplicity of pipette barrels are equally spaced and arranged radially. The pipettes are spaced to provide that the tips of the pipettes fit into access ports on the surface of the disk. The tips can be simple pins that hold a characteristic volume of sample by virtue of a combination of surface properties and fluid characteristics. Alternatively, the tips can be conventional hollow tubes, such as capillary or plastic conical tips, and the fluid manipulated manually in response to positive or negative pressure, as with a manual or automatic pipetting device. The loader can be operated manually or by robotic systems. The barrels can also be arrayed in a flexible arrangement, permitting the tips to address a linear array in one configuration and a radial array in another. In each embodiment, the loader comprises an alignment device to ensure reproducible placement of the loading tips on the disks of the invention.

Loaders are designed specifically for the substances being investigated. Examples include medical uses (where the samples include blood, body fluids including amniotic fluid, cerebrospinal, pleural, pericardial, peritoneal, seminal and synovial fluid, in addition to blood, sweat, saliva, urine and tears, and tissue samples, and excreta), and environmental and industrial substances (including atmospheric gases, water and aqueous solutions, industrial chemicals, and soils). Loading devices are also advantageously compatible with standard blood-handling equipment, such a vacuum tubes fitted with septa, and access sample therein by piercing the septa. Loading devices are also compatible with seat collection devices and means, such as lancets, for obtaining a small blood sample. A disk may also have integral lancets and rubber seals in order to sample blood directly.

Dynamic as well as static loading of the disk is envisioned as being within the scope of the invention (see Burtis et al., 1974, *Clin. Chem.* 20: 932–941).

As the invention comprises the combination of a Microsystems platform as described above and a micromanipulation device for manipulating this platform to impart centripetal force on fluids on the platform to effect movement, arrangement of components can be chosen to be positioned on the disk, on the device, or both. Mechanical, electronic, optico-electronic, magnetic, magneto-optic, and other devices may be contained within the disk or on disk surface. Some on-disk devices have been described above in detail; additionally, the disk may contain electronic circuitry, including microprocessors for coordination of disk functions, and devices for communication with the disk manipulation device or other devices. The disk optimally comprises detectors and sensors, or components of these devices and energy sources for various detection schemes (such as electric power supplies for electrochemical systems, electromagnetic radiation sources for spectroscopic systems), or materials, such as optically-transparent materials, that facilitate operation of and data generation using such detectors and sensors; actuators, including mechanical, electrical, and electromagnetic devices for controlling fluid movement on the disk, including valves, channels, and other fluid compartments; communications and data handling devices, mediating communications between the disk and the player/reader device, using electromagnetic (laser, infra-red, radiofrequency, microwave), electrical, or other means; circuitry designed for controlling procedures and processes on the disk, including systems diagnostics, assays protocols and analysis of assay data, These are provided in the form of ASICs or ROM which are programmed only at the point-of-manufacture; FPGA's EPROM, flash memory (UV-erasable EPROM), or programmable IC arrays, or similar arrays programmable by the user through the platform manipulation device or other device. Also included in the components of the invention are CPU and microprocessor units and associated RAM operating with an assembler language or high-level language programmable through disk communications, and components for mediating communication with other devices, including facsimile/modem communications with remote display or data analysis systems.

Figure 15:
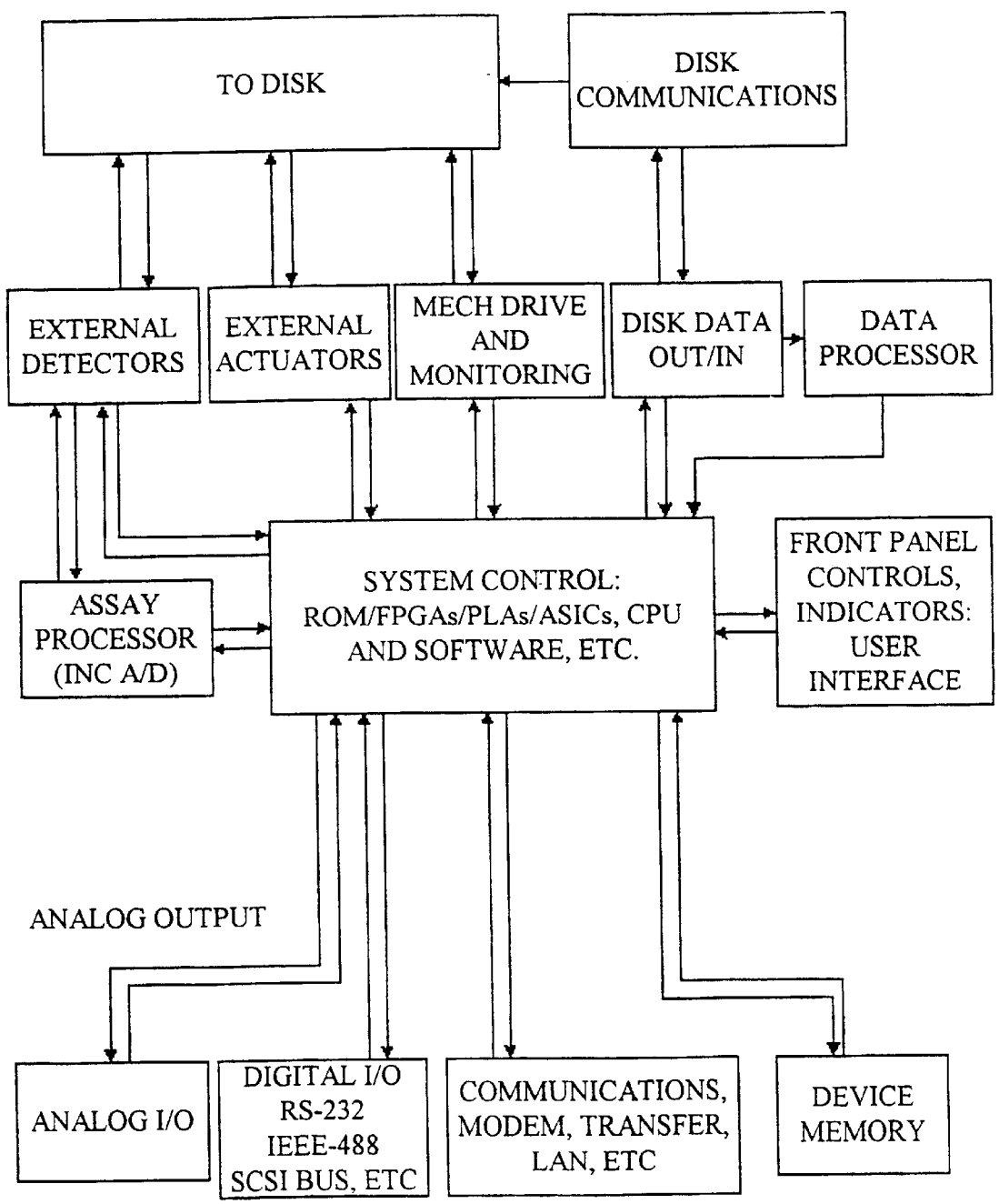
FIG. 15 is a flow diagram of the processor control structure of a player/reader device of the invention.

Off-disk devices comprise the microplatform micromanipulating device itself and other devices which can access information, write information, or initiate processes on the disk. FIG. 15 illustrates the categories of devices and sub-devices which are part of the micromanipulation device, and indicates how there components interact. "Interaction" is used herein to mean the exchange of "data" between the disk and device, or among the components of the device itself. The relationship between these components is here described, followed by detailed examples of the components.

These include the mechanical drive and circuitry for rotation monitoring and control, overall system control, data read/write devices, external detectors and actuators for use with the disk, dedicated data and assay processors for processing encoded data and assay data, a central processor unit, a user interface, and means for communicating to the disk, the user, and other devices. Mechanical drive and associated circuits include devices to control and monitor precisely the rotation rate and angular position of the disk, and devices to select and mount multiple-disks from a cassette, turntable, or other multiple-disk storage unit. System control units provide overall device control, either pre-programmed or accessible to the user-interface. Disk data read/write devices are provided for reading encoded information from a disk or other medium. Optimally, write-to-disk capabilities are included, permitting a section of the disk to contain analytical data generated from assays performed on the disk. This option is not advantageous in uses of the disk where the disks are contaminated with biological or other hazards, absent means (such as sterilization) for neutralizing the hazard. The device can also include external actuators comprising optical magneto-optic, magnetic and electrical components to actuate microvalves and initiate processes on the disk, as well as external detectors and sensors or components of detectors and sensors that operate in concert with other components on the disk, including analytic and diagnostic devices. Certain of these aspects of the disk micromanipulating device are illustrated in FIGS. 14A through 14F.

Disk data processors are also advantageously incorporated into the devices of the invention which enable processing and manipulation of encoded disk data. These components include software used by the micromanipulator CPU, programmable circuits (such as FPGAs, PLAs) and dedicated chipsets (such as ASICs). Also provided are assay processors for processing data arising from events and assays performed on the disk and detected by external detectors or communicated from on-disk components. The device also advantageously comprises a central processing unit or computer which will allow processing of disk data and assay results data-analysis (through pre-programming); additionally, conventional computer capabilities (word-processing, graphics production, etc.) can be provided.

A user interface, including keypads, light-pens, monitors, indicators, flat-panel displays, interface through communications options to host-devices or peripheral devices, and printers, plotters, and graphics devices are provided as components of the microplatform micromanipulating devices of the invention. Communication and telecommunications are provided through standard hard-wired interfaces (such as RS-232, IEE-488M SCSI bus), infra-red and optical communications, short-or long-range telecommunications ("cellular" telecommunications radio-frequency), and internal or external modem for manual or automated telephone communications.

Disk information comprises both software written to the disk to facilitate operation of the microsystem assays constructed thereupon, and assay data generated during use of the microsystem by the user. Disk information includes material written to the disk (as optically encoded data) and information inherent to the disk (e.g., the current status of a valve, which can be accessed through magnetic pickup or through the reflective properties of the coating material at the valve-position) Data written to the disk may include but is not limited to the audio/video/test and machine format information (e.g., binary, binhex, assembler language). This data includes system control data used for initiation of control programs to spin the disk, or perform assays, information on disk configuration, disk identity, uses, analysis protocols and programming, protocols descriptions, diagnostic programs and test results, point-of-use information, analysis results data, and background information. Acquired data information can be stored as analog or digital and can be raw data, processed data or a combination of both.

System control data include synchronization data to enable the micromanipulation device to function at the correct angular velocity/velocities and accelerations and data relating to physical parameters of disk. Disk configuration and compatibility data include data regarding the type of disk (configuration of on-disk devices, valves, and reagent, reaction and detection chambers) used to determine the applicability of desired testing protocols; this data provides a functional identity of the type of disk and capabilities of the disk. It can also form part of an interactive feedback system for checking microsystem platform components prior to initiation of an assay on the disk. Disk identify and serial numbers are provided encoded on each disk to enable exact identification of a disk by fabrication date, disk type and uses, which data are encoded by the manufacturer, and user information, which is written to the disk by the user. Also included in disk data is a history of procedures performed with the disk by the user. Also included in the disk data is a history of procedures performed with the disk, typically written for both machine recognition (i.e., how many and which assays remain unused or ready for use), as well as information written by the user.

Figure 30:
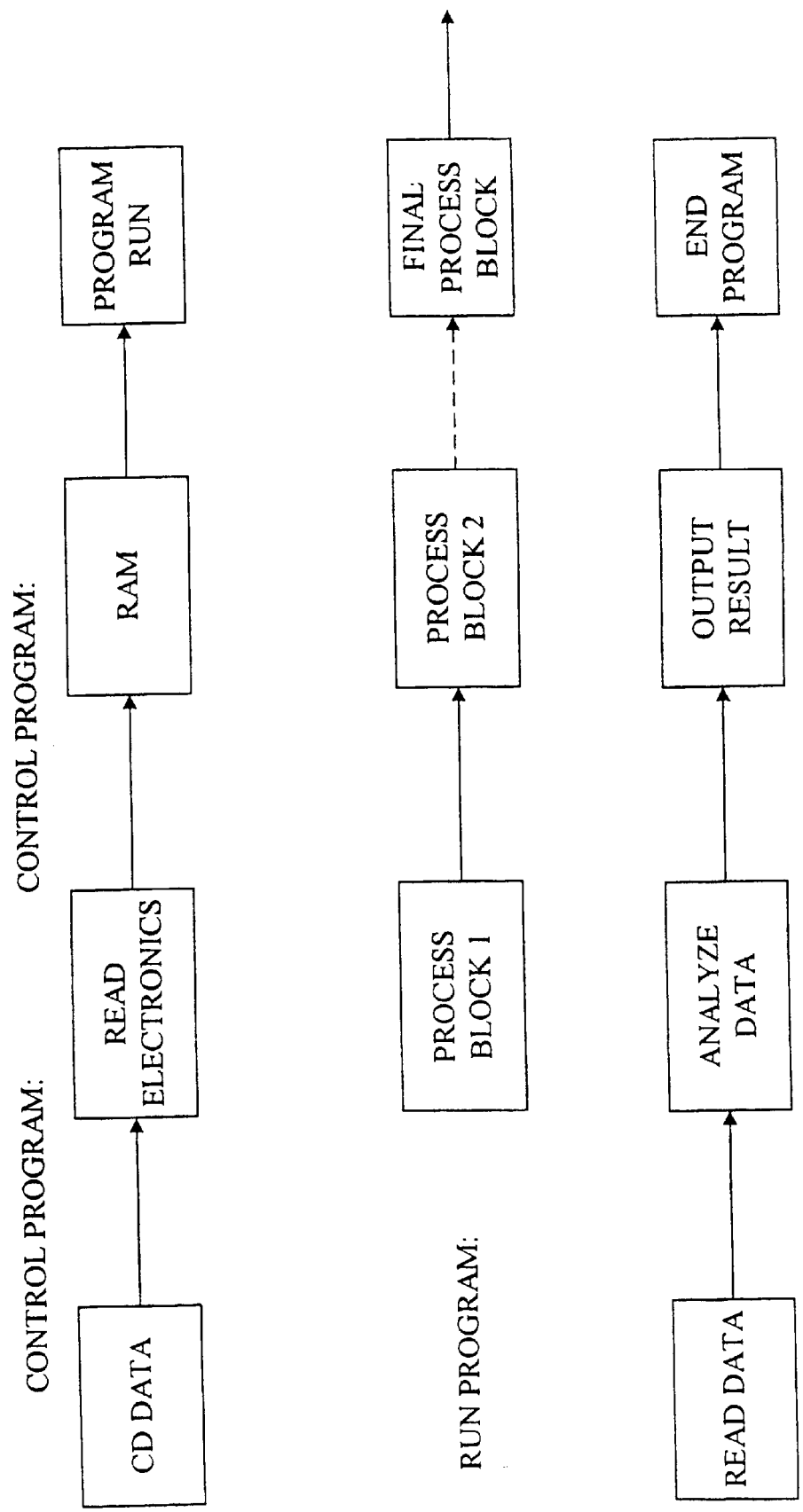
FIG. 30 is a block diagram of process flow in controlling informatics of the invention.
Figure 31A:
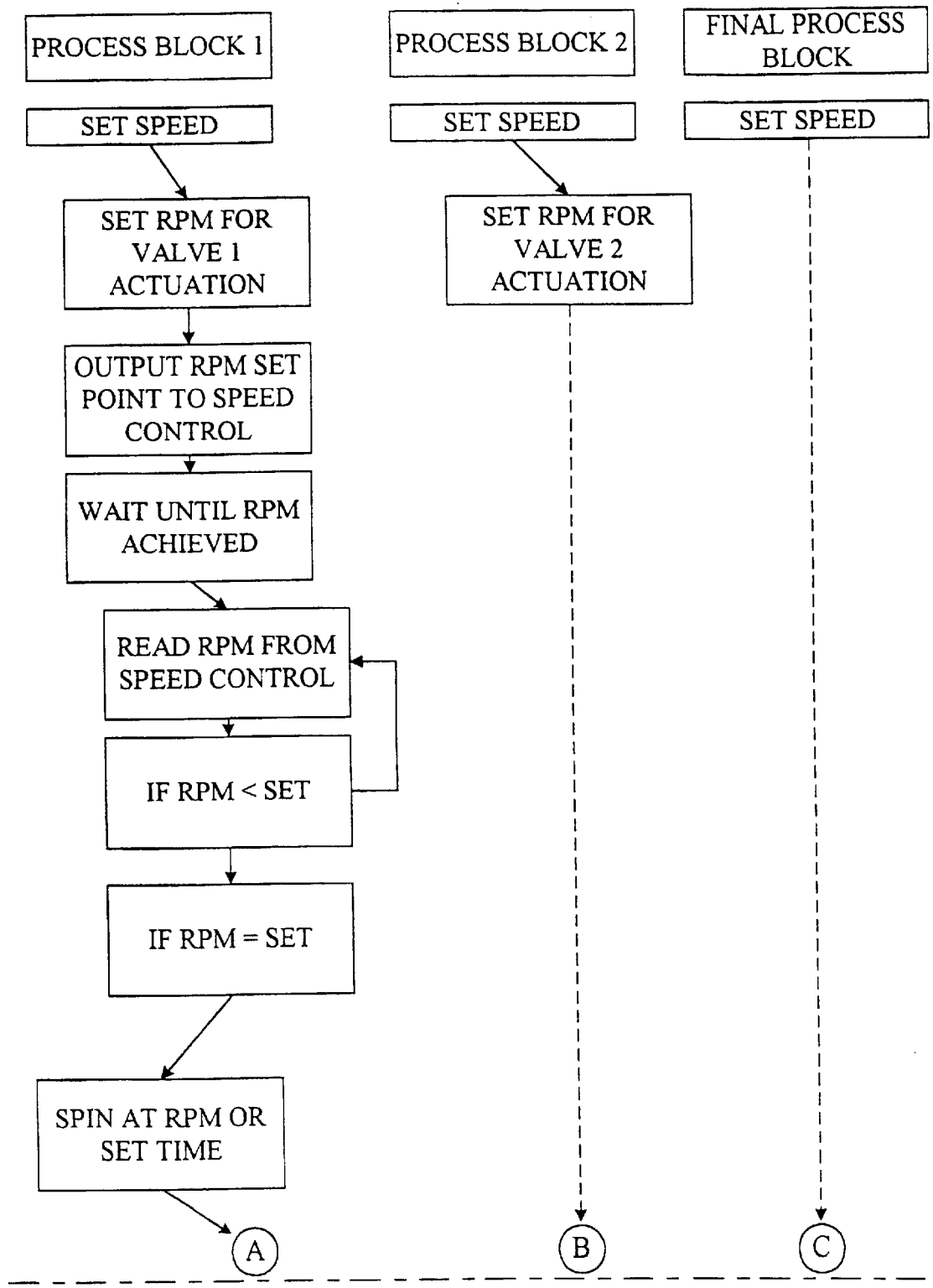
FIGS. 31A and 31B are a more detailed schematic diagram of controlling informatics of the invention.
Figure 31B:
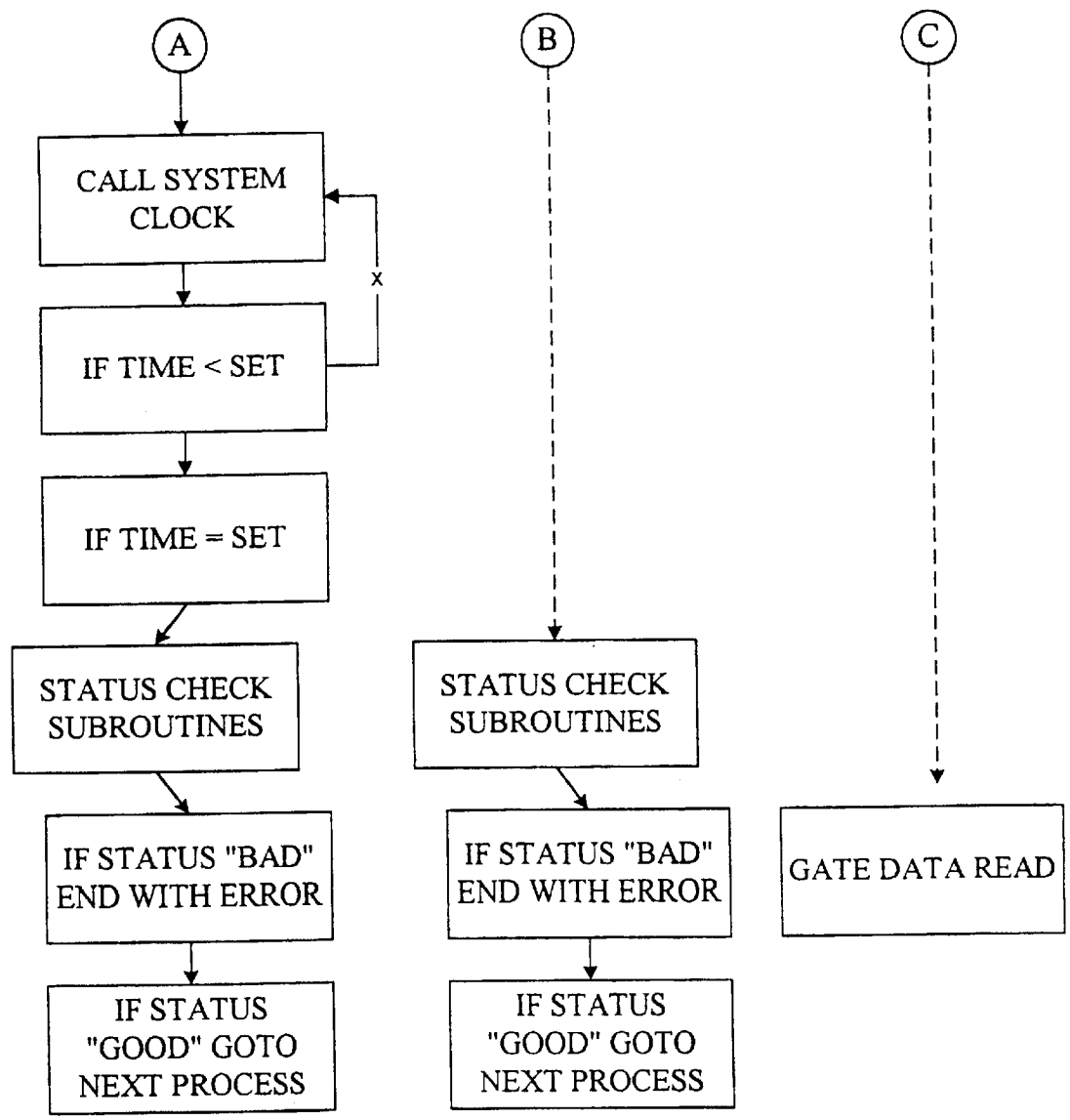
Figure 32A:
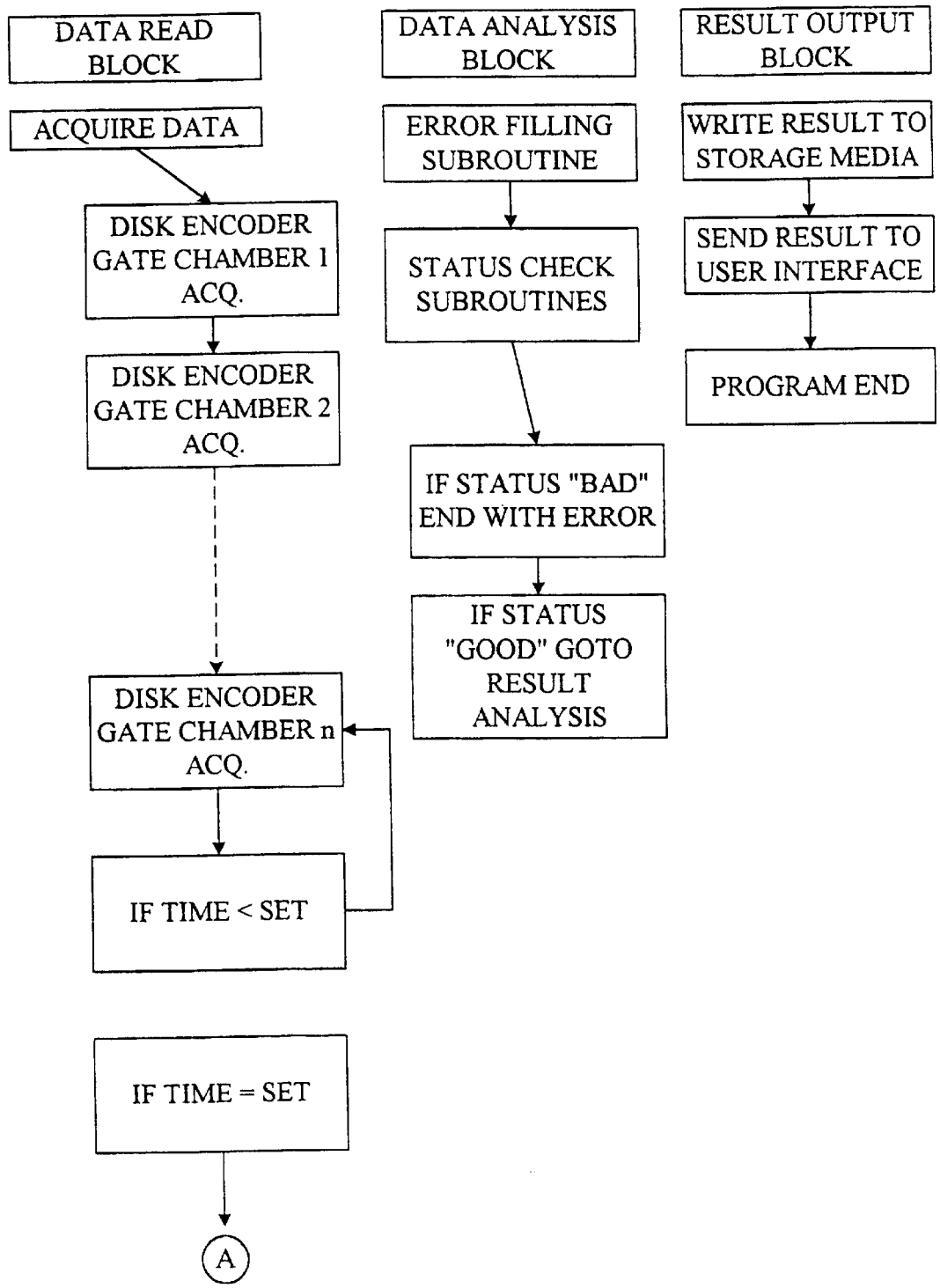
FIGS. 32A and 32B are a more detailed schematic diagram of controlling informatics of the invention.
Figure 32B:
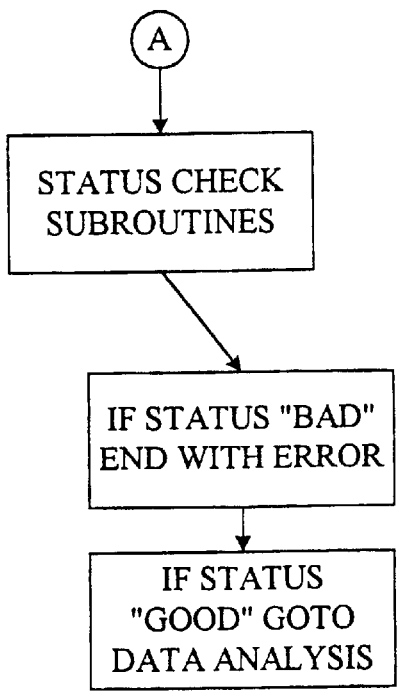

FIGS. 30–32 display the action of software encoded on the disk used for controlling the device driving the disk. FIG.

30 displays the process flow. The control program, encoded as data on the disk, is read through conventional means, for example, by the laser of an optical storage medium (such as a compact disc or "Laservision" disc) and decoded in the conventional way for loading into the random access memory (RAM) of the micromanipulation device. This program is then executed. In some applications, execution of the program to completion will be automatic and without active interaction with the user. In other applications the user will be presented with a variety of options (typically, as a menu) for running the program. As an example, user choices, such as whether to run an exhaustive or limited set of diagnostics, test procedures, analyses, or other disk functions, or to determine the extent of detail and the method of reporting test results are provided through the user interfaces.

FIGS. 31 and 32 show one specific set of programmed steps for performing assays using the capillary microvalves disclosed above; other arrangements of steps within the program will be apparent to one of ordinary skill and readily integrated, for example, for sending signals to activate microvalves and other actuators. The program disclosed here consists of blocks in which different rotation rates are set for varying amounts of time, allowing for capillary valving, mixing, and incubation; mixing program blocks, which (for example) put the spindle motor through an oscillatory acceleration and deceleration, are possible but not shown. These program blocks consist of outputting commands to various electronic devices (motor, detectors, etc.) and reading data from devices, yielding a measure of device and process status. Provisions are shown in the program for halting the program if the status is "bad" (such as motor cannot reach appropriate speed, door to device cannot close, no power detected in light source for spectroscopic measurements). This condition can lead to a program halt (as shown) or send the program back to the user for further instructions via the interface.

The program shown here additionally incorporates data acquisition, data analysis, and data output blocks. The particular acquisition process here involves using an encoded signal on the disk-for example, an optical signal associated with a detection chamber passing the detector-to gate acquisition of data. In this way, data is acquired for a specific time when detection chambers are in proximity to the detector. It is also possible to continuously take data and use features in that data-for example, the shape of the signal as a function of time, which might look like a square wave for an array of windows on an otherwise opaque disk—to determine what parts of the data are useful for analysis. Data analysis could include non-linear least-squares fitting, linear regression of data as function of time, or end-point analysis (data at an end-point time for a reaction), as well as other methods. Data output may be in the form of "yes/no" answers to the user interface, numeric data, and storage to internal or external storage media.

All component parts of this program need not be contained on the disk. For example, the program can be resident in the computer and designed to read the disk itself to obtain the rotation velocity profiles necessary for using the disk. All other aspects of the program—such as when and how to read and analyze data—can be part of a dedicated program or read from other media.

Analysis/test protocol data are descriptions of tests and analyses which can be performed with a disk. These data can be a simple as a title given the disk, or can contain a detailed description of disk use, data analysis and handling, including test protocols and data analysis protocols. Analysis/test protocol programming is provided that can be used as systems-specified subroutines in more general software schemes, or can be fed into programmable logic so that the device can perform the desired analyses. Analysis/protocol descriptions are provided, as audio, video, text or other descriptions of analytic processes performed on disk, including background information, conditions for valid use, precautions, and other aspects.

Encryption and verification data/programming is provided to ensure the security of the programming and data generated in the analyses performed by the disk. Encryption/ de-encryption routines are used to restricted access to data contained on the disk. Such routines also used in medical diagnostic applications.

System self-diagnostics are also provided. System diagnostics include diagnostic test results on detector function, status of reagent chambers, valves, heating elements, and other components, stored in disk-memory or written to the disk by a separate device used at the time of diagnostics.

Point-of-use information is encoded on the disk at its point-of-use (sample loading, e.g.) in the form of video, audio, or text images, including, for example location, time and personnel. Also included in point of use information is test result data, recorded by the disk itself or by a disk player/reader at the time these procedures were performed.

Certain data are inherent to the disk and are accessible through the micromanipulation device. These include sample adequacy test data, which records the presence or absence of samples or reagents at appropriate reservoirs and other fluid handling regions of the disk, and can be accessed through external detectors and sensors. Valve status is also recorded, including the record of the change in valve status during a procedure performed in the disk. Valve status is determined, for example, by using magnetic pickups in the device applied to magnetic valve mechanisms; status can also be visible through optical windows on the disk. The presence of radioactive, chemical or biological contaminants on the external surface of the disk can be recorded upon detection by sensors comprising the device, optimally resulting in a warning message delivered to a user interface such as a display or print-out.

Disk data and information are stored using a variety of media, including both the recording medium of the disk material (i.e., reflective properties of an optically-read disk, most preferably a read/write CD-ROM) and by the device itself using electronic components. Information is encoded using conventional or modified technologies used for computer information storage. Video, audio, and text information is digitized using methods developed by the digital video, audio, and computer industries. Analog signals arising from test procedures, such as a signal observed in a photodiode detector or photomultiplier tube, are converted through analog-to-digital conversion regimes or may be supplied in raw or amplified form through external jacks for processing off-disk or off-device. Various embodiments of the disk manipulation device of the invention include the capacity to both read and write data to the disk or to use read-only data from any of these media types. Encryption and authentication codes can be used for security purposes. Disk data storage media include optical media, utilizing reflecting/non-reflecting flats and pits on a surface, using technology adapted from audio CD, CD-ROM, and "Laserdisc" technology, and barcodes. Magnetooptic and magnetic media are also within the scope of this aspect of the invention, using conventional computer magnetic storage media. Electronic data storage means are also provided, using the status of internal arrays of electronic components (FPGAs, PLAs, EPROM, ROM, ASICs, IC networks) for information handling. Chemical recording means, including simple chromatographic staining of a detector section or chamber of the device, is also disclosed to provide a simple visual record of a test result. This simple chemical recording means provides an avenue to at-home diagnostic without the need for an expensive device more sophisticated in capabilities than required to determine an assay amenable to simply the presence or absence of chemical markers.

Software and Communications

Software providing the information and instruction set for microsystem performance, quality control, data acquisition, handling and processing, and communications is included within the scope of this invention. For the purposes of this invention, such software is referred to as "machine language instructions." Control and analysis software is advantageously provided in high-level languages such as C/C++, Visual Basic, FORTRAN or Pascal. Drivers are provided for interface boards (either internal to the device or to a host computer interfaced with the device) which translates instructions on the host computer's bus into micromanipulator commands. Additionally, drivers for experiment-control software such as LabView may be created, again using conventional, industry-standard interface protocols. These applications are most preferably capable of being run on a number of popular computer platforms, including UNIX/Linux, X-windows, Macintosh, SGI, etc.

Control and analysis can also be performed using dedicated chipsets and circuitry, ROM, and EPROM. For example, test validity can be insured (at least in part) through the use of ROM-based test procedures, in which all programming is performed at the point-of-manufacture without possibility of end-user corruption. Separate application software can also be developed so that data from a disk-player can be analyzed on non-controller platforms, using available applications (such as Excel, Clarisworks, SigrnaPlot, Oracle, Sybase, etc.).

Because some applications of the disk technology disclosed herein involve important questions related to human health, disk diagnostic software must be able to analyze diagnostics of the disk, its contents (samples, reagents, devices), the player, and analysis software to ensure result validity. Types of information used by this diagnostic software include sample adequacy and flow, verification of disk format and software/test procedure compatibility, on-and off-disk software tests, quality control monitoring of disk manufacture (for example, channel placement and alignment), viability, positioning and functionality of on-disk and off-disk sensors and detectors, diagnostics of player communications and microprocessor, microprocessor/CPU, power stability, etc.

Diagnostics of mechanical and electronic components are performed in ways familiar to those proficient in the art. Software self-diagnostics are achieved using checklist/verification of software routines and subroutines to detect incompatibility with system hardware (from either the micromanipulation device or the disk) or with other components of system software.

Sample-related disk diagnostics include assays of flow, sample adequacy, and reagent adequacy, type and quality for the assay to be performed. Device-related disk diagnostics include checks of detector/sensor function, electronic components self-test, valve control, and thermal control tests. Software diagnostics provide self-testing of software components encoded in the disk or in the device, corruption safeguards, read-only and read-write tests. Disk format is also checked using disk diagnostics, ensuring that the disk format and assay type are properly read and are in agreement with the protocol held in the device memory.

On-disk software includes read-only software, available as ROM, specifically CD-ROM, for diagnostics, assay control and data analysis. Read-only software is designed for specific procedures and processes which cannot be altered and insure proper usage of the disk and fail-safe against corruption by the user. Software may also be embodied within the encoding medium (optical, magnetic, etc.) or an alternate medium (such as barcodes). Re-programmable software (such as t FPGAs, PLAs, EPROMs, or IC arrays) can be re-programmed by the disk micromanipulation device or devices designed for this purpose. Similar types of software are alternatively provided on-device. In either case, a user-interface through keyboard, touchpad and/or display components of the device is provided.

Applications software is provided in read-only or re-programmable software formats. Included in this component of the fluidics micromanipulation apparatus of the invention is software that can be read from standard computer data storage medium. Examples include medical or analytic diagnostic programs reliant on integrated data-bases which are contained within disk or device memory, or that can be accessed from networked workstations, or access on-line services, such as a newsletter and news services, and software for the production and analysis of images, including pattern recognition, statistical analysis software, etc.

Integration of control and applications software can be made through the use of either a unique operating system developed for the disk and micromanipulator of the invention, or by adaptation of existing OS. Optimally, the OS uses authoring software to combine text, graphics, video and audio into an easy to use, "point and click" system. Such as OS could also provide an object-oriented environment or facsimile thereof (e.g., LabView-based systems) for customizing programming by sophisticated users, as well as providing for the development of additional software by the disk reader/player manufacturer or independent software developers.

The OS can also be chosen to allow design of disks and disk-based assays. Mechanical design, including simulation of rotational dynamics and stability and fluid flow simulation are advantageously encompassed in a disk design software package.

Communications aspects of the invention include hardware and software embodiments relating to data input and output from a user or to remote control and analysis sites. Hard-wired communications features include high-speed data-, video- or image-transmission and communication through local busses (e.g., a VGA bus for video signals) and conventional hard-wired interfaces (e.g., RS-232, IEEE-488, SCSI bus), Ethernet connections, Appletalk, and various local area networks (LANs). Telecommunications devices include cellular transceivers for short-range communications, radio-frequency and micro-wave transceivers for long-range communications, and internal or external modem for manual or automated telephone communications. Video in/out ports, analog out-lines for data transmission, input jacks for input of analog signals from other instruments, and optical and infra-red communications ports are also provided for communications with peripheral instruments.

Configurations of the Fluidics Micromanipulation Apparatus for Certain Applications The micromanipulation device includes various combinations of hardware and software as described above. FIG. 15 is an illustration of the general combination of communication, device, detection, and control instrumentation in a device. Certain applications may not have certain features, for example, portable units may not have graphical user interfaces. The micromanipulation device can be a "stand-alone" device, or a peripheral instrument to a larger assemblage of devices including, for example, computers, printers, and image-processing equipment, or a host for peripheral elements such as control pads, data entry/read-out units (such as Newton-type devices or equivalent), or an integrated system. The device in all embodiments comprises hardware to rotate the disk at both steady and variable rates and systems for monitoring rotation rate. The device can also include devices to initiate sample and disk diagnostics, perform "external" tests and detection as described herein, initiate sample and disk diagnostics, perform "external" tests and detection as described herein, initiate analyses on-disk through specific actuators such as valves, read disk-inherent information and information encoded in the disk or other data/information storage media information, and in some applications write information to the disk.

Additional elements in the device, including system control, data processors, array of assay processors, external detectors, external actuators, assay out and data out lines, communications, and software, are device-and/or application-specific.

For example, in a "point-of-use" portable or home-use application, sample loading is followed by initiation of the player's program. System control can be provided by front-panel controls and indicators which can access a variety of programs stored in the disk or the device. These "hard-wired" programs utilize controller circuitry to read or read/write operations from or to disk or memory, and/or perform tests using external devices. The device can be designed for performance of a single procedure, or can be pre-programmed to perform a set of procedures or multiple embodiments of the same procedure using a single disk. Device actuation is optimally obtained with the pressing of a single button. These processor(s) and data processors(s) of this type of device comprise circuitry and chipware designed to process analysis data (assay processor) and encoded data (data processor). Information from these processors can be available for output to the user on a front-panel or video display and can also be used internally to ensure correct operating conditions for the assay. This internal information processing can include the results of systems diagnostic tests to insure disk identity and test type compatibility; the presence of reagent and sample as determined through light absorption through a detector port scanning reagent and sample reservoirs; the presence of contamination detected before testing begins, and the results of self-diagnostics on external detectors and actuators. These results are used by the system controller to determine whether the requested test can be performed.

After loading and activation, analysis results can be stored internally in electronic memory or encoded upon the disk. The results of these analyses and procedures are then routed to the front-panel display (flat-panel LCD, etc.) using appropriate video drivers. Processed assay data can also be routed to one of many standard digital I/O systems including RS-232, RS-232C, IEEE-488, and other systems familiar from digital I/O and interface. Similarly, encoded disk data can be routed to the audio/visual display. Raw analog signals can also be switched to one or more external jacks for off-device storage or processing.

An embodiment of the least technically sophisticated device is a portable unit no larger than a portable audio CD player consisting of disk-drive, controllers and selectors for programmable or pre-programmed angular acceleration/deceleration profiles for a limited number of procedures. Such a device is advantageous for on-site toxic-chemical/contamination testing. Analyte to be tested is introduced to the disk, which is inserted into the player and the appropriate program chosen. Analysis results are stored on the disk, to be later read-out by a larger player/reader unit, and/or displayed immediately to the user. Results can also be stored as the inherent state of an indicator (positive/negative status of litmus paper in different cuvettes, for example), with no other data collection or analysis performed by the device. This data would be accessed by a larger player/reader or by other means outside the field-work environment. Information about the location, time, and other conditions of sample collection are entered through the user interface.

Another embodiment is a stand-alone device with active communications capabilities and greater functionality. An exemplary application for such a device is as a home blood-assay unit. This device is used by an individual placing a drop of blood on the disk, inserting the disk, and initiating the assay, preferably simply by pressing a single button. One or more analytical procedures are then performed. Assay data is transferred to software which performs the requisite analysis, either on-disk or within the device. The device can also be permanently or temporarily attached to the home-telephone line and automatically transmit either raw or reduced data to a computer at the central location is used to analyze the data transmitted, compare the data with accepted standards and/or previous data from the same patient, make a permanent record as part of a patient's device a confirmation of receipt of the data, perhaps the data analysis, and advice or suggested/recommended course of action (such as contacting the physician).

A desk-top peripheral/host application station constitutes a device as described above with the ability to accept instructions from and respond to a host computer over one of many possible data-protocols. The system is capable of acting as host or can transmit data to peripherals or other networked devices and workstations. Remote accessing of pre-programmed functions, function re-programming, and real-time control capabilities are also provided.

Yet another embodiment of this application is a centralized or bedside player/reader device with associated software located as a nurses' station in a hospital. As tests are performed on disks, the information is relayed to a physician by telephone, facsimile or pager via short-range transceiver. Patient identity can be entered at the time of sample collection by the use of bar codes and light pens attached to the device, providing the advantage of positive patient/sample identification.

The device can also be provided having the above-capabilities and functionality's and in addition having an interface with an integrated computer having high-resolution graphics, image-processing and other features. The computer provides control of the device for performing the functions described above for the peripheral system, while physical integration greatly increases data-transmission rates. Additionally, the integrated system is provided with extensive analysis software and background data-bases and information. Disk-storage cassettes of carousals are also an advantageous feature of such system. An integrated system of this type is useful in a large, analytical laboratory setting.

A self-contained system is useful for applications in isolated environments. Examples include devices used in remote or hostile setting, such as air, water and soil testing devices used in the Arctic for environmental purposes, or for use on the battlefield for toxic chemical detection.

The microsystem platforms provided by the invention are also useful for preparing samples for other analytical instruments, such as mass-spectrometers, gas chromatographs, high pressure liquid chromatographs, liquid chromatographs, capillary electrophoresis, inductively-coupled plasma spectroscopy, and X-ray absorption fine-structure. In some application, the final product is removed from the disk to be analyzed.

Samples can be pre-concentrated and purified on the device by incorporating aqueous two-phase separation systems. This can be done, for example, by mixing two phases which separate from each other based on thermodynamic differences like polyethylene glycol (PEG) and dextrans; biopolymers are usefully separated using this method. Alternatively, environmental tests such as colorimetric analysis can be enhanced by incorporating cloud-point separations to concentrate and enhance optical signals. In addition, small scale counter-current chromatography can be performed on the device (see, Foucault, 1991, *Anal. Chem.* 63: PAGE). Centripetal force on the disk can be used to force different density fluids to flow against each other, resulting in separation of components along a density gradient to develop the chromatogram.

Applications and Uses

The microsystem platforms and micromanipulating devices that make up the fluidics micromanipulation apparatus of the invention have a wide variety of microsynthetic and microanalytic applications, due to the flexibility of the design, wherein fluids are motivated on the platform by centripetal force that arises when the platform is rotated. What follows is a short, representative sample of the types of applications encompasses within the scope of the instant invention that is neither exhaustive or intended to be limiting of all of the embodiments of this invention.

The invention is advantageously used for microanalysis in research, especially biological research applications. Such microanalyses include immunoassay, in vitro amplification routines, including polymerase chain reaction, ligase chain reaction and magnetic chain reaction. Molecular and microbiological assays, including restriction enzyme digestion of DNA and DNA fragment size separation/fractionation can also be accomplished using the microsystem disks of the invention. Microsynthetic manipulations, such as DNA fragment ligation, replacement synthesis, radiolabeling and fluorescent or antigenic labeling can also be performed using the disks of the invention. Nucleic acid sequencing, using a variety of synthetic protocols using enzymatic replacement synthesis of DNA, can be performed, and resolution and analysis of the resulting nested set of single-stranded DNA fragments can be separated on the disk, identified and arranged into a sequence using resident software modified from such software currently available for macroscopic, automated DNA sequencing machines. Other applications include pH measurement, filtration and ultrafiltration, chromatography, including affinity chromatography and reverse-phase chromatography, electrophoresis, microbiological applications including microculture and identification of pathogens, flow cytometry, immunoassay and other heretofore conventional laboratory procedures performed at a macroscopic scale.

An illustrative example is immunoassay. While there exist a multiplicity of experimental methodologies for detecting antigen/antibody interactions that are in research and clinical use at the present time, the most robust immunoassay protocols involve "sandwich"-type assays. In such assays, an immobilized antibody is presented to a sample to be tested for the antigenic analyte specific for the immobilized antibody. A second antibody, specific for a different epitope of the same antigen is subsequently bound, making a "sandwich" of the antigen between the two bound antibodies. In such assays, the second antibody is linked to a detectable moiety, such as a radiolabel or fluorescent label, or a enzymatic or catalytic functionality. For example, horseradish peroxidase or alkaline phosphatase are used to produce a color change in a substrate, the intensity of which is related to the amount of the second antibody bound in the sandwich.

Figure 17Q:
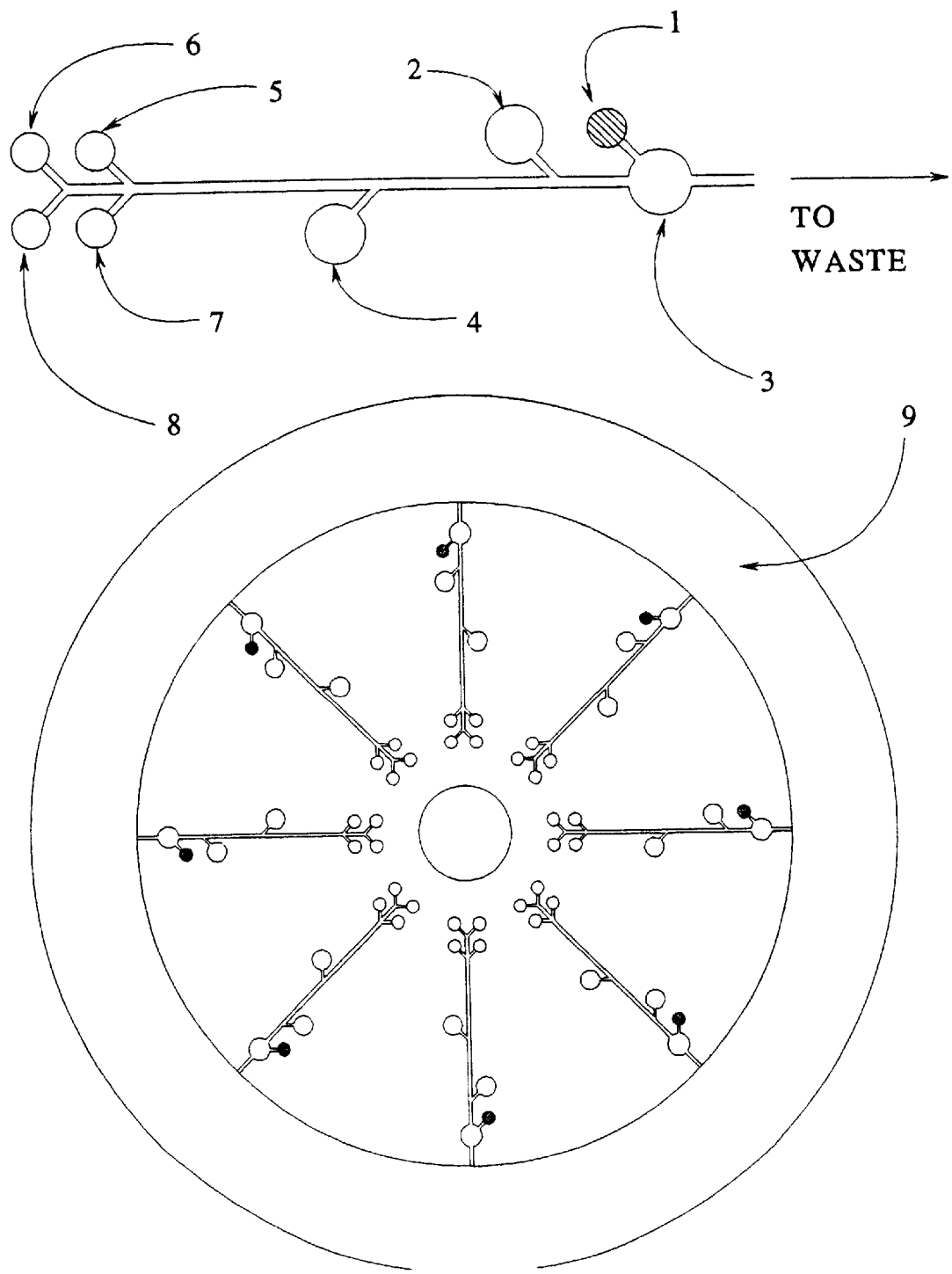
FIG. 17Q is a schematic diagram of a disk for immunoassay applications.

An example of a disk adapted for performing such an immunoassay is shown in FIG. 17Q. In this embodiment, the secondary antibody is linked to alkaline phosphate (AP). The presence and amount of AP activity is determined by monitoring the conversion of one of the following exemplary substrates by the enzyme calorimetrically: B-naphthyl phosphate converts to an insoluble azo dye in the presence of a diazonium salt; 5-bromo-4-chloro-3-indolyl phosphate is converted to 5,5'-dibromo-4-,4'-dichloro indigo in the presence of cupric sulfate; or 4-methylumbelliferyl phosphate is converted to 4-methylumbelliferone, which emits light at 450 nm.

In one exemplary embodiment, the reaction chamber comprises an antibody specific for an antigen, where the antibody is immobilized by adsorption of the antibody to the reaction chamber. Contiguous with the reaction chamber is advantageously placed a reagent reservoir containing a second antibody, this antibody being liked to an enzyme such as alkaline phosphate. Sample, which may contain an antigen of interest that is specifically recognized by the above antibodies, is loaded at an inlet port. The disk is spun to first introduce the sample into the reaction chamber containing immobilized antibody, followed by introduction of the second antibody into the reaction chamber after a time sufficient to saturate the immobilized antibody with antigen to the extent the antigen is present in the sample. Alternatively, the sample may be contacted with the second antibody, allowed to interact, then introduced into the reaction chamber. Incubation of the sample with antibody is performed without spinning for about 1 minute. After each incubation, washing buffer from a buffer reservoir is spun into the reaction chamber in order to remove unbound antibody. For alkaline phosphatase assays, solutions of 2 mg/mL o-dianisidine in water, 1 mg/mL B-naphthyl phosphate in 50 mM boric acid/50 mM KCl (pH 9.2) buffer and 100 mM magnesium chloride are delivered to the reaction chamber in the appropriate amounts. The extent of enzyme-linked, secondary antibody binding is evaluated by detection of a purple precipitate using a photodiode or CCD camera.

Figure 17R:
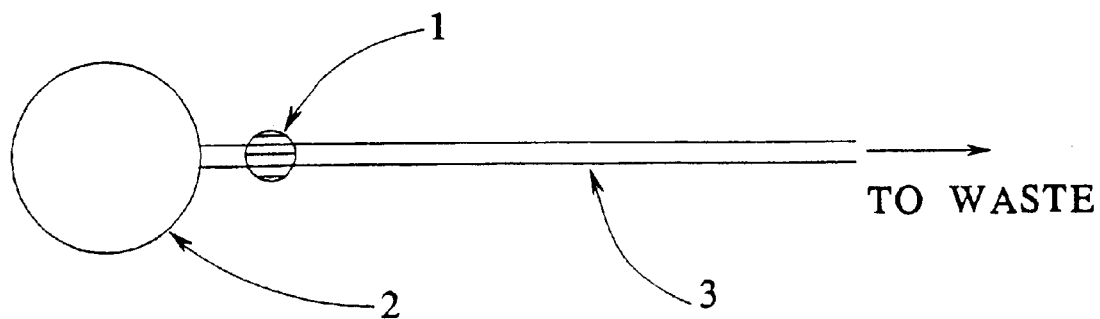
FIG. 17R is a schematic diagram of a thin-layer chromatography disk.
Figure 17R:
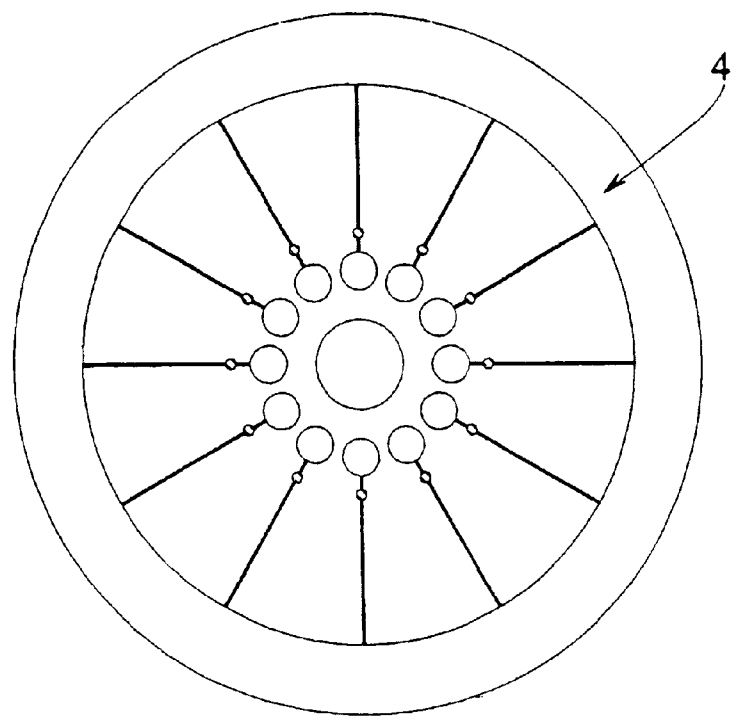

A disk configured for immunoassay applications is shown in FIG. 17R for illustration.

In an alternative embodiment of the immunological assays of the invention, the invention provides a means for identifying and quantitating the presence and number of particular cells or cell types in fluids, most preferably biological fluids such as blood, urine, amniotic fluid, semen and milk. In these embodiments of the invention, the Microsystems platform comprises a chamber or solid surface on the disk that is prepared to selectively bind the particular cell or cell type. After attachment of the cells to the surface, non-specific binding cells and other components are removed by fluid flow (washing) or centrifugal force (comprising the inertial flow of fluid in response to the centripetal acceleration of the disk). The cells of interest that remain attached to the microplatform surface or chamber are the detected and quantified using means including but not limited to microscopic, spectroscopic, fluorescent, chemiluminescent, or light-scattering means. The invention also provides such cells attached to a specific surface for toxicity monitoring, such as metabolic monitoring to determine the efficacy of bioactive drugs or other treatments. Ordered arrays of such surface are provided in certain embodiments to facilitate a complete determination of the purity and sterility of certain biological samples, and for cell cytometric and cytometry applications.

The surface or chamber of the disk for specific binding of the particular cells or cell types of interest is prepared to provide specific binding sites therefor. Typically, an antibody, preferably a monoclonal antibody, is attached to the surface or chamber, wherein the antibody is specific for a cell surface antigen expressed on the cell or cell type of interest. Alteratively, a ligand specific for a cell surface receptor expressed on the particular cell or cell type of interest is used to provide a specific attachment site. Arrays of specifically prepared surfaces or chambers are provided on certain embodiments of the disk. Surfaces and chamber are provided, for example, by contacting the surface with a solution of an appropriate antibody. In the practice of these preparation methods, contact of the surface with the antibody is followed by contacting the surface with a non-specific blocking protein, such as bovine serum albumin. Antibodies and blocking proteins can be contacted with the surface or chamber using a piezoelectrically driven point head (such as are used in ink-jet printing applications) can be advantageously used for this purpose. Alternatively, screen printing, or spraying the antibody solution on the chamber or surface using an airbrush can be employed. These methods are preferred in preparing surfaces and chambers in the 0.1–10 mm scale. In additional alternatives, microlithographic and microstamping techniques can be used to prepare the surface or chamber.

In the practice of the invention, a biological or other fluid sample containing the particular cell or cell type of interest is applied to the prepared surface or chamber and allowed in contact with the prepared surface or chamber for a time sufficient to allow specific binding of the cells or cell types to the surface. As contact with the surface may be inhibited by cell settling properties in the volume of the fluid, chambers and surfaces having minimized height transversely through the microsystem platform are preferred.

Non-specific cell binding is minimized or eliminated from the chamber or surface by washing the surface or chamber with a fluid amount sufficient to remove such non-specific binding. Washing is accomplished by simple bulk flow of fluid over the surface or chamber, or by centrifugation.

After washing, cells that remain attached to the surface or chamber are detected and counted. In a preferred embodiment, detection and counting is achieved using fluorescence microscopy. In the practice of the invention, specific dyes can be used to provide a fluorescence signal for any live cells remaining of the disk. The dye can be added directly to the surface or chamber, for example using a membrane-permanent dye, such as acetoxy-methyl ester dyes. Alternatively, specific antibodies can be linked to such dyes. Dyes can be added to the biological fluid comprising the cells prior to introduction onto the microsystem platform, or such dyes can be contacted with the cells in situ on the disk. The presence of the cells is detected using a fluorescence detector comprising a light source, a source filter, a dichroic filter or mirror, an emission filter, and a detector such as a photomultiplier tube.

In another example, thin-layer chromatography is accomplished on a microplatform disk comprising 100 pm square cross-section channels radiating outward from the center of the disk. Each channel is filled with separation substrate, which typically contains a binder material (0.1–10%) such as starch, gypsum, polyacrylic acid salts and the like, to provide mechanical strength and stability. (The use of such compounds in conventional TLC applications is discussed in Poole et al., 1994 *Anal Chem.* 66: 27A). Sorbents are also included in the materials comprising the separation channels, including for example cellulose, polyamide, polyethylene powders, aluminum oxide, diatomeceous earth, magnesium silicate, and silica gels. Such substrates can be modified for example with silanizing molecules, such as dimethyl-, ethyl-octa- and 3-aminoprophy-silanes. Preferentially the separation substrate contains sorbent-impregnated fiber glass or PFTE matrices.

Sample is loaded via a port located proximal to the center of rotation of the disk. Upon spinning the disk, a mobile phase is allowed to flow outward through the separation substrate, carrying sample components to the periphery of the disk at characteristic rates. The mobile phase can be chosen from a multiplicity of appropriate solvent systems including hexane, methanol and dichloromethane. Choice of a particular solvent depends on the nature of the disk material, the separation substrate and the components of the sample to be separated. Similarly, the choice of visualization reagents used to detect separated sample components are specific for the substances separated. For example, ninhydrin is used to detect amino acids; alimony chloride is used plus potassium permanganate for hydrocarbons; sulfuric acid plus anisaldehyde for carbohydrates; and bromine for olefins. Imagine of separation channels after separation is achieved using a CCD camera. A disk configured for him layer chromatography applications is shown in FIG. 17R for illustration.

Medical applications using the Microsystems of the invention are abundant and robust. Various embodiments of the invention provide for at-home, bedside, hospital and portable devices for rapid analysis of blood components, blood gases, drug concentrations, metabolities and infectious agents. In at-home monitoring embodiments, the invention provides a simple, easy-to-use consumer friendly device requiring a patient to add a blood droplet, urine sample or saliva sample to a specific application region on the disk, insert the disk in the device and start the device by pushing a button. In a hospital setting, both bedside and clinical laboratory embodiments are provided, wherein the bedside embodiment is advantageously linked electronically to a central processing unit located, for example, at a nurses station, and the clinical laboratory embodiment comprises a medical reference library for rapid, automated diagnostics of patient sample. The medical applications of the instant invention include blood testing (such as monitoring platelet counts in patients being treated with chemotherapeutic drugs); immunoassay for metabolites, drugs, and other biological and other chemical species; vaccine efficacy monitoring; myeloma or lupus erythematosus monitoring; determination of blood glucose and/or ketone body levels in patients with diabetes; automated cholesterol testing: automated blood drug concentration determination; toxicology; monitoring of electrolytes of other medically-relevant blood component at a patient's bedside; sepsis/endotoxin monitoring; allergy testing; and thrombus monitoring.

The invention also provides analytical instruments for environmental testing, industrial applications and regulation compliance. Portable, preferably hand-held embodiments, as well as more extensive embodiments, installed as part of an industrial quality control regime, are provided. Applications for these embodiments of the invention include analyte testing, particularly testing for industrial effluents and waste material, to be used for regulatory compliance; and quality control of industrial, most advantageously of human consumable items, particularly pharmaceuticals and specifically endotoxin determinations. Application for testing, mixing and evaluating perfumes and other complex mixtures are also within the scope of the invention.

The invention also provides chemical reaction and synthesis modeling, wherein a reaction scheme or industrial production regime can be tested and evaluated in miniaturized simulations. The invention provides for cost-effective prototyping of potential research, medical and industrial chemical reaction schemes, which can be scaled to macroscopic levels after analysis and optimization using the microsystems platforms of this invention.

A variety of other applications are provided, including microsynthetic methods and forensic applications.

The following Examples are intended to further illustrate certain preferred embodiments of the invention and are not limiting in nature.

EXAMPLE 1

Fabrication of Microplatform Disks for Chemical Analysis, Synthesis, and Applications Microplatform disks of the invention are fabricated from thermoplastics such as Teflon, polyethylene, polypropylene, methylmethacrylates and polycarbonates, among others, due to their ease of molding, stamping and milling. Alternatively, the disks can be made of silica, glass, quartz or inert metal. A fluid handling system is built by sequential application of one or more of these materials laid down in stepwise fashion onto the thermoplastic substrate. FIGS. 17A through 17E are a schematic representation of a disk adapted for performing DNA sequencing. Disks of the invention are fabricated with an injection molded, optically-clear base layer having optical pits in the manner of a conventional compact disk (CD). The disk is a round, polycarbonate disk 120 mm in diameter and 100 pm thick. The optical pits provide means for encoding instrument control programming, user interface information, graphics and sound specific to the application and driver configuration. The driver configuration depends on whether the micromanipulation device is a hand-held, benchtop or floor model, and also on the details of external communication and other specifics of the hardware configuration. This layer is then overlaid with a reflective surface, with appropriate windows for external detectors, specifically optical detectors, being left clear on the disk. Other layers of polycarbonate of varying thickness are laid down on the disk in the form of channels, reservoirs, reaction chambers and other structures, including provisions on the disk for valves and other control elements. These layers can be pre-fabricated and cut with the appropriate geometries for a given application and assembled on the disk. Layers comprising materials other than polycarbonate can also be incorporated into the disk. The composition of the layers on the disk depend in large part on the specific application and the requirements of chemical compatibility with the reagents to be used with the disk. Electrical layers can be incorporated in disks requiring electric circuits, such as electrophoresis applications and electrically-controlled valves. Control devices, such as valves, integrated circuits, laser diodes, photodiodes and resistive networks that can form selective heating areas or flexible logic structures can be incorporated into appropriately wired recesses, either by direct fabrication of modular installation onto the disk. Reagents that can be stored dry can be introduced into appropriate open chambers by spraying into reservoirs using means similar to inkjet printing heads, and then dried on the disk. A top layer comprising access ports and air vents, ports or shafts is then applied. Liquid reagents are then injected into the appropriate reservoirs, followed by application of a protective cover layer comprising a thin plastic film.

A variety of other disk configurations are disclosed in FIGS. 17F through 17P, adapted for particular applications as described in the Figure legends.

EXAMPLE 2

Blood Composition Determination

Figure 18:
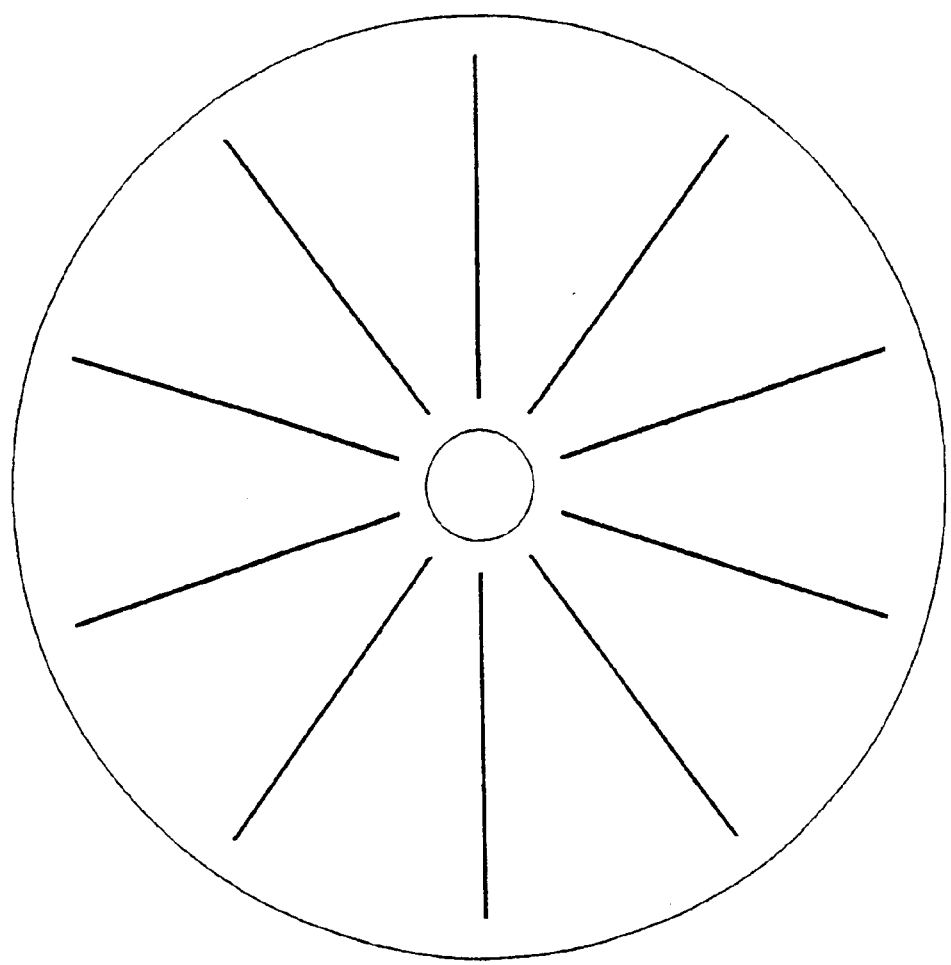
FIG. 18 is a schematic diagram of a disk configured for hematocrit determination.

Blood composition can be determined via hematocrit analysis using an analytic microplatform disk prepared as described in Example 1 held within a device comprising a microchannel layer with a number of microchannels as shown in FIG. 18. The microchannel layer is 100 pm thick and treated with heparin to prevent coagulation during the assay. The blood sample to be analyzed is drawn by capillary action into a channel arranged perpendicular to the direction of rotation, as shown in FIG. 18; a number of such channels may be arranged radially on the disk. When all samples to be tested have been drawn into the channels, the disk is spun at a speed of 8000 to 10,000 rpm to effect sedimentation of erythrocytes within the channel. Once centrifugation has been performed for an appropriate time (3 to 5 minutes), the hematocrit of each sample is determined simultaneously by stroboscopic interrogation of each of the channels using a conventional CD laser system in the device described above. When the laser passes the boundary of erythrocytes, the change in light scattering pattern detected by the photodiode detector is converted into a hematocrit value based on a standardized set of light scatter/hematocrit information stored in the internal processor and memory of the device. Alternatively, the raw information is relayed via a infrared port or hard-wired interface to a microprocessor for analysis. Such a central microprocessor is on site or in the alternative at a centralized location, such as a nursing station in a hospital or in a medical center connected to the hematocrit determining device by telephone or other dedicated connection. Hematocrit can be determined by untrained individuals (including patients) by the simple application of a blood droplet produced by lancet onto the disk, followed by the simple application of the device and automated hematocrit analysis and data processing on site or transmission to a central location of trained medical personnel. This embodiment of the invention provides for chronic monitoring of patients having hematopoietic proliferative disease (such as leukemia, lymphoma, myeloma, and anemias).

In addition, blood gas can be determined using the above device in combination with a disk having integrated electrodes embedded within the hematocrit channel, or having a separate channel devoted to blood gas determination on the hematocrit disk. Blood oxygenation ($PO_2$) is determined by a Clark-type electrode consisting of a thin Cr—Au cathode and an Ag—AgCl wire anode. The amount of carbon dioxide in the blood is determined by a Severing-type electrode using an ISFET (a type of field effect transistor) as a pH monitor. Blood pH is determined with the use of a $Si_3N_4$ gate ISFET with a reference electrode consisting of a liquid junction and an Ag—AgCl wire electrode. Further examples of such analytical methods for determining blood gases, electrolyte concentration and other information advantageously performed using the hematocrit disk or alternate variations of this disk are described as modifications of the macroscopic-scale methods of Shoji & Esashi (1992, *Sensors and Actuators B* 8: 205).

Figure 19:
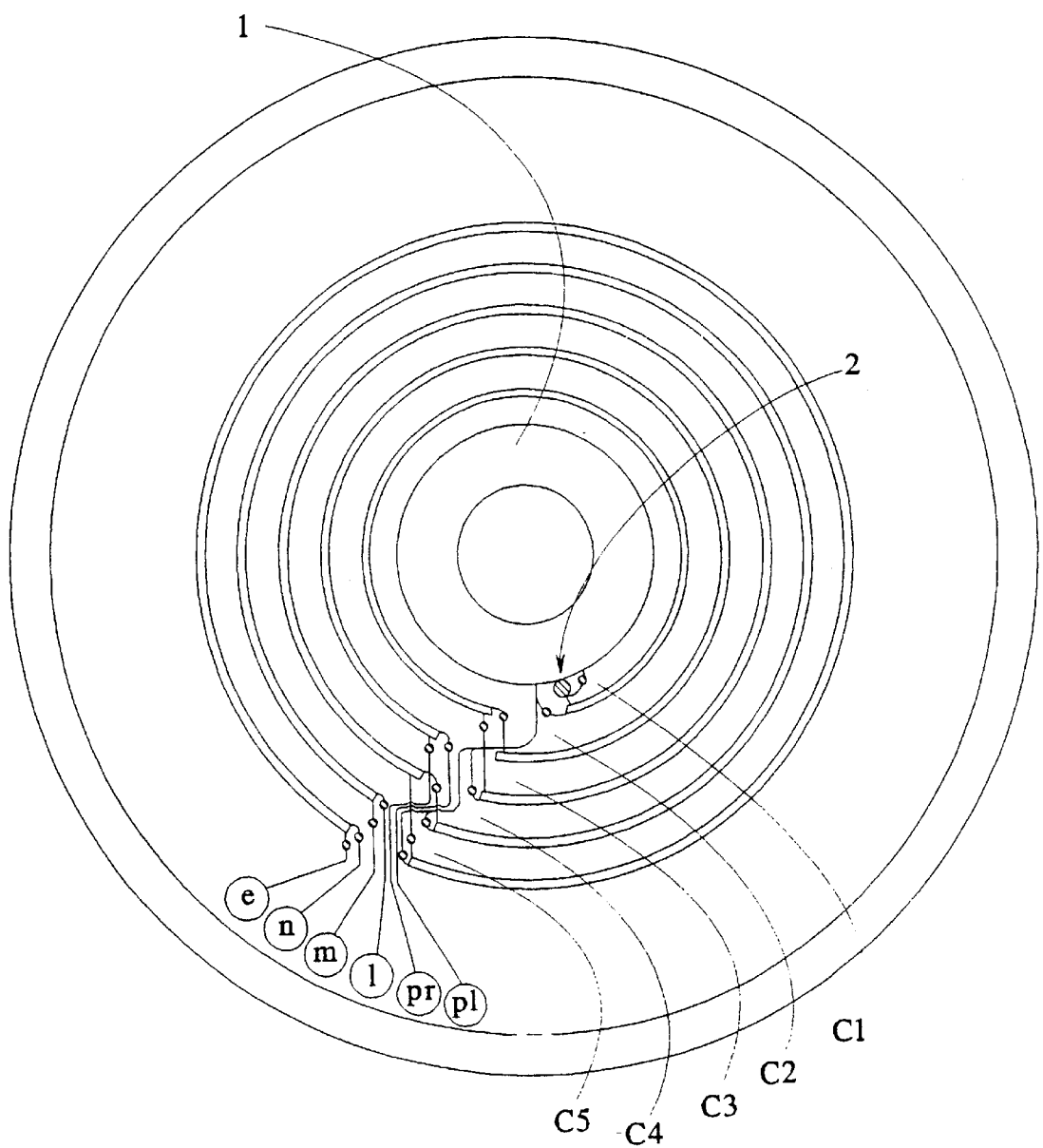
FIG. 19 is a schematic diagram of a disk configured for SPLITT fractionation of blood components.

Blood analysis are also performed using split-flow thin cell (SPLITT) fractionation as described by Bor Fuh et al. (1995, *Biotechnol. Prog.* 11: 14–20). A schematic representation of a disk configured for SPLITT analysis is shown in FIG. 19. This process can produce enriched fractions of proteins and lipoproteins, platelets, erythrocytes, lymphocytes, monocytes, and neutrophils. A non-contiguous circular channel is etched into the disk incorporating a thin wall at either end (FIG. 19), the inlet stream splitter. Sample and carrier streams are introduced at opposite sides of one end, and the chamber is spun in that direction. Within the spinning chamber two distinct splitting planes are set up based on hydrodynamic forces, the inlet splitting stream (ISP) and the outlet splitting stream (OSP). The ISP is adjustable by regulating the ratio of the sample to the carrier streams. Depending on the method of sample input two distinct separation modes are possible, the equilibrium and transport modes.

In the equilibrium mode separation is based on the equilibrium of the components in relation to the applied centrifugal field. Separation is optimized by adjusting the outlet flow ratio. The enriched fraction can then be collected from either side of the outlet stream splitter. In the transport mode the components are introduced as a thin lamina above the ISP. Based on the difference in sedimentation coefficients components with a higher transport rate are selectively directed to the opposite sides of the outlet valves at the orifices. Variable flow valves are described elsewhere in this document. In another embodiment each SPLITT chamber may be dedicated to the separation type required of it, ISP or OSP, and the flow regulated by fixed flow-restriction orifices.

In order to fully fractionate blood into the above-identified fractions, five separations, each yielding two fractions, are performed. One embodiment of the microsystems disk of the invention used for this type of fractionation is shown in FIG. 19. Five concentric SPLITT cells are illustrated in this FIG. 1 labeled C1, (close to the center of rotation) through C5 (toward the periphery). A blood sample is introduced into C1 and subjected to a transport mode separation by rotating the disk at the appropriate speed. Platelets and proteins (fraction 1) are fractionated toward the center of rotation and blood cells (fraction 2) move toward the periphery. Fraction 1 is routed to the inlet of C2 while fraction 2 is routed to C3 by the opening and closing of appropriately-positioned valves on the disk. The fractions are then subjected to transport and equilibrium mode separations respectively. Using these techniques, Fraction 1 results in platelets toward the center of rotation and proteins toward the periphery. Fraction 1 results in platelets toward the center of rotation and proteins toward the periphery. Fraction 2 yields fractions 3 and 4, consisting of lymphocytes and monocytes toward the center of rotation and erythrocytes and neutrophils toward the center of rotation and monocytes toward the periphery. Fraction 4 yields neutrophils toward the center of rotation and erythrocytes toward the periphery. Thus, fractionation of blood into five isolated components is achieved.

The activity of enzymes in the protein fraction can be determining using immobilized enzymes (Heineman, 1993, *App. Biochem. Biotech.* 41: 87–97). For example, blood-specific enzymes (such as glucose oxidase, alkaline phosphatase, and lactate oxidase) can be immobilized in poly (vinyl alcohol (PVAL). Lactate oxidase is immobilized on platinized graphite electrodes by sandwiching a thin layer of enzyme between two layers of PVAL. The sensor responds to lactate by the electrochemical oxidation of hydrogen peroxide generated by the enzyme-catalyzed oxidation of lactate that diffuses into the network. The current produced is proportional to the concentration of peroxide, which in turn is proportional to the concentration of lactate. This sensor has been shown to be sensitive to lactate concentrations ranging form 1.7–26 uM.

Upon separation, each fraction is interrogated by detection systems to determine the relative components of the fractions. Alternatively, each fraction can be removed from the disk through an outlet port for further study off-device. For example, each fraction can be subjected to simple counting by passing the cells in a thin stream past two electrodes comprising a resistance monitor. As a cell passes through the electrodes a corresponding rise in resistance is monitored and counted. These data are then integrated relative to a standard set of particles distributed according to size to determine the relative number of each cell type in the original sample.

The fractions can be subjected to fluorescent antibody staining specific to each cell type. The cells are held in place by micromachined filters integral to the channels (U.S. Pat. No. 5,304,487), stained and washed on the disk. The resulting labeled cells can then be quantified as a function of the degree of fluorescent staining associated with the cells.

EXAMPLE 3

DNA Sizing and Mutation Detection

Figure 20:
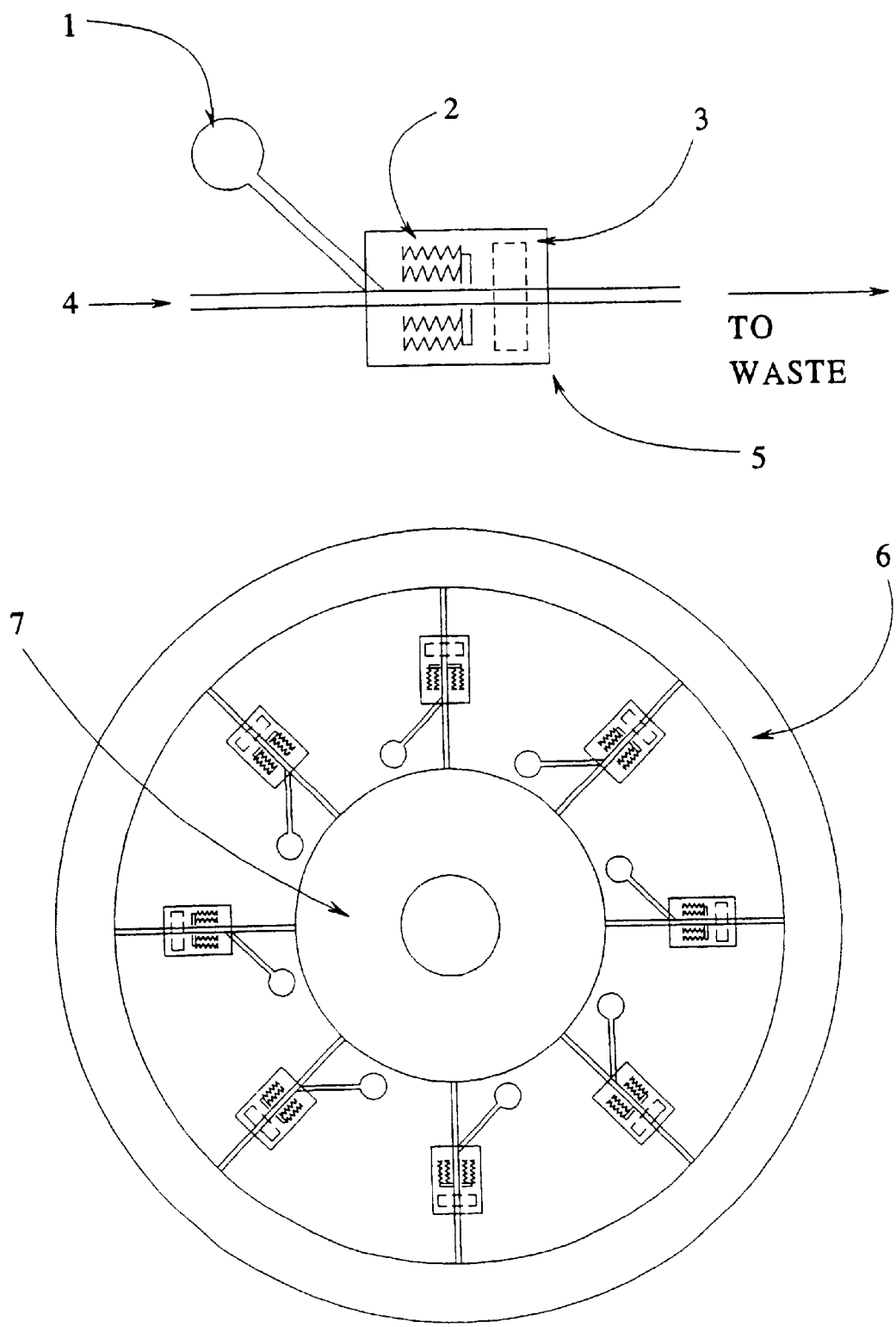
FIG. 20 is a schematic diagram of a disk configured as a DNA meltometer.

DNA sizing and detection of specific mutations in DNA at a particular site are carried out using double stranded melting analysis with a disk prepared according to Example 1 and illustrated in FIG. 20. A DNA meltometer (as described in co-owned and co-pending U.S. Ser. No. 08/218,030, filed Mar. 24, 1994 and incorporated herein by reference in its entirety) is advantageously incorporated into the structure of the disk Example 1. The DNA meltometer technique takes advantage of the fact that the denaturing point of a DNA duplex is dependent upon the length, the base composition, and the degree of comlplimentarity of the two strands in the duplex. A denaturing point may be determined in relation to some physical state of the molecule (such as temperature or the concentration of a denaturing chemical such as urea or formamide, and a set of standard conditions employed, the information derived from which can be stored in the microprocessor and/or memory of the device. In order to size any particular DNA duplex, one strand is immobilized on the disk by attaching it to a streptavidin coated bead. The bead is retained by a filter machined in to the channel (see U.S. Pat. No. 5,304,487). Alternatively, the bead can be a paramagnetic bead retained in the channel by application of a magnetic filed using a permanent magnet incorporated into the disk of positioned in proximity to the channel. An electromagnet can be used. The electromagnet can be incorporated directly into the disk and actuated by application of 0.8 volt DC at 500 mA. The other strand is labeled, typically using a fluorescent dye or a radioactive isotope. Alternatively, the distinct optical properties of the DNA molecule itself (i.e., hyperchromicity) are detected using unlabeled DNA molecules by monitoring absorbance at 260 nm. Although this aspect of the method requires a more sophisticated device to generate and detect ultraviolet light, user preparation of the DNA is minimized and the cost of DNA preparation per sample greatly reduced. In the practice of the method of the invention, the immobilized, labeled duplex is placed on the disk and subjected to a flow stream of a buffered solution contained on the disk. During the development of the flow stream, the DNA is further subjected to a controlled denaturing gradient produced in the flow stream by the gradual addition of denaturant to the DNA. With an effective radius of 3.5" and a rotational speed of 600 rpm, a flow rate of 10 uL/min can be generated in a channel 100 um in diameter. Four buffer reservoirs each containing 300 uL can be incorporated into each quadrant of the disk (800 um deep extending from a position at a radius of 25 mm to 50 mm). At 10 uL/min, this will allow a melting ramp of 30 min. Each duplex dissociates at a characteristic concentration of denaturant in the gradient, and can be identified in comparison with standards the denaturant profile information of which is stored in the microprocessor and/or memory of the device. Denaturation is detected by interrogation downstream of the melting chamber, using the appropriate detecting means (photooptical means for ultraviolet absorption or fluorescence detection, or radioisotope detectors (Geiger-Mueller counters) for DNA stands labeled with radioisotopes).

Exemplary of the uses the disks and devices of this aspect of the invention is the detection, identification and size determination of DNA fragments produced by polymerase chain reaction or magnetic chain reaction (the latter disclosed in U.S. Ser. Nos. 08/375,226, filed Jan. 19, 1995, which is a file wrapper continuation of U.S. Ser. No. 08/074,345, filed Jun. 9, 1993 and Ser. No. 08/353,573, filed Dec. 8, 1994, each incorporated by reference in its entirety). Amplification is carried out using one primer labeled with a detectable label such as a fluorescent dye or radioisotope, and the other primer is covalently attached to a molecule that permits immobilization of the primer (e.g., biotin). After amplification (either off-disk or on the disk as described in more detail in Example 4 below), the labeled, biotinylated duplex DNA product fragment is attached to a solid support coated with streptavidin, for example, by movement of the amplification reaction mixture into a channel or compartment on the disk wherein the walls are coated with streptavidin, or by movement of the amplification mixture into a compartment on the disk containing a binding matrix such as Dynal—280 Dynabeads (polystyrene coated paramagnetic particles of 2.8 um in diameter). Standardized size markers are included in the post-amplification compartment in order to provide a reference set of DNA fragments for comparison with the amplification product fragments. In this analysis, a number of different duplex DNA molecules from either a multiplex amplification reaction or a number of separate amplification reactions may be sized simultaneously, each fragment or set of fragments being distinguished from others by use of reaction- or fragment-specific detectable labels, or differences in some other physical property of the fragments. For amplifications performed off-disk, beads attached to the fragment are loaded into a channel on the disk capable of retaining the beads (such as size exclusion, "optical tweezers" or by magnetic attraction). In the latter embodiment, the magnetic retention means (permanent magnets or electromagnets) are either integral to the disk, held on second disk spinning synchronously with the first, or placed on the device so as to immobilize the DNA fragments in the appropriate compartment.

DNA size analysis is also performed essentially as described above, whereby the retained particles are subjected to a thermal denaturing gradient. For a thermal gradient used to denature the bound DNA fragments, a Peltier heat pump, direct laser heating or a resistive element is used to increase the temperature of the binding compartment through the denaturation range by the gradual addition of thermal energy. As above, a flow rate of 10 $\mu$L/min can be generated in a channel 100 $\mu$m in diameter, allowing a melting ramp of 30 min. The compartment is also subjected to a flow stream as described above to elute the denatured, labeled stands from the binding/melting chamber. Downstream from the binding/melting chamber are appropriate means for detecting DNA fragment denaturation, such as laser excitation at the resonant frequency of the dye label and photodiode detection. The strength and corresponding temperature of the raw absorbance or other signal is integrated by the microprocessor and the size of each DNA fragment determined by comparison to internal DNA size marker controls and DNA melting profiles and characteristics stored in the microprocessor and/or memory of the device.

DNA mutations are also detected by meltometer analysis. DNA fragments to be tested (including amplification-derived fragments and restrictions enzyme digestion or cloned fragments) are prepared and hybridized with a bound standard (typically wildtype) copy of the gene or gene fragment of interest. Hybridization is performed either on-device or using conventional DNA hybridization methods (as described in Hames & Higgins, *Nucleic Acid Hybridization: A Practical Approach*, Rickwood & Hames, eds., IRL Press: Oxford, 1985). Elution of the hybridized fragments is dependent on the degree of complimentarily between the two species of DNA strands (i.e., wildtype and mutant). Hybridization analysis is performed using wildtype DNA that is prepared wherein one strand is covalently attached to a molecule that permits its immobilization. The non-covalently attached strand is then eluted by washing at a temperature much greater than the $T_m$ of the duplex (typically, the DNA is heated to >90° C., or to lower temperatures in the presence of denaturants such as formamide). Elution is monitored to determine the concentration of bound single-stranded product available for further hybridization; typically, the amount of DNA eluted is monitored, for example by ultraviolet light absorbance, and the bound DNA considered to be completely single stranded when no more DNA can be eluted. The wildtype DNA is prepared whereby only one of the strand making up the duplex is covalently attached to the immobilizing molecule, in order to require detectable labeling of only one (the complementary one) strand of the mutant DNA to be tested. Alternatively, either strand may be covalently attached, requiring both mutant strands to be detectably labeled. An advantage of double-labeling the mutant fragment even when only one wildtype strand is covalently attached to the immobilizing molecule, is that denaturation and elution of the non-complementary strand can be monitored during hybridization, and non-specific binding/hybridization of the mutant to wildtype DNA strands can be detected.

After hybridization is accomplished, the degree of complementarity of the strands is determined by a modification of the thermal or chemical denaturing protocols described above. Analysis of the resulting pattern of duplex melting is performed by comparison to a pattern of mismatched DNA duplex melting prepared either simultaneously or prior to experimental analysis and stored in the device microprocessor and/or memory using standard or expected single base or multiple mismatches. Such comparison form the basis for a determination of the rapid screening of individuals for a variety of characterized disease-associated genetic polymorphisms.

DNA mutations are also detected by meltometer analysis. In this embodiment, test DNA is immobilized on the disk and subjected to hybridization/denaturation analysis with a battery of precharacterized test probes. Using this method, DNA fragments are preferably prepared using in vitro amplification techniques, so that one strand is immobilizable due to covalent attachment of the binding molecule to one of the primers. Using this method, the DNA fragment to be tested is sequentially hybridized with and eluted by denaturation from a series of well-characterized DNA probes being detectably labeled. Alternatively (depending on the nature of the DNA mismatch expected for each probe), hybridization and denaturation are multiplexed, using probes detectably labeled with different detectable labels so that each probe can be identified. This method is useful for genetic screening as described above.

EXAMPLE 4

DNA Amplification and Analysis

Figure 21:
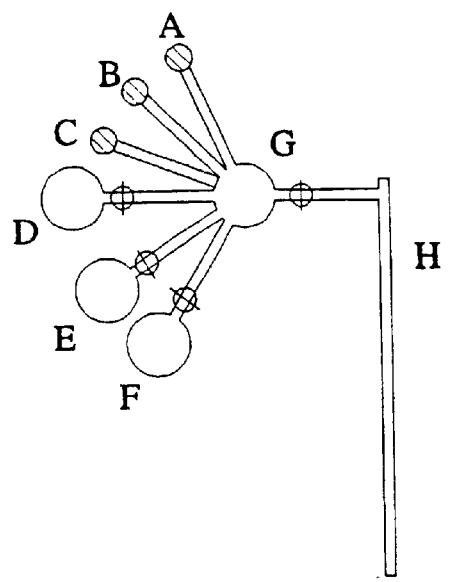
FIG. 21 is a schematic diagram of a disk configured for DNA amplification.

Fragments of DNA are amplified in vitro by polymerase chain reaction (PCR) or magnetic chain reaction and analyzed by capillary electrophoresis. Reagent mixing, primer annealing, extension and denaturation in an amplification cycle resulting amplification of a 500 bp target fragment and its subsequent analysis are carried out using a device and disk as described in Example 1 above. A schematic diagram of the structure of the disk is shown in FIG. 21.

The disk comprises at least three sample input ports A, B and C. Port A permits injection of 30 attomoles (about 100 pg) linear bacteriophage lambda DNA. Port B and C allow input of 5 μL of a 20 μM solution of primer 1 and 2 respectively, having the sequence:

```
Primer 1: 5'-GATGAGTTCGTGTCCGTACAACTGG-3' (SEQ ID No.: 1) and

Primer 2: 5'-GGTTATCGAAATCAGCCACAGCGCC-3' (SEQ ID No.: 2).
```

The disk also comprises three reagent reservoirs D, E and F in the Figure and containing 54 μL of distilled water; 10 μL of a solution of 100 mM Tris-HCl (pH 8.3), 500 mM KCl, 15 mM MgCl$_2$, 0.1% gelatin and 1.25 μM of each dNTP; and 1 μL of Taq DNA polymerase at a concentration of 5 Units/μL, respectively.

In addition, the disk comprises a reaction chamber G that is configured to facilitate mixing of these reagents using a flexural-plate-wave component (as described in U.S. Pat. No. 5,006,749). Also included in the configuration of reaction chamber G are cooling and heating means via a Peltier component. These components can be integral to the disk or can be positioned in the device so as to provide heating and cooling specific for the reaction chamber. Disks are also provided that comprise a multiplicity of sets of the reaction components A through G.

Amplification is initiated by introducing sample DNA and primer into each set of ports A, B and C. When all samples and primers have been introduced into the ports, the disk is spun at a speed of 1 to 30,000 rpm to effect mixing of the reagents into reaction chambers G. Simultaneously, valves controlling reservoirs D, E and F are opened and the contents of these reservoirs are also forced into reaction chamber G. Mixing of sample DNAs, primers and reagents is facilitated by activation of the flexural-plate-wave component. DNA amplification takes place in the reaction chamber using the following thermocycling program. The reaction mixture is initially heated to 95° C. for 3 minutes. The amplification cycle thereafter comprises the steps of: step 1, incubation at 95° C. for 1 minute; step 2, cooling the chamber to 37° C. for 1 minute; and step 3, heating the chamber to 72° C. for 3 minutes. This amplification cycle is repeated for a total of 20 cycles, and the reaction completed by incubation at 72° C. for 5 minutes.

Amplified DNA fragments are analyzed by transfer to capillary electrophoresis unit H by spinning the disk at a speed of 1 to 30,000 rpm and opening a valve on reaction chamber G leading to capillary electrophoresis unit H, thereby effecting transfer of an amount of the reaction mixture to the electrophoresis unit. The amount of the reaction mixture, typically 10 μL, is determined by a combination of the length of time the valve on reaction chamber G is open and the speed at which the disk is rotated. Capillary electrophoresis is accomplished as described below in Example 11, and fractionated DNA species detected using optical or other means as described above in Example 2.

This method provides a unified amplification and analysis device advantageously used for performing PCR and other amplification reactions in a sample under conditions of limited sample.

EXAMPLE 5

DNA Restriction and Digestion and Analysis

Figure 22:
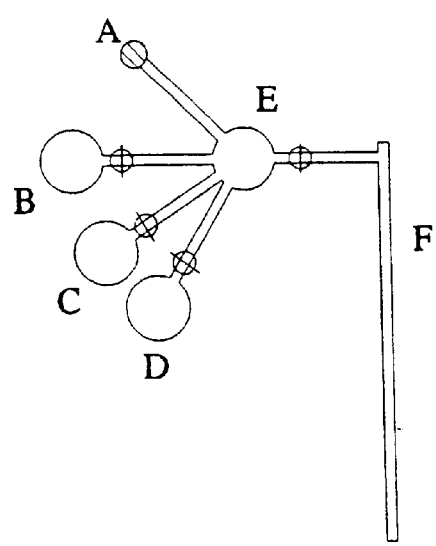
FIG. 22 is a schematic diagram of a disk configured for automated restriction enzyme digestion of DNA.

Restriction enzyme digestion and restriction fragment analysis is performed using a disk and device as described above in Example 1. A double-stranded DNA fragment is digested with a restriction endonuclease and subsequently analyzed by capillary electrophoresis. Reagent mixing, DNA digestion and restriction fragment analysis are carried out on the disk. A schematic diagram of the structure of the disk is shown in FIG. 22.

The disk comprises a sample input port A; three reagent reservoirs B, C and D; a reaction chamber E configured for mixing the reagents as described above in Example 5, and a capillary electrophoresis unit F. The reagent reservoirs contain: 1–2 μL of a restriction enzyme, e.g. HindIII, at a concentration of 20 Units/μL in reservoir B; 4 μL of a solution of 100 mM Tris-HCl (pH 7.9), 100 mM MgCl$_2$ and 10 mM dithiothreitol in reservoir C; and 30 μL of distilled water in reservoir D. Disks are also provided that comprise a multiplicity of sets of the reaction components A through E.

Restriction enzyme digestion of the DNA is initiated by placing 4–5 μL of a solution (typically, 10 mM Tris-HCl, 1 mm EDTA, pH 8) containing 4 μg bacteriophage lambda DNA in sample input port A. The DNA sample and the reagents in reservoirs B, C and D are transferred to reaction chamber E by spinning the disk at a rotational speed of 1 to 30,000 rpm and opening valves controlling reservoirs B, C and D. The reaction is incubated at 37° C. for 1 h in reaction chamber E after mixing, the reaction chamber being heated by provision of a Peltier heating element either on the disk or positioned in the device so at to specifically heat the reaction chamber. After digestion, an amount of the digested DNA is transferred to electrophoresis unit F by spinning the disk at a speed of 1 to 30,000 rpm and opening a valve on reaction chamber E leading to capillary electrophoresis unit F, thereby effecting transfer of an amount of the reaction mixture to the electrophoresis unit. The amount of the reaction mixture, typically 10 μL, is determined by a combination of the length of time the valve on reaction chamber E is open and the speed at which the disk is rotated. Capillary electrophoresis is accomplished as described below in Example 11, and fractionated DNA species detected using optical or other means as described above in Example 2.

EXAMPLE 6

DNA Synthesis

Oligonucleotide DNA synthesis is performed using a disk and device as described above in Example 1. Synthesis is achieved by the stepwise transport of controlled pore glass (CPG) through a series of reaction chambers containing reagents necessary for phosphoramidite DNA synthesis. Reagents and CPG are delivered sequentially to reaction chambers by single-use valves connecting the reaction chambers to each other and to reagent reservoirs. Each disk has a number of synthesis reaction chambers to produce oligonucleotides having a length similar to the length of oligonucleotides produced by commercially-available DNA synthesis instruments (i.e., 100–150 bases). A schematic diagram of the structure of the disk is shown in FIG. 23A.

A CPG bearing a first base of a sequence (thereby defining the 3' extent of the oligonucleotide) is loaded either by the user or by automated means into a sample input port A. The CPG is then transferred into a reaction chamber containing trichloroacetic acid (TCA) in acetonitrile ($CH_3CN$) by spinning the disk at a rotational speed of 1 to 30,000 rpm. Detritylation of the nucleotide is performed at room temperature for a defined time interval, typically 1 minute. The reagent is then decanted from the first reaction chamber by opening a valve with a bore too small to allow passage of the CPG but sufficient to drain the TCA-containing mixture into a decantation chamber. As the deprotection of the base by detritylation is known to produce a colored product (orange), the intensity of which is a measure of the extent of the reaction, optical means for determining the absorbance of this effluent are advantageously provided to be recorded on the device microprocessor/memory. After decanting the reaction mixture, the CPG are spun into a rinse chamber containing $CH_3CN$, the chamber optionally comprising a mixing means as described above. After rinsing, the $CH_3CN$ is decanted into a effluent reservoir controlled by a size-selective valve as above, and the CPG spun into a second reaction chamber. Mixed with the CPG in the second reaction chamber is a solution containing one of four phosphoramidite bases (G, A, T, or C) corresponding to the next position in the oligonucleotide chain. The reaction mixture in the second reaction chamber is mixed and allowed to react for a defined time interval, typically three minutes. The reaction mixture is then decanted as above and the CPG spun into a rinse chamber containing $CH_3CN$ and a mixing means. After rinsing, the $CH_3CN$ is decanted to an effluent reservoir and the CPG is spun into a third reaction chamber containing an oxidizing mixture of iodine, water, pyridine and tetrahydrofuran, where the reaction mixture is incubated for a defined time interval, typically 1 minute. The reaction mixture is decanted to an effluent reservoir and the CPG spun into a rinse chamber containing $CH_3CN$. After rinsing, the $CH_3CN$ is decanted to an effluent reservoir and the CPG spun into a fourth reaction chamber along with a two-component "capping" reagent. The capping reaction is performed for a defined time interval, typically 1 minute. After the reaction is complete, the reaction mixture is decanted to an effluent reservoir as above and the CPG spun into a rinse chamber containing $CH_3CN$. The $CH_3CN$ is then decanted to an effluent reservoir and the CPG is spun into a fifth chamber containing TCA, comprising the beginning of another cycle. The cycle is repeated by transit of the CPG through interconnected series of the four reaction chamber until the preprogrammed sequence is completely synthesized. The CPG is then spun into a reaction chamber containing concentrated ammonium hydroxide and heated at 60° C. for a defined time interval, typically 6 hours, during which time the DNA molecule is deprotected and cleaved from the CPG support. The finished oligonucleotide is removed by the user or by automated means.

The disk provides a series of reaction chambers linked to each other and comprising four reaction and rinsing chambers per nucleotide to be added to the oligonucleotide chain. The disks can be loaded to produce a particular oligonucleotide, or each reaction chamber 2 can be in contact with reagent reservoirs containing each of the four nucleotide bases and linked to the reaction chamber by an individually-controllable valve. In this embodiment, activation of the appropriate valve at each step in the cycle is controlled by a signal from the device. Disks comprising a multiplicity of these synthetic arrays. Permitting simultaneous synthesis of a plurality of oligonucleotides, are also provided. A schematic diagram of a disk configured for multiple oligonucleotide synthesis is shown in FIG. 23B.

Figure 23A:
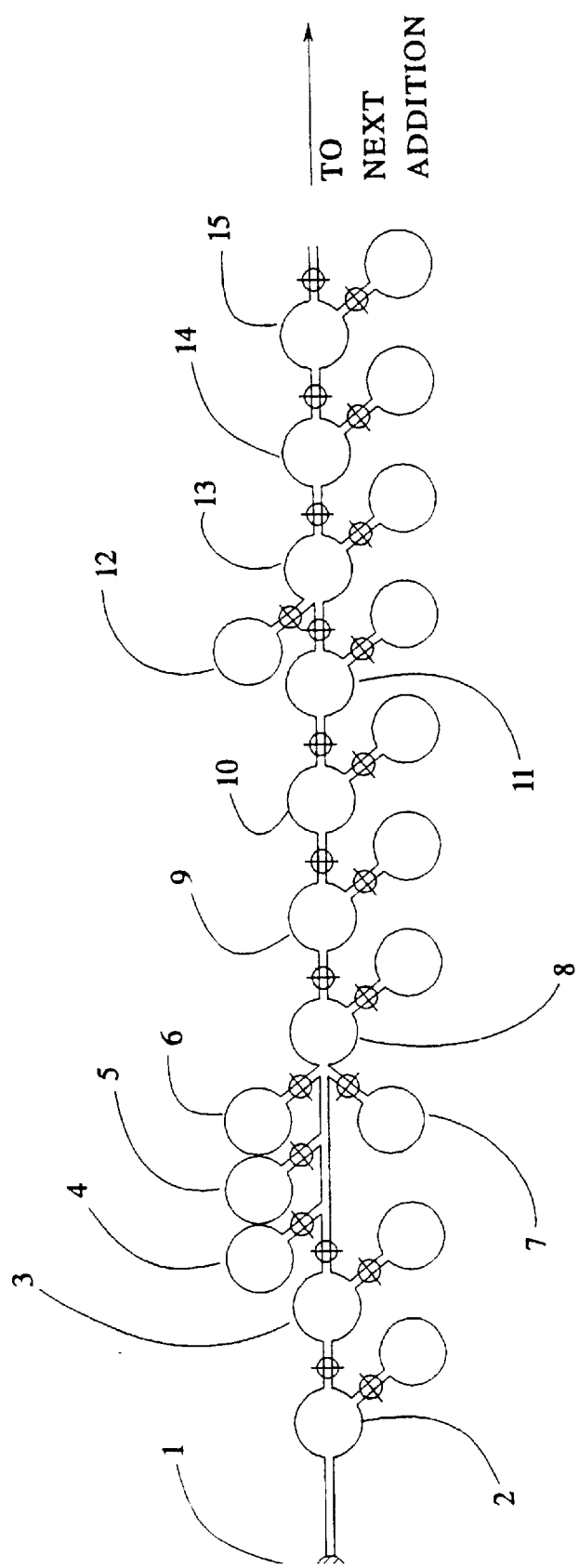
FIG. 23A is a schematic diagram of a portion of a disk microsystem configured for DNA synthesis.
Figure 23B:
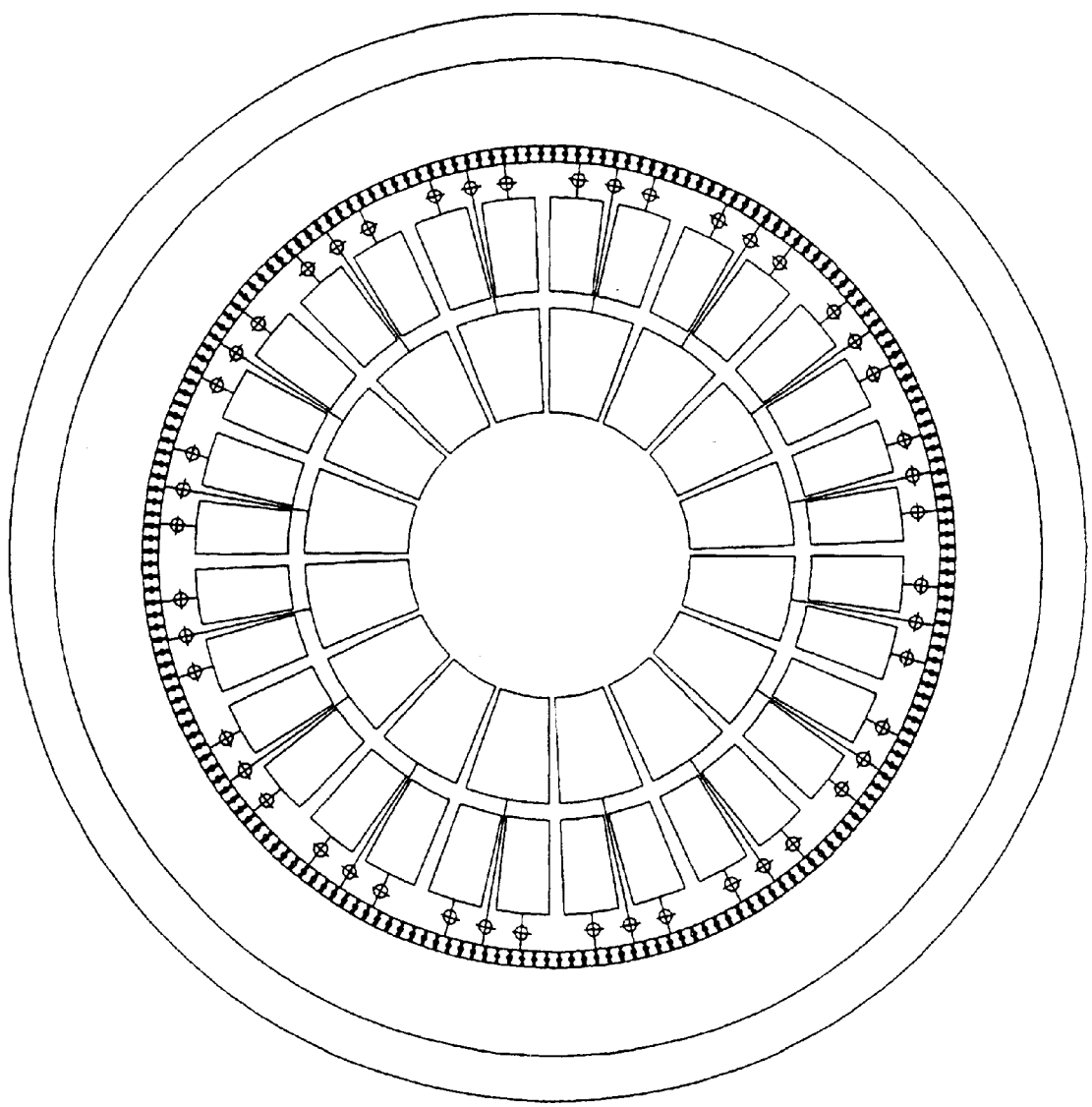
FIG. 23B is a schematic diagram of a disk configured for a multiplicity of DNA oligonucleotide syntheses.

DNA synthesis can also be performed upon preloaded CPG contained in reaction chambers toward the periphery of the disk and reagents delivered by the use of multiuse two-way valves, as schematically diagramed in FIG. 23A. In these disks, reaction chambers capable of containing 100 nL, spaced 150 μm on-center (measured from the center of one sphere to the center of the next sphere) in a disk of a 120 mm diameter, as many as 1250 reaction chambers can be manufactured.

Reagent reservoirs containing sufficient volumes to supply the reagent chambers on the disk are prefilled with the four phophoramidites, $CH_3CN$, TCA, oxidizer and capping reagents. Trityl-bearing CPG or linkers bound directly to the reaction chambers are similarly preloaded onto the disk. Microliter volumes of reagents are sufficient for each reaction. TCA is spun into each first reaction chamber and allowed to react for a defined length of time, typically one minute, then spun to a effluent (waste) chamber on the periphery of the disk. The $CH_3CN$ rinse is spun into each reaction chamber and then to waste. By selective valve actuation, the A, C, G, or T phosphoramidite is spun to the reaction chambers requiring that base and reacted for a defined time interval, typically three minutes, and the spun to waste. A $CH_3CN$ rinse is spun to each reaction chamber and after, to the waste chamber. The oxidizer mixture is spun into each reaction chamber, reacted for a defined time interval, typically one minute, then to waste. Another $CH_3CN$ rinse is spun to each reaction chamber and then to waste. The two-component capping reagent is spun to each reaction chamber and reacted for a defined time interval, typically one minute, then to waste. For each cycle, the final $CH_3CN$ rinse is then spun to each reaction chamber and then to the waste chamber. The cycle is repeated for a preprogrammed number of cycles until each oligonucleotide is completely synthesized. Concentrated ammonium hydroxide is then spun to each of the reaction chambers and reacted for a defined length of time, typically 6 hours, and reacted at 60° C. to deprotect and cleave the completed DNA from its support. The DNA can then be removed by manual or automated means. Conversely, the linkage of the oligonucleotide to the CPG support is chosen to be resistant to the action of ammonium hydroxide, so that the deprotected oligonucleotide remains in the reaction chambers bound to CPG.

Peptide synthesis disks are also provided, whereby the arrangement of reagent reservoirs and reaction chambers as described above is adapted for the synthetic reactions comprising a peptide synthesis regime.

EXAMPLE 7

Enzymatic DNA Sequencing

Figure 24:
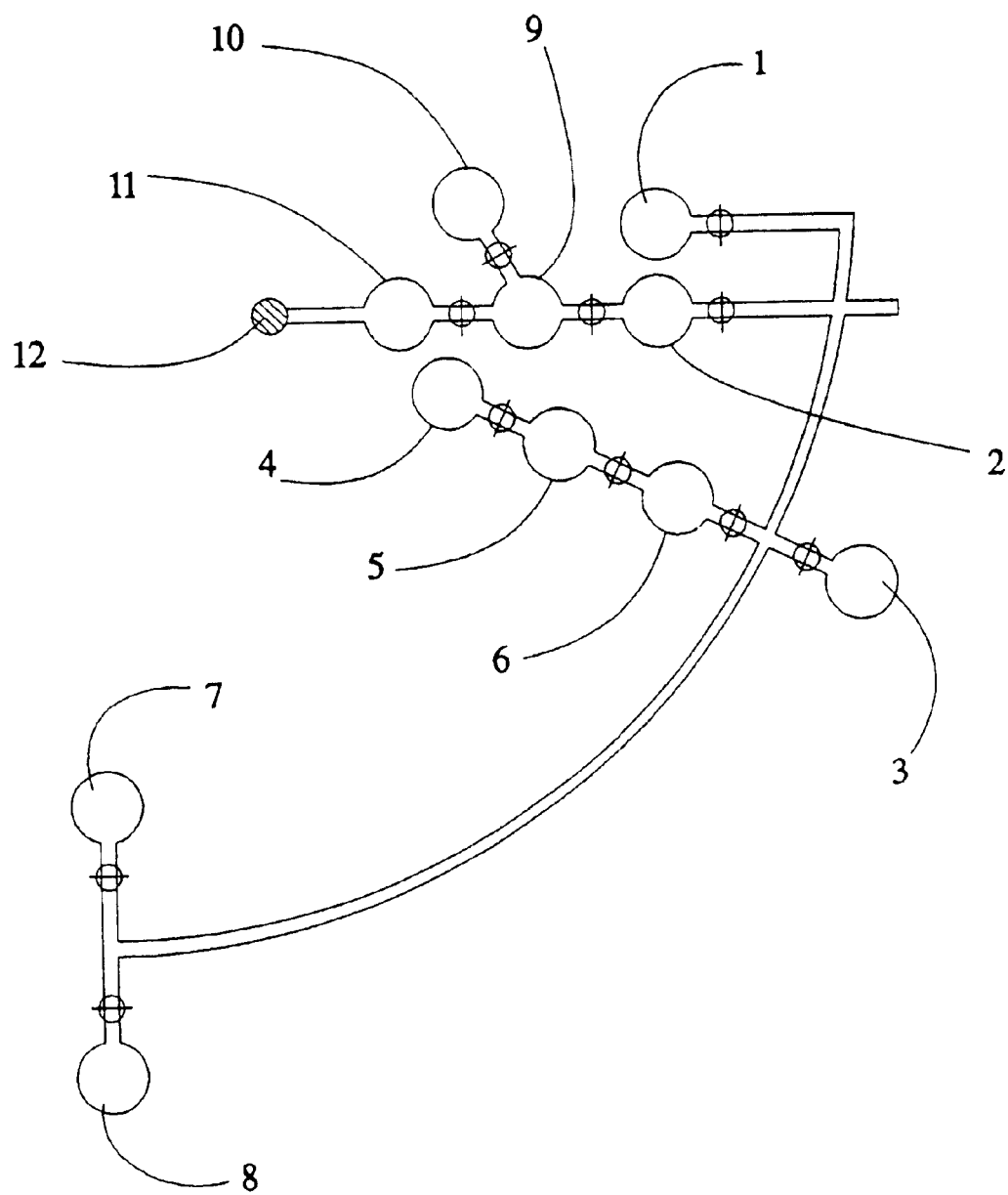
FIG. 24 is a schematic diagram of a disk configured for DNA sequencing.

The nucleotide sequence of a DNA fragment is determined by the Sanger enzymatic sequencing method using a disk prepared as described in Example 1 above (see FIG. 24).

Template DNA (200 pg in 250 mL) and 100 femtomoles of an appropriate primer are pipetted manually or by an automated process into a sample input port. The DNA is then transferred into a mixing chamber containing terminator solution (i.e., a solution comprising a dideoxy form of nucleotides G, A, T or C) by spinning the disk at a rotational speed of 1 to 30,000 rpm. Terminator solution typically comprises 100 nL of a solution containing 5 picomoles of each deoxynucleotide, 0.5 picomoles of one dideoxynucleotide covalently linked to a fluorescent label, 90 mM Tris-HCl-(pH 7.5), 45 mM $MgCl_2$ and 110 mM NaCl. The contents of the mixing chamber are transferred into a reaction chamber containing 0.1 units of T7 DNA polymerase (or, alternatively, 0.1 Units of Taq polymerase) and 20 nL 0.1M dithiothreitol (DTT) by spinning the disk at a rotational speed of 1 to 30,000 rpm, yielding a reaction mixture in the reaction chamber having a final concentration of buffer components that is 26 mM Tris-HCl (pH 7.5), 13 mM MgCl2, 32 mM NaCl, and 6 mM DTT. The reaction chamber is heated to 37° C. (or, alternatively, to 65° C. for Taq polymerase) by a resistive heating element integral to the disk, or alternatively, positioned within the device to specifically heat the reaction chamber, and incubated for a defined length of time, typically 1 minute. The reaction products are spun into an equal volume of 90% formamide/EDTA, heated to 90° C. for 1 minute and spun to a capillary electrophoresis unit on the disk. The set of dideoxynucleotide-terminated DNA fragments comprising the reaction mixture is then separated by capillary electrophoresis and the sequence of fragments determined by laser-induced fluorescence detection as described above. Disks comprising a multiplicity of these synthetic arrays, permitting simultaneous synthesis of a plurality of dideoxynucleotide-terminated oligonucleotides, are also provided. The deducted nucleotide sequence is determined from the pattern of fluorescence signals detected and the sequence is determined from the pattern of fluorescence signals detected and the sequence derived by the device microprocessor from these data.

EXAMPLE 8

Liquid Phase Synthesis and Analysis

Figure 25:
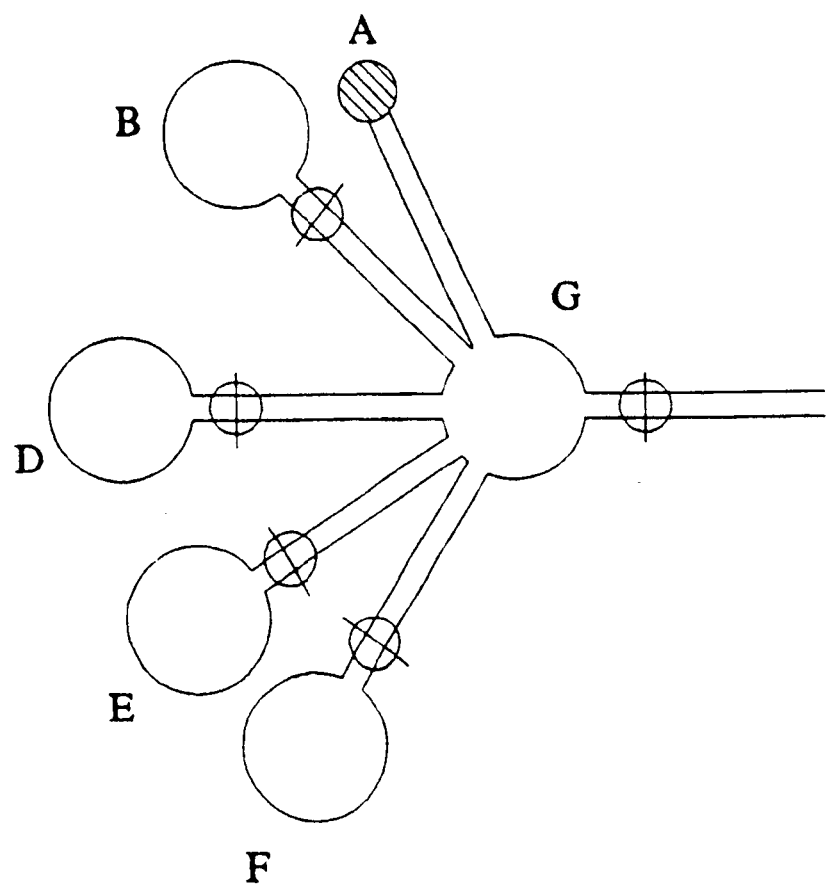
FIG. 25 is a schematic diagram of a disk configured for iron assay.

A variety of colorimetric chemical analyses are performed using a disk as described in Example 1. For example, a disk is provided (see FIG. 25) for performing a solution assay to determine iron concentration in a test solution (such as an industrial effluent) using a standard colorimetric test. The device is fabricated with reagent reservoir containing 40 uL 12N HCl 100 uL 10% hydroxylamine hydrochloride, 100 uL 10% sodium citrate buffer (pH 4), and 50 uL 0.02%, 1,10-phenanthroline. The reagent reservoirs are arranged as shown in FIG. 25 so that these reagents are added to a reaction chamber sequentially by opening valves controlling flow from each reagent reservoir. Reagent transfer to the reaction chamber is achieved by spinning the disk of Example 1 at a rotational speed of 1 to 30,000 rpm, whereby the centripetal force motivates each reagent solution from its reservoir to the reaction chamber. As shown in FIG. 25, sample is introduced through the sample port (A) and centripetally delivered to the reaction chamber. The valve to the reagent reservoir containing HCl (B) is opened and acid is added to the sample. The sample is incubated 10 minutes to dissolve all iron oxide present. Hydroxylamine hydrochloride (reservoir D) and citrate (reservoir E) are next added to the reaction mixture. The reaction mixture is incubated 20 minutes to ensure complete reduction of iron III to iron II. Next, 1,10-phenanthroline is transferred from reservoir F to complex the iron II and form a colored product. The solution is incubated 30 minutes at 30° C. to complete color development. Photometric measurement at 520 nm is done after the incubation process in a "read" cell (G) connected to the reaction chamber through valve G.

EXAMPLE 9

Solid Phase (Surface/Colloid) Synthesis/Analysis

Figure 26:
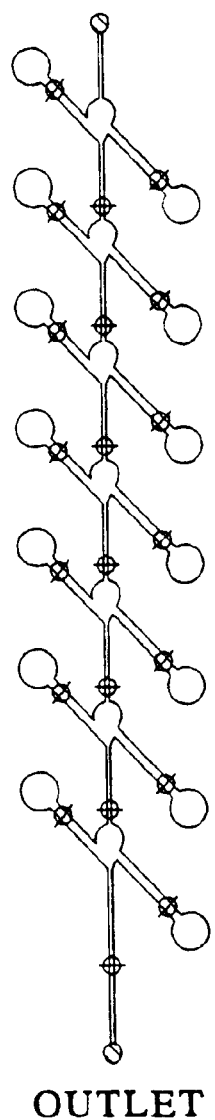
FIG. 26 is a schematic diagram of a disk configured for solid phase reaction.

Oligonucleotides, single-stranded DNA or duplex DNA is covalently linked to a reactive particle (such as a bead or magnetic particle or a chromatographic substrate) using a disk prepared as described in Example 1 and shown in FIG. 26. In the illustrate embodiment, a 25 uL aliquot of carboxy-activated magnetic particles (BioMag 4125, PerSeptive Diagnostics, Framingham, Mass.) is added to the disk through a sample introduction port. The particles are exchanged from the initial solution into 50 uL 0.1M imidazole (pH 6) by decanting the original solution through a valve to an effluent or waste reservoir, whereby the valve is configured to prevent loss of the magnetic particles from the reaction chamber. The imidazole solution is then added to the particle reaction chamber from an imidazole reservoir on the disk, transfer of imidazole being controlled by a valve. The motive force for both decanting the original magnetic particle solution and transferring imidazole from the imidazole reservoir to the particle reaction chamber is provided by spinning the disk at a rotational speed of 1 to 30,000 rpm. Specifically with reference to FIG. 26, as the disk spins the dense magnetic particles are pelleted in a funnel at the end of the reaction chamber and deposited to waste. A valve controlling an imidazole reagent chamber containing 50 uL of 0.1M imidazole is then opened above the particles but below the decanting level and used to transfer the particles through a valve in the reaction chamber and into the next decanting reservoir. This decanting process can be repeated many times to affect a change in the liquid phase to the desired composition. Typically, three exchanges are sufficient. Alternatively, appropriate configuration of the reagent and reaction chambers allows the magnetic particles to be exchanged within a single reaction chamber by controlled addition and removal of imidazole from clusters of reagent reservoirs, or alternatively, a single reagent reservoir large enough to contain sufficient imidazole for the entire cycle of exchange.

After the exchange cycle is complete, the magnetic particles are transferred to a next reaction chamber containing 250 ug dry 1-ethyl-3(3-dimenthylaminopropyl) carbodiimide (EDAC). A reagent reservoir containing 170 OD (170 ng) 5'-aminated DNA oligonucleotide in 50 uL of 0.1M imidazole solution chamber prior to addition of the particles in order to dissolve the EDAC. The particles are then added through a valve in about 100 uL 0.1M imidazole. Upon addition of the magnetic particles to the reaction chamber, the device is stopped and incubated 6 hours at 40° C. Heating can be effected by a heat source (such as Peltier heating device) embedded in the disk itself, or positioned in the instrument in a configuration permitting specific heating of the reaction chamber. In the latter alternative, the disk may be stopped at a predetermined position relative to the device to ensure specificity of heating of the reaction chamber.

After incubation, the particles are washed and exchanged into 100 uL portions of water by decanting as described above as the disk is spun. Three exchanges are typically performed to purify the particles. Product is advantageously collected in the extremity of the disk where it can easily be accessed for subsequent use. Disks comprising a multiplicity of these synthetic arrays, permitting simultaneous synthesis of a plurality of particle-linked oligonucleotides, are also provided.

EXAMPLE 10

Micro-Extraction System

Figure 27:
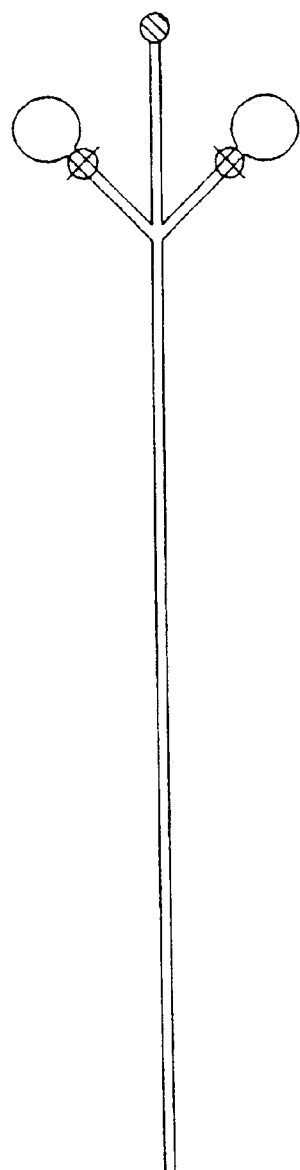
FIG. 27 is a schematic diagram of a disk configured for sample extraction.

A disk as described in Example 1 (see FIG. 27) for performing micro-extraction of a solute from a solution or of a component of a mixture as an alternative to HPLC or other conventional biochemical separation methodology. Specifically, a channel on the disk is coated with a compound (such as octanol) by standard procedures to provide a surface having an affinity for a component of a mixture, typically a complex chemical or biochemical mixture. With a silicon disk, for example, the surface of the channel is activated by filling the chamber with aqueous epoxysilane at 95° C. for 1 hour. The disk is washed about five times with distilled water to remove unreacted silane, and aminooctane is added in a solvent and incubated at 95° C. for 1 hour followed by solvent rinse to remove unreacted octane.

Sample mixture containing the component to be eluted is added to an injection port and moved through the coated separation channel by rotating the disk at 1 to 30,000 rpm. Reagent reservoirs are opened at the entrance of the channel and used to elute the sample retained on the coated channel to a collection reservoir. The isolated sample component is then collected at an outlet port.

EXAMPLE 11

Free Zone Capillary Electrophoresis

Figure 28:
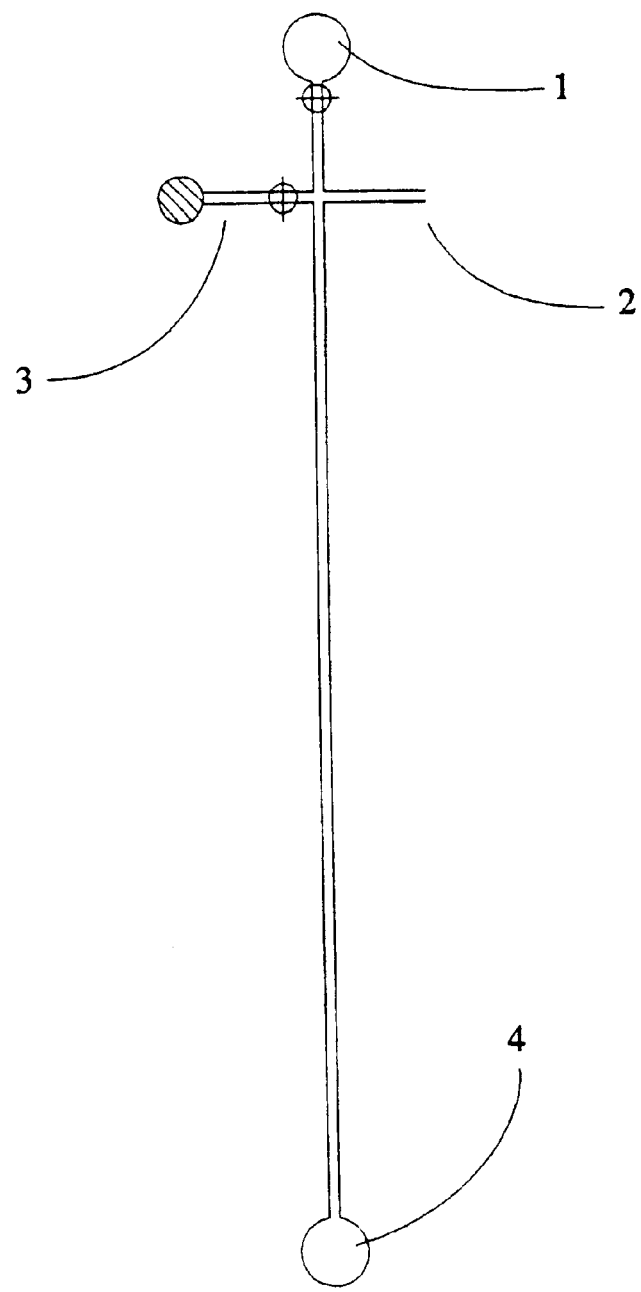
FIG. 28 is a schematic diagram of a disk configured for gel or capillary electrophoresis.

Free zone capillary electrophoresis is performed on a disk fabricated as described in Example 1 above, and schematically represented in FIG. 28. Specifically, a 5 $\mu$m×75 $\mu$m×25 mm capilliary (it will be recognized that all dimensions are approximate within limits of precision in fabricating components such as capillaries in the disk), is lithographically etched onto a glass disk. Electrical connections are made using standard methods by plating platinum onto the non-etched surface of the glass before sealing the top to the device. The separation channel is intersected by a 15 mm sample introduction channel, positioned 3 mm away from a buffer reservoir. The interesting channel has a sample inlet port at one end and electrical connections at either end to control sample application to the capillary.

In the practice of capillary electrophoresis on the disk, the separation channel is filled from the buffer reservoir by rotation of the disk at a speed of 1 to 30,000 rpm. Once the channel is filled, rotation is stopped until pressure needs to be applied to the channel again. Sample is introduced by applying a voltage between the intersecting analyte inlet and analyte outlet channels on the chip (see FIG. 28) A 50 V potential drop is applied between the sample inlet and outlet ports while the separation channel ports float. The sample, comprising a solution of 5 mM EDTA, 1 mM Tris-HCl (pH 8) with 1 mM $Mg^{2+}$ and 1 mM $Ca^{2+}$ (typically prepared from the chloride salt). The running buffer consists of 10 mM Tris-HCl (pH 8), 5 mM EDTA. Separation toward the cathode is then performed by floating the electric potential at the sample reservoir and applying 250 V along the separation channel. Separation is monitored at a position 2 cm from the inlet port by monitoring, e.g. UV absorbance at 254 nm using a UV light source (mercury lamp) and a photodiode detector, positioned on the device to interest the capillary channel.

EXAMPLE 12

DNA Electrophoresis

Figure 29:
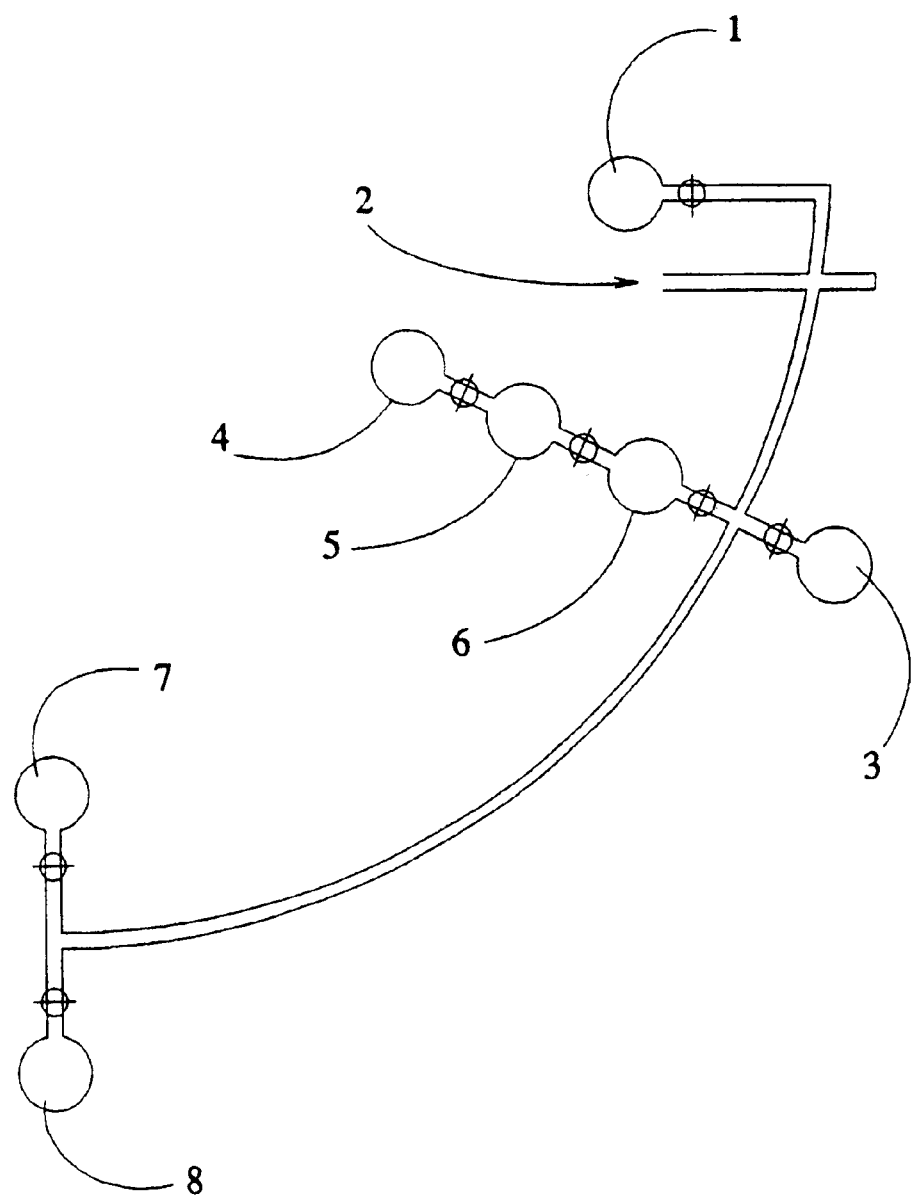
FIG. 29 is a schematic diagram of a transverse optical path in a microplatform.

Gel electrophoresis is performed on a disk prepared as described in Example 1 above. For this application, a gel media is prepared in the separation channel; however, such gel media must be protected from sheer forces that develop with rotation of the disk during transfer of sample or buffer to the electrophoresis channel. Thus, the gel-filled capillary is advantageously arrayed concentrically on the disk, as shown schematically in FIG. 29. As a result, the gel will only experience shear forces from centripetal-induced pressure during rotation if a fluid reservoir is in contact with the capillary during rotation of the disk. At rest, the planar geometry of the disk prevents hydrodynamic pressure on the capillary. This is an advantage over standard capillary electrophoresis systems, where hydrodynamic pressure is not so easily controlled because the buffer volumes and reservoir heights need to be carefully adjusted before each run to avoid hydrodynamic flow. This is also an advantage of capillary electrophoresis performed on the disks of the invention over electrophoresis performed on microchips, where buffer reservoirs are positioned above the plane of the separation channel and are thereby susceptible to hydrodynamic pressure-driven fluid flow. Gel electrophoresis is performed on the disks of the invention to separate DNA fragments, including duplex PCR fragments, oligonucleotides and single-stranded, dideoxynucleotide-terminated enzymatic DNA sequencing components, the system is configured as shown in FIG. 29. The disk is prepared comprising a polyacrylamide gel concentrically arrayed in a microetched separation channel in the disk. The polyacrylamide gel is prepared from an unpolymerized solution of 7M urea, 45 mM Tris-borate buffer (pH 8.3), 1 mm EDTA, 9% acrylamide, 0.1% TEMED and 10% ammonium persulfate. The disk can be prepared in the separation channel by mixing the components (wherein it will be recognized that unpolymerized polymerized polyacrylamide is susceptible to light-catalyzed polymerization upon storage) particularly by introducing TEMED and ammonium persulfate to the mixture. Sufficient gel mixture is added to the separation channel by opening a valve from a mixing chamber to the separation channel and rotating the disk at 1 to 30,000 rpm. The disk is stopped upon filing of the separation channel to permit gel polymerization. Shortly before polymerization is complete, the exit channel is flushed to eliminate bubbles and unpolymerized monomer by flushing the channel with buffer from a large buffer reservoir at the outlet side of the channel, controlled by a valve. A similar process is conducted on the inlet side of the gel.

To introduce a DNA sample, a valve is opened from an inlet port holding a solution of DNA fragments, or alternatively, the sample is pipetted directly onto the disk. The sample is applied to the separation channel by spinning the disk at 1 to 30,000 rpm, forcing sample and buffer into the buffer filled channel above the gel. Upon introduction of the sample to the separation channel and the sample inlet channel. Sample concentrates at the gel/buffer interface before entering the separation matrix, analogous to sample concentration during conventional slab gel electrophoresis. Electrophoresis is performed at 250 V/cm to effect a separation of DNA fragments, the cathode (positive electrode) being positioned at the outlet end of the channel distal to the sample inlet channel. A laser induced fluorescence detector is positioned at the outlet of the gel filled capillary chamber to detect the labeled DNA fragments, as described above in Example 2.

EXAMPLE 13

Spectrophotometer Pathlength Extension

Spectrophotometric measurements in a rotating structure of the invention can be limited by the relatively small pathlengths provided by spectrophotometric illumination across the transverse dimension of the disk. The intensity of absorbance of a solution is dependent on the depth of the absorbing layer, as well as the concentration of the absorbing molecules (as described in the Lambert-Beer law).

Although a measurement cell in a rotating microsystem platform of the invention presents a short transverse pathlength, the lateral pathlength through the disk can be extensive (i.e., centimeters versus millimeters). Spectral measurements can be enhanced by introducing light through the detection chamber in the lateral dimension.

Figure 16:
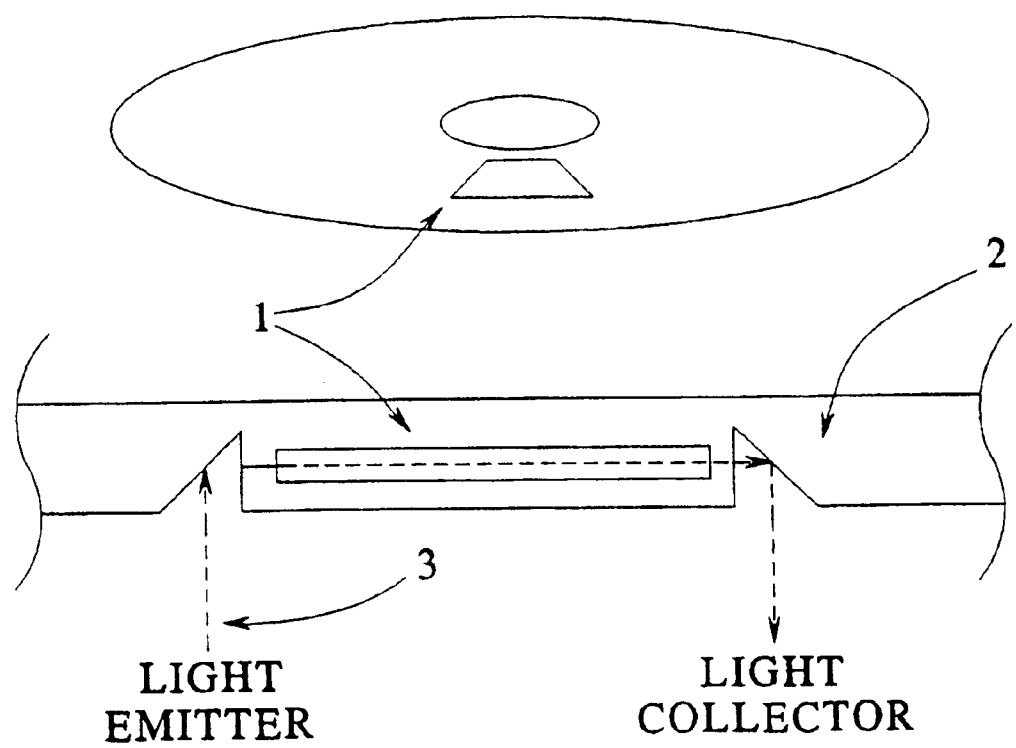
FIG. 16 is a schematic diagram of a transverse spectroscopic detection chamber.

One arrangement providing transverse illumination in the lateral dimension is shown in FIG. 16. Light is beamed in a perpendicular direction towards the disk. A mirror is positioned at a 45° angle to the direction of the illuminating beam, whereby the light is directed laterally through the detection chamber. Light passes through the detection cell and is redirected by another 45° mirror onto a photosensitive detector, such as a photodiode or photomultiplier tube. These mirrors can be inserted onto the disk, integrally molded into the disk or metallicized in the plastic or other substrate comprising the disk.

EXAMPLE 14

Cell Counting, Identification and Monitoring

Methods for identifying particular cells or cell types in a biological sample are provided. For example, a microplatform of the invention is prepared by having a surface adsorbly coated with monoclonal antibody specific to *E. coli.*, the remaining sites being blocked with BSA. A milk sample is introduced onto the disk and placed into contact with a reaction chamber comprising the surface coated with the antibody. The milk is incubated in this chamber for 30 min. The microsystem platform is then rotated to remove unwanted materials. An amount of a buffer appropriate for washing the microsystem chamber is then added to the surface or chamber through a microchannel from a reservoir containing washing buffer, said buffer being released by centrifugal force and opening of a microvalve. In a useful embodiment, the washing buffer comprises an *E. coli*-specific monoclonal antibody crosslinked to an enzyme (such peroxidase). Thus incubation is allowed to proceed for 5 min. The disk is again spun with the opening of the appropriate microvalves to remove the washing solution from the chamber and to add a solution containing an enzymatic substrate (tetramethylbenzidine and hydrogen peroxide, maintained heretofore in a reagent reservoir connected to the reaction chamber by a microvalve-controlled microchannel. The amount of *E. Coli* bound in the reaction chamber is quantititated with regard to the amount of detected enzymatic activity, which is determined spectrophotometrically by the appearance of a light-absorbing product or the disappearance of a light-absorbing substrate.

It should be understood that the foregoing disclosure emphasizes certain specific embodiments of the invention and that all modifications or alternatives equivalent thereto are within the spirit and scope of the invention.

What is claimed is:

1. A method for measuring the amount of an analyte in a biological sample, the method comprising the steps of:
    a) applying the biological sample to a sample inlet port of a microsystem platform of centripetally-motivated fluid micromanipulation apparatus comprising a microsystem platform, wherein the microsystem platform comprises:
        i) a multiplicity of sample inlet ports, arranged concentrically around the center of the platform, wherein each of the sample inlet ports is operatively linked to
        ii) a multiplicity of microchannels arrayed radially away from the center of the platform, said microchannels being operatively linked to
        iii) a multiplicity of reagent reservoirs containing a reagent specific for the analyte to be measured, wherein release of the reagent from each of the reservoirs is controlled by a microvalve, wherein the microvalves are in electrical contact with a controller unit, and wherein the multiplicity of microchannels is also operatively linked to
        iv) a multiplicity of analyte detection chambers arranged peripherally around the outer edge of the microplatform,
        wherein movement of the biological sample from the sample inlet port and through the microchannel, and movement of the reagent from the reagent reservoir and through the microchannel, is motivated by centripetal force generated by rotational motion of the microsystem platform,
    b) placing the microsystem platform in a micromanipulation apparatus,
    c) providing rotational motion to the microsystem platform for a time and at a velocity sufficient to motivate the biological sample containing the analyte from the sample inlet port through the microchannel,
    d) opening each of the microvalves controlling release of the reagent from the reagent reservoirs by generating a signal from the controlling unit, at a time and for a duration, whereby the reagent moves into the microchannel and is mixed with the biological sample,
    e) observing the mixture of the biological sample and the reagent in the analyte detection chamber, whereby a detector within the micromanipulation apparatus detects a signal proportional to the amount of the analyte present in the biological sample, and
    f) recording the measurement of the amount of the analyte in the biological sample.

2. The method of claim 1, wherein the biological sample is blood, urine, cerebrospinal fluid, plasma, saliva, semen, or amniotic fluid.

3. The method of claim 1, wherein the measurement of the amount of analyte in the sample is recorded in the device, on the microplatform, or both.

4. The method of claim 1, wherein the analyte detection chamber on the microsystem platform is optically transparent.

5. The method of claim 1, wherein the signal detected in the analyte detection chamber is detected at a frequency equal to the frequency of rotation of the platform or multiples thereof.

6. The method of claim 1, wherein the signal detected is a monochromatic light signal.

7. The method of claim 6, wherein the signal detected is a fluorescence signal, a chemiluminescence signal or a colorimetric signal.

8. A method for detecting gas or particles comprising an environmental sample, wherein the method comprises the steps of:
   a) Contacting the environmental sample with a sample inlet port of a microsystem platform of a centripetally-motivated fluid micromanipulation apparatus comprising a microsystem platform, wherein the microsystem platform comprises:
      i) a multiplicity of sample inlet ports, arranged concentrically around the center of the platform, wherein the sample ports comprise an air intake vent and a connecting funnel channel, wherein each of the sample inlet ports is operatively linked to
      ii) a multiplicity of microchannels arrayed radially away from the center of the platform, said microchannels being operatively linked to
      iii) a multiplicity of reagent reservoirs containing a reagent specific for the gas or particles to be detected, wherein release of the reagent from each of the reservoirs is controlled by a microvalve, wherein the microvalves are in electrical contact with a controller unit, and wherein the multiplicity of microchannels is also operatively linked to
      iv) a multiplicity of gas or particle detectors arranged peripherally around the outer edge of the microplatform,
   wherein movement of the environmental sample from the sample inlet port and through the microchannel, and movement of the reagent from the reagent from the reagent reservoir and through the microchannel is motivated by centripetal force generated by rotational motion of the micro system platform,
   b) placing the mcirosystem platform in a micromanipulation device,
   c) providing rotational motion to the microsystem platform for a time and at a velocity sufficient to motivate the gaseous or particulate environmental sample from the sample inlet port through the microchannel,
   d) opening each of the microvalves controlling the release of the reagent from the reagent reservoirs by generating a signal from the controlling unit, at a time and duration wherby the reagent moves into the microchannel and is mixed with the environmental sample,
   e) detecting the mixture of the environmental sample and the reagent or the gaseous or particulate component of the environmental sample directly in the gas or particle detection chamber, whereby each of the detectors detects a signal proportional to the amount of the gas or particulate present in the environmental sample, and
   f) recording the measurement of the amount of the gas or particulate in the environmental sample.

9. The method of claim 8, wherein the environmental sample comprises air, water, soil, or disrupted biological matter.

10. The method of claim 8, wherein a gas is detected by a gas sensor chip.

11. The method of claim 8, wherein a particle is detected in an optically-transparent particle collection chamber.

12. The method of claim 8, wherein the particle is detected by coherent light scattering.

13. The method of claim 8, wherein a particle is detected in a particle collection chamber operatively connected by a microchannel to a reagent reservoir comprising a reagent for chemically testing the particles, wherein the particulate is mixed and reacted with the reagent in the microchannel after release of the reagent by activation of a microvalve and rotation of the platform.

14. A method for determining a hematocrit value from a blood sample, the method comprising the steps of
   a) applying the blood sample to the proximal end of a microchannel of a microsystem platform of centripetally-motivated fluid micromanipulation apparatus comprising a micromanipulation device and a microsystem platform, wherein the microsystem platform comprises
      i) a radial array of microchannels having a diameter of about 100 $\mu$m wherein the microchannels are treated with heparin to prevent coagulation, and wherein the microchannels are open at one end proximal to the center of the disk, the apparatus also comprising a coherent light source and a recording means operatively connected thereto comprising the micromanipulation device, and wherein movement of the blood sample through the microchannel is motivated by centripetal force generated by rotational motion of the microsystem platform,
   b) placing the microsystems platform in a micromanipulation device,
   c) providing rotational motion to the Microsystems platform for a time and at a velocity sufficient to motivate the red blood cells comprising the blood sample to move along the extent of the microchannel,
   d) scanning the microchannel along its length with the coherent light source,
   e) detecting a change in light scatter at a position along the microchannel that defines a boundary between the red blood cells and blood plasma,
   f) recording the position of the boundary for each microchannel, and
   g) comparing the position of this boundary for each microchannel with a standard curve relating hematocrit values to the position of the boundary, and recording the hematocrit determined thereby.

* * * * *